United States Patent
Melander et al.

(10) Patent No.: US 8,884,022 B2
(45) Date of Patent: *Nov. 11, 2014

(54) INHIBITION OF BACTERIAL BIOFILMS WITH ARYL CARBAMATES

(71) Applicant: North Carolina State University, Raleigh, NC (US)

(72) Inventors: Christian Melander, Raleigh, NC (US); Steven A. Rogers, Lawrence, KS (US)

(73) Assignee: North Carolina State University, Raleigh, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/734,122

(22) Filed: Jan. 4, 2013

(65) Prior Publication Data
US 2013/0123225 A1    May 16, 2013

Related U.S. Application Data

(63) Continuation of application No. PCT/US2011/042941, filed on Jul. 5, 2011.

(60) Provisional application No. 61/361,654, filed on Jul. 6, 2010.

(51) Int. Cl.
| C07D 213/58 | (2006.01) |
| C07D 215/08 | (2006.01) |
| C07D 213/55 | (2006.01) |
| C07D 249/04 | (2006.01) |
| C07D 215/34 | (2006.01) |
| A01N 43/647 | (2006.01) |
| A01N 43/42  | (2006.01) |
| C07J 43/00  | (2006.01) |
| A01N 43/40  | (2006.01) |
| C07J 41/00  | (2006.01) |

(52) U.S. Cl.
CPC ............ *C07D 249/04* (2013.01); *C07D 213/58* (2013.01); *C07D 215/34* (2013.01); *A01N 43/42* (2013.01); *C07J 43/003* (2013.01); *A01N 43/647* (2013.01); *A01N 43/40* (2013.01); *C07D 213/55* (2013.01); *C07D 215/08* (2013.01); *C07J 41/0055* (2013.01)
USPC ........... 546/329; 546/297; 546/331; 546/337; 546/165; 514/357; 514/176; 514/359; 514/311; 525/178; 525/184; 540/108; 548/255

(58) Field of Classification Search
USPC .......................................... 546/297; 514/357
See application file for complete search history.

(56) References Cited

U.S. PATENT DOCUMENTS

| 4,373,105 A | * | 2/1983 | Rohr et al. ...................... 560/27 |
| 5,411,967 A | * | 5/1995 | Kao et al. ...................... 514/291 |

(Continued)

FOREIGN PATENT DOCUMENTS

| EP | 0017411 | * | 10/1980 |
| JP | 11035545 | * | 2/1999 |
| WO | WO 2009/144179 A1 | | 12/2009 |

OTHER PUBLICATIONS

Tsuji; Tetrahedron: Asymmetry, 2003, 14 177-180.*

(Continued)

*Primary Examiner* — John Mabry
*Assistant Examiner* — Daniel Carcanague
(74) *Attorney, Agent, or Firm* — Myers Bigel Sibley & Sajovec, P.A.

(57) ABSTRACT

Disclosure is provided for carbamate compounds that prevent, remove and/or inhibit the formation of biofilms, compositions including these compounds, devices including these compounds, and methods of using the same.

9 Claims, 8 Drawing Sheets

(56) References Cited

U.S. PATENT DOCUMENTS

| | | | |
|---|---|---|---|
| 6,239,175 B1 | 5/2001 | Hinks et al. | |
| 7,074,742 B2* | 7/2006 | Neubert et al. | 504/130 |
| 7,291,641 B2* | 11/2007 | Chabrier De Lassauniere et al. | 514/400 |
| 2004/0072880 A1* | 4/2004 | Lloyd et al. | 514/362 |
| 2007/0014739 A1 | 1/2007 | Eldridge et al. | |
| 2007/0276010 A1* | 11/2007 | Benbow et al. | 514/341 |

OTHER PUBLICATIONS

Wermuth; Practice of Medicinal Chemistry, Third edition, 2008, Elsevier, pp. 126, 298, 401-403, 431.*

Georgio; Chirality, 2007, 19, 434-445.*

Wolff, Manfred E. "Burger's Medicinal Chemistry, 5ed, Part I", John Wiley & Sons, 1995, pp. 975-977.*

Banker, G.S. et al., "Modern Pharmaceutics, 3ed.", Marcel Dekker, New York, 1996, pp. 451 and 596.*

U.S. Appl. No. 13/778,425, Melander et al.

Rogers SA et al. Synthesis and bacterial biofilm inhibition studies of ethyl N—(2-phenethyl) carbamate derivatives. Organic and Biomolecular Chemistry. 2010; 8, 3857-3859.

Yamada A et al. Development of Chemical Substances Regulating Biofilm Formation. Bull. Chem. Soc. Jpn. 1997; 70, 3061-3069.

Schelz Z et al. Antimicrobial and antiplasmid activities of essential oils. Fitoterapia. 2006; 77(4), 279-285. Abstract only.

Filoche SK et al. Antimicrobial effects of essential oils in combination with chlorhexidine digluconate. Oral Microb. Immun. 2005; 20, 221-225.

Iscan G et al. Antimicrobial Screening of *Mentha piperita* Essential Oils. J. Agric. Food Chem. 2002; 50, 3943-3946.

Kurita N and Koike S. Synergistic Antimicrobial Effect of Sodium Chloride and Essential Oil Components. Agric. Biol. Chem. 1982; 46(1), 159-165.

Aridogan BC et al. Antimicrobial Activity and Chemical Composition of Some Essential Oils. Arch. Pharm. Res. 2002; 25(6), 860-864.

Ben Afra A et al. Antimicrobial activity of carvacrol related to its chemical structure. Lett. Appl. Microbiol. 2006; 43, 149-154.

Sivropoulou A et al. Antimicrobial and Cytotoxic Activities of *Origanum* Essential Oils. J. Agric. Food Chem. 1996; 44, 1202-1205.

Ultee A et al. Antimicrobial Activity of Carvacrol toward *Bacillus cereus* on Rice. J. Food Protect. 2000; 63(5), 620-624.

Rogers SA et al. Synthesis and biological evaluation of 2-aminoimadazole/carbamate hybrid anti-biofilm and anti-microbial agents. Bioorganic and Medicinal Chemistry Letters. 2011; 1257-1260. Abstract only.

Rogers SA et al. Synthesis and bacterial biofilm inhibition studies of ethyl N—(2-phenethyl) carbamate derivatives. Organic and Biomolecular Chemistry. 2010; 14, 3 pp. DOI:10.1039/C0OB00063A.

International Search Report and Written Opinion, PCT/US2011/042941, mailed Nov. 18, 2011.

Schelz Z et al. Antimicrobial and antiplasmid activities of essential oils. Fitoterapia. 2006; 77(4), 279-285.

Rogers SA et al. Synthesis and biological evaluation of 2-aminoimadazole/carbamate hybrid anti-biofilm and anti-microbial agents. Bioorganic and Medicinal Chemistry Letters. 2011; 1257-1260.

* cited by examiner

INHIBITION OF BACTERIAL BIOFILMS WITH ARYL CARBAMATES

RELATED APPLICATIONS

This application is a continuation of PCT Patent Application No. PCT/US2011/042941, filed Jul. 5, 2011, which claims the benefit under 35 U.S.C. §119(e) to U.S. Provisional Patent Application No. 61/361,654, filed Jul. 6, 2010, the contents of each of which is incorporated by reference herein in its entirety.

FIELD OF THE INVENTION

This invention relates to compounds, compositions and methods useful for controlling biofilms.

BACKGROUND OF THE INVENTION

Biofilms are complex communities of microorganisms that are commonly found on a variety of substrates or surfaces that are moist or submerged (Musk et al., *Curr. Med. Chem.*, 2006, 13, 2163; Donlan et al., *Clin. Microbiol. Rev.*, 2002, 15, 167). Though primarily populated by bacteria, biofilms can also contain many different individual types of microorganisms, e.g., bacteria, archaea, protozoa and algae. The formation of biofilms can be thought of as a developmental process in which a few free-swimming (planktonic) bacteria adhere to a solid surface and, in response to appropriate signals, initiate the formation of a complex sessile microcolony existing as a community of bacteria and other organisms. Bacteria within biofilms are usually embedded within a matrix, which can consist of protein, polysaccharide, nucleic acids, or combinations of these macromolecules. The matrix is a critical feature of the biofilm that protects the inhabiting organisms from antiseptics, microbicides, and host cells. It has been estimated that bacteria within biofilms are upwards of 1.000-fold more resistant to conventional antibiotics (Rasmussen et al., *Int. J. Med. Microbiol.*, 2006, 296, 149).

Biofilms play a significant role in infectious disease. It is estimated that biofilms account for between 50-80% of microbial infections in the body, and that the cost of these infections exceeds $1 billion annually. For example, persistent infections of indwelling medical devices remain a serious problem for patients, because eradication of these infections is virtually impossible. A few diseases in which biofilms have been implicated include endocarditis, otitis media, chronic prostatitis, periodontal disease, chronic urinary tract infections, and cystic fibrosis. The persistence of biofilm populations is linked to their inherent insensitivity to antiseptics, antibiotics, and other antimicrobial compounds or host cells.

Deleterious effects of biofilms are also found in non-medical settings. For example, biofilms are a major problem in the shipping industry. Biofilms form on and promote the corrosion of ship hulls and also increase the roughness of the hulls, increasing the drag on the ships and thereby increasing fuel costs. The biofilms can also promote the attachment of larger living structures, such as barnacles, to the hull. Fuel can account for half of the cost of marine shipping, and the loss in fuel efficiency due to biofilm formation is substantial. One method of controlling biofilms is to simply scrape the films off of the hulls. However, this method is costly and time-consuming, and can promote the spread of troublesome non-native species in shipping waters. Another method involves the use of antifouling coatings containing tin. However, tin-based coatings are now disfavored due to toxicity concerns.

Given the breadth of detrimental effects caused by bacterial biofilms, there has been an effort to develop small molecules that will inhibit their formation (Musk et al., *Curr. Med. Chem.*, 2006, 13, 2163). The underlying principle is that if bacteria can be maintained in the planktonic state, they will either not attach to a target surface and/or they can be killed by a lower dose of microbicide.

Despite the extent of biofilm driven problems, examples of structural scaffolds that inhibit biofilm formation are rare (Musk et al., *Curr. Med. Chem.*, 2006, 13, 2163). The few known examples include the homoserine lactones (Geske et al., *J. Am. Chem. Soc.*, 2005, 127, 12762), which are naturally-occurring bacterial signaling molecules that bacteria use in quorum sensing (Dong et al., *J. Microbiol.*, 2005, 43, 101; Nealson et al., *J. Bacteriol.*, 1970, 104, 313), brominated furanones isolated from the macroalga *Delisea pulchra* (Hentzer et al., *Microbiology-Sgm*, 2002, 148, 87), and ursene triterpenes from the plant *Diospyros dendo* (Hu et al., *J. Nat. Prod.*, 2006, 69, 118).

In addition, bacteria have an unparalleled ability to overcome foreign chemical insult. For example, resistance to vancomycin, "the antibiotic of last resort," has become more prevalent, and strains of vancomycin-resistant *Staphylococcus aureus* have become a serious health risk. It has been predicted that it is simply a matter of time before different bacterial strains develop vancomycin resistance, and the safety net that vancomycin has provided for decades in antibiotic therapy will no longer be available. Therefore, the identification of chemical architectures useful to inhibit biofilm development is needed.

Because of their natural resistance to antibiotics, phagocytic cells, and other biocides, biofilms are difficult, if not impossible, to eradicate. Therefore, the identification of compounds that control biofilms is of critical need.

SUMMARY OF THE INVENTION

Provided herein are compounds of Formula (I):

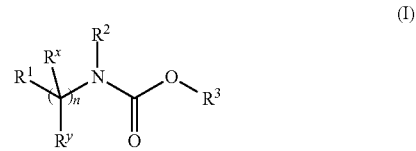

wherein:

$R^1$ is an aryl, an amine-substituted aryl, or $R^1$ is a heteroaryl having at least one nitrogen atom;

n=0 to 10, saturated or unsaturated;

each occurrence of $R^x$ and $R^y$ is present or absent (depending upon chain saturation), and is each independently H or alkyl;

$R^2$ is selected from the group consisting of: H, alkyl, alkenyl and alkynyl; and $R^3$ is alkyl, substituted cycloalkyl or unsubstituted cycloalkyl, or a pharmaceutically acceptable salt or prodrug thereof.

In some embodiments of Formula (I), $R^1$ is selected from the group consisting of:

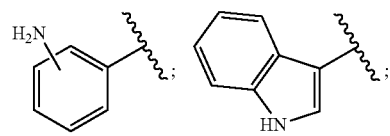

-continued

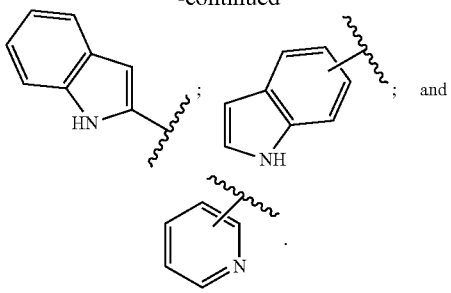

In some embodiments of Formula (I), the compound is a compound of Formula (I)(a):

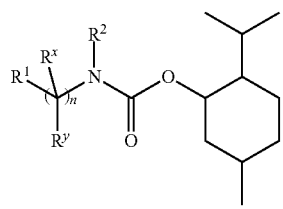
(I)(a)

wherein:
R¹ is an amine-substituted aryl, or R¹ is a heteroaryl having at least one nitrogen atom;
n=0 to 10, saturated or unsaturated;
each occurrence of $R^x$ and $R^y$ is present or absent (depending upon chain saturation), and is each independently H or alkyl; and
$R^2$ is selected from the group consisting of: H, alkyl, alkenyl and alkynyl,
or a pharmaceutically acceptable salt or prodrug thereof.
In some embodiments of Formula (I)(a), R¹ is selected from the group consisting of:

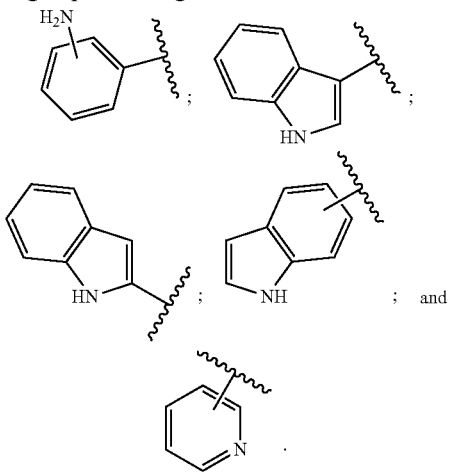

In some embodiments of Formula (I), the compound is a compound of Formula (I)(a)(i):

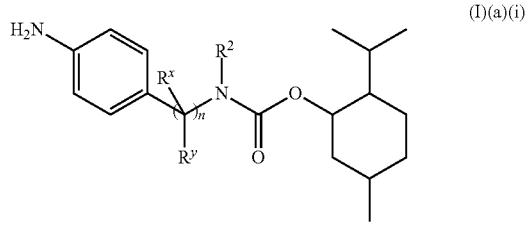
(I)(a)(i)

wherein:
n=0 to 10, saturated or unsaturated;
each occurrence of $R^x$ and $R^y$ is present or absent (depending upon chain saturation), and is each independently H or alkyl; and
$R^2$ is selected from the group consisting of: H, alkyl, alkenyl and alkynyl,
or a pharmaceutically acceptable salt or prodrug thereof.
In some embodiments of Formula (I), the compound is a compound of Formula (I)(a)(ii):

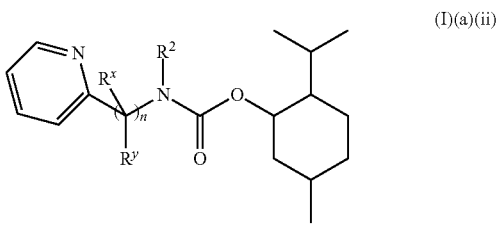
(I)(a)(ii)

wherein:
n=0 to 10, saturated or unsaturated;
each occurrence of $R^x$ and $R^y$ is present or absent (depending upon chain saturation), and is each independently H or alkyl; and
$R^2$ is selected from the group consisting of: H, alkyl, alkenyl and alkynyl,
or a pharmaceutically acceptable salt or prodrug thereof.
In some embodiments of Formula (I), the compound is a compound of Formula (I)(a)(iii):

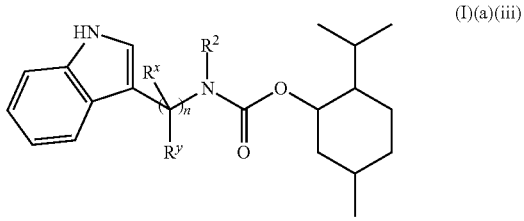
(I)(a)(iii)

wherein:
n=0 to 10, saturated or unsaturated;
each occurrence of $R^x$ and $R^y$ is present or absent (depending upon chain saturation), and is each independently H or alkyl; and
$R^2$ is selected from the group consisting of: H, alkyl, alkenyl and alkynyl,
or a pharmaceutically acceptable salt or prodrug thereof.
In some embodiments of Formula (I), the compound is selected from the group consisting of:

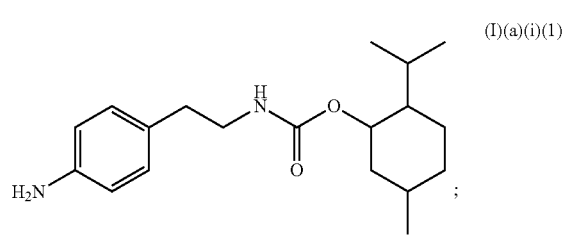
(I)(a)(i)(1)

-continued

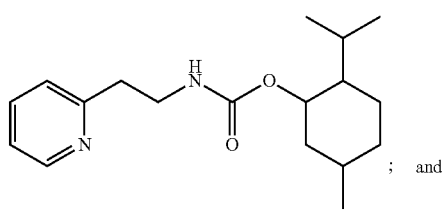
(I)(a)(ii)(1)

; and

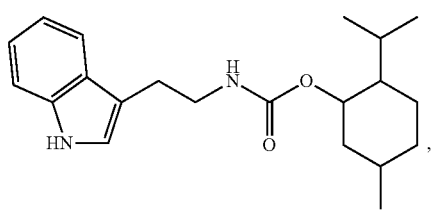
(I)(a)(iii)(1)

, or a pharmaceutically acceptable salt or prodrug thereof.

Biofilm inhibiting compositions are provided, which include a carrier and an effective amount of a compound disclosed herein. Compositions are also provided that include a compound disclosed herein in a pharmaceutically acceptable carrier.

Compositions are further provided that include a compound disclosed herein covalently coupled to a substrate. In some embodiments, the substrate includes a polymeric material. In some embodiments, the substrate includes a solid support. In some embodiments, the substrate includes a drainpipe, glaze ceramic, porcelain, glass, metal, wood, chrome, plastic, vinyl, and Formica® brand laminate (The Diller Corporation, Cincinnati, Ohio). In some embodiments, the substrate includes shower curtains or liners, upholstery, laundry, and carpeting.

Biofilm inhibiting coating compositions are provided, including: (a) a film-forming resin; (b) a solvent that disperses said resin; (c) an effective amount of the compounds or compositions disclosed herein, wherein said effective amount inhibits the growth of a biofilm thereon; and (d) optionally, at least one pigment. In some embodiments, the compound is covalently coupled to the resin. In some embodiments, the resin includes a polymeric material.

Substrates coated with coating composition disclosed herein are also provided. In some embodiments, the substrate includes a polymeric material. In some embodiments, the substrate includes a solid support. In some embodiments, the substrate includes a drainpipe, glaze ceramic, porcelain, glass, metal, wood, chrome, plastic or polymeric material, vinyl, and laminates thereof such as Formica® brand laminate. In some embodiments, the substrate includes shower curtains or liners, upholstery, laundry, and carpeting.

Methods of controlling biofilm formation on a substrate are provided, including the step of contacting the substrate with a compound and/or composition disclosed herein in an amount effective to inhibit biofilm formation. In some embodiments, the substrate may include a drainpipe, glaze ceramic, porcelain, glass, metal, wood, chrome, plastic or polymeric material, vinyl, and laminates thereof such as Formica® brand laminate. In some embodiments, the biofilm includes Gram-positive bacteria.

Methods for treating and/or preventing a bacterial infection in a subject in need thereof are provided, including administering to said subject a compound and/or composition disclosed herein in an amount effective to inhibit a biofilm component of said bacterial infection.

Also provided are medical devices, including (a) a medical device substrate; and (b) an effective amount of a compound disclosed herein, either coating the substrate, or incorporated into the substrate, wherein said effective amount inhibits the growth of a biofilm thereon. In some embodiments, the medical device substrate may include stents, fasteners, ports, catheters, scaffolds and grafts. In some embodiments, the compound is covalently coupled to said substrate.

Compounds and/or compositions for use in a method to control a biofilm are further provided. Also provided is the use of compounds and/or compositions disclosed herein for the preparation of a medicament for the treatment and/or prevention of a bacterial infection.

DETAILED DESCRIPTION OF EMBODIMENTS

Figure 1A:
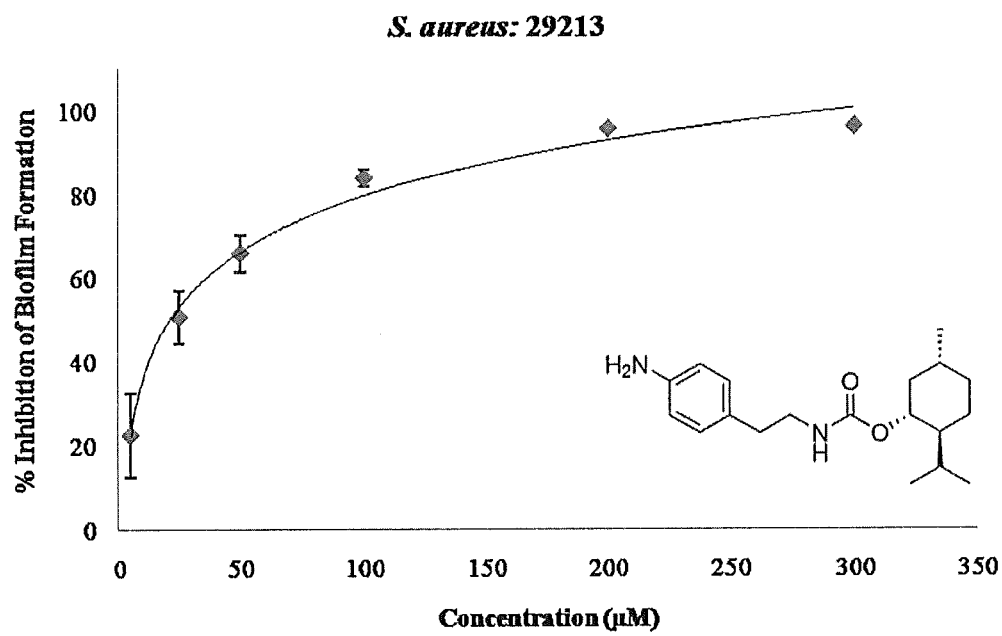
FIGS. 1A-1P illustrate the inhibitory effect of test compounds on *S. aureus*, MRSA, and *E. coli* biofilm formation.
Figure 1B:
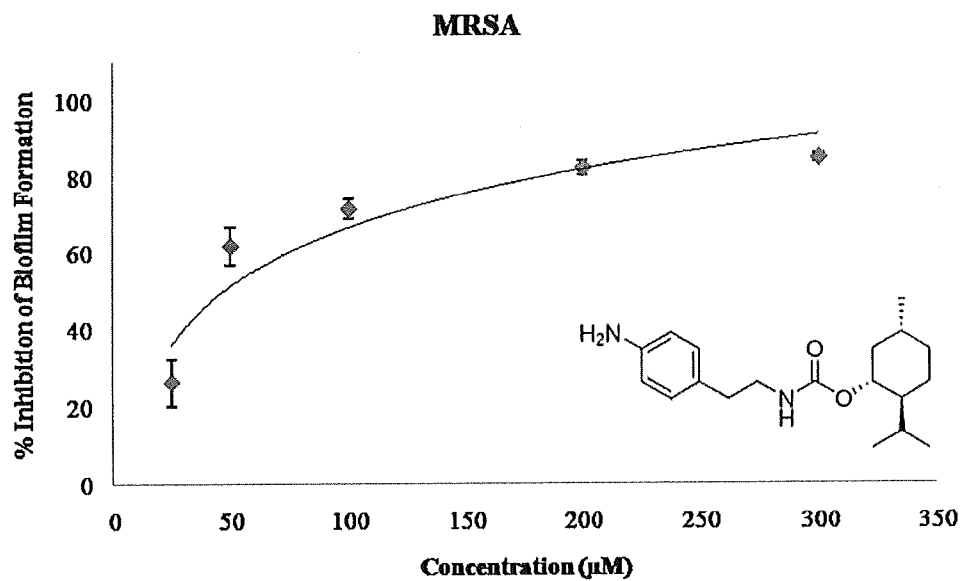
Figure 1C:
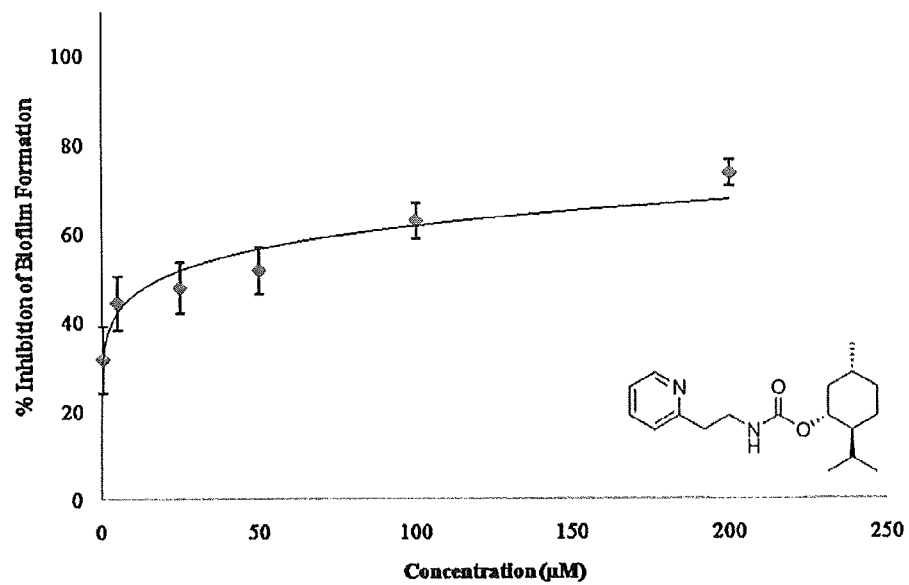
Figure 1D:
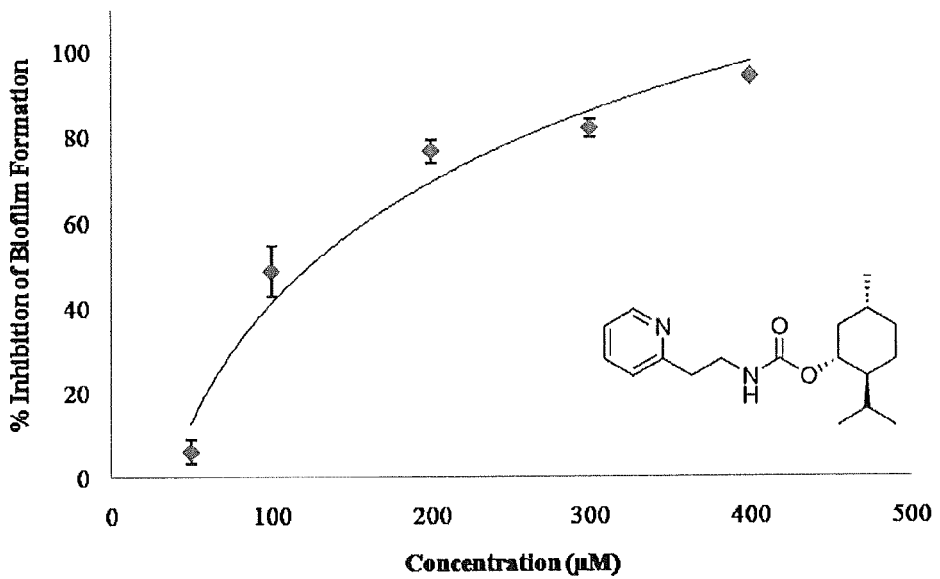
Figure 1E:
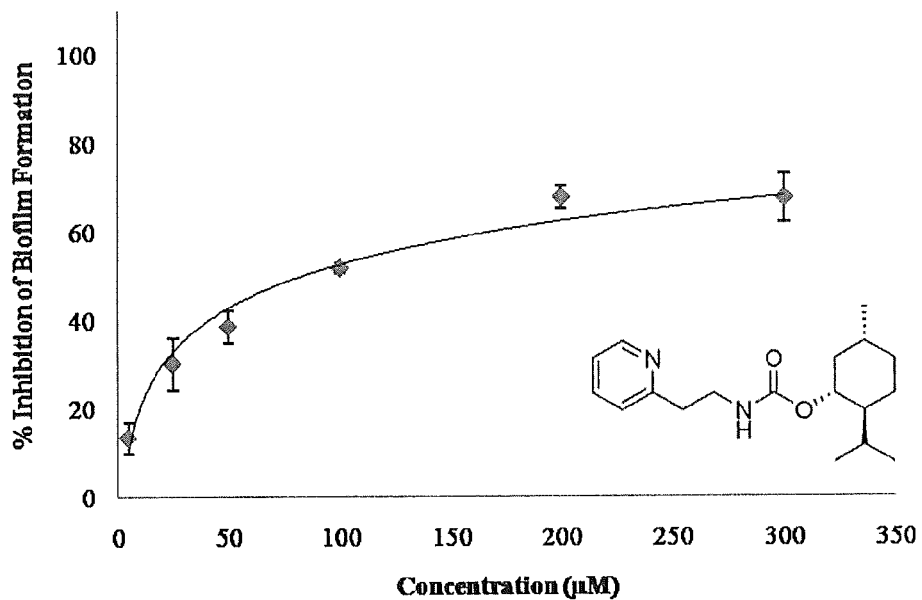
Figure 1F:
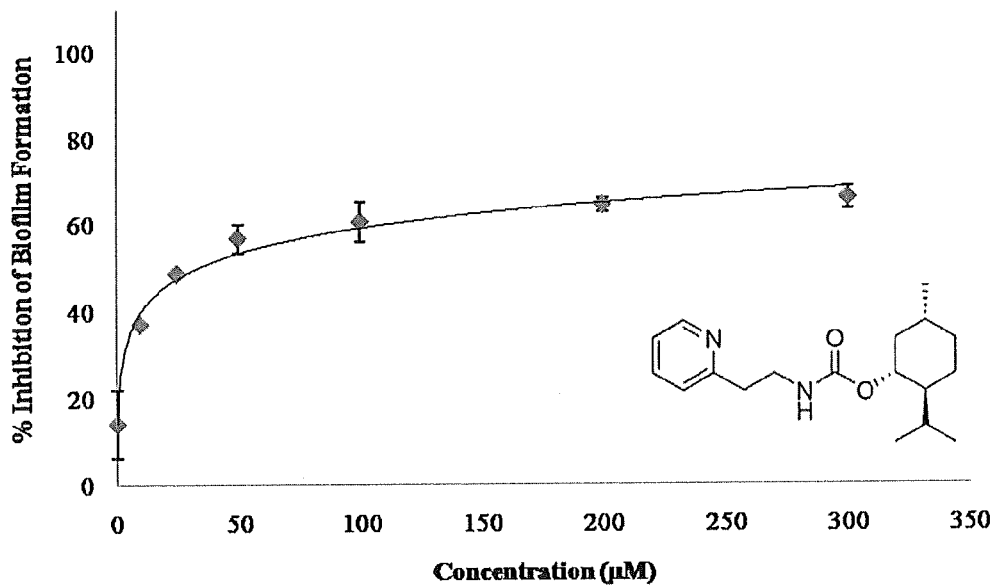
Figure 1G:
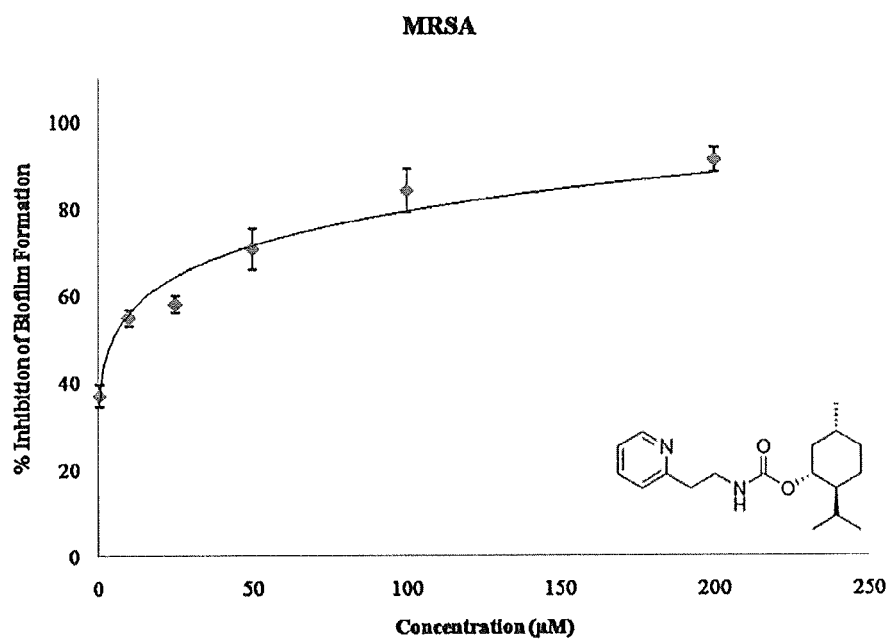
Figure 1H:
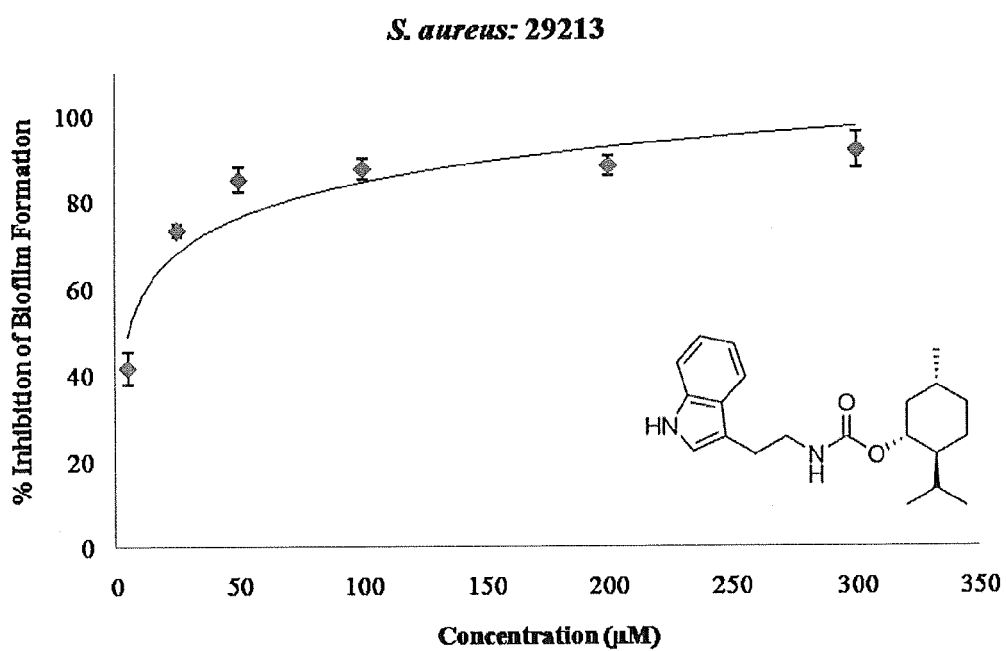
Figure 1I:
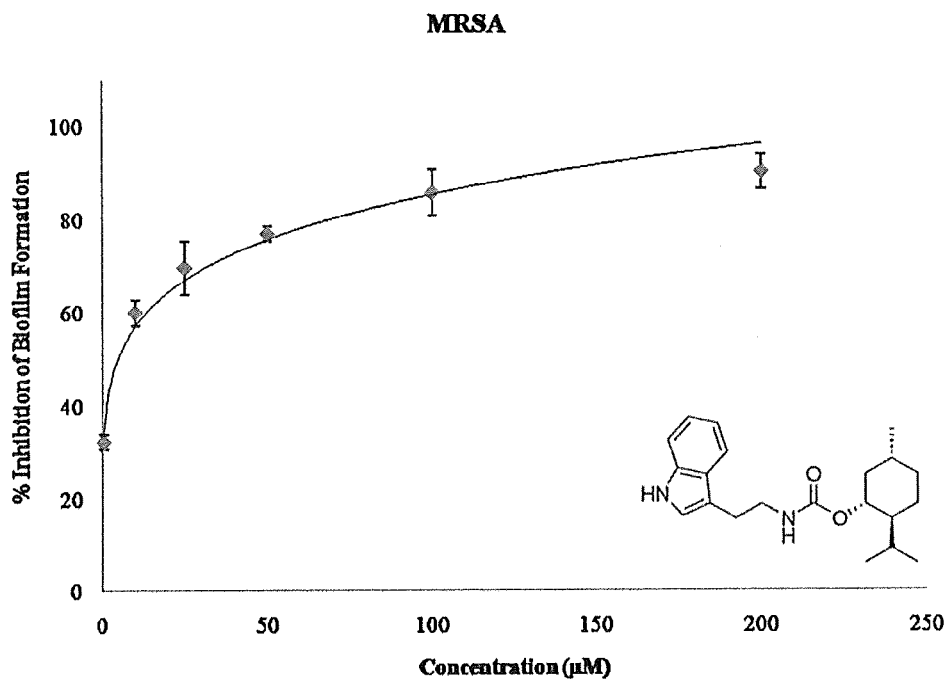
Figure 1J:
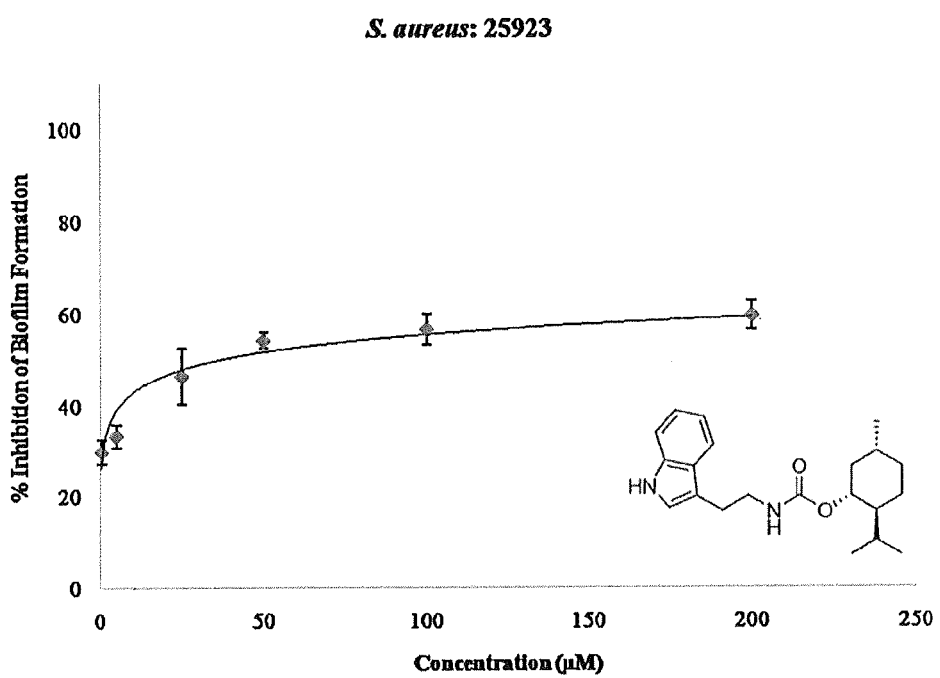
Figure 1K:
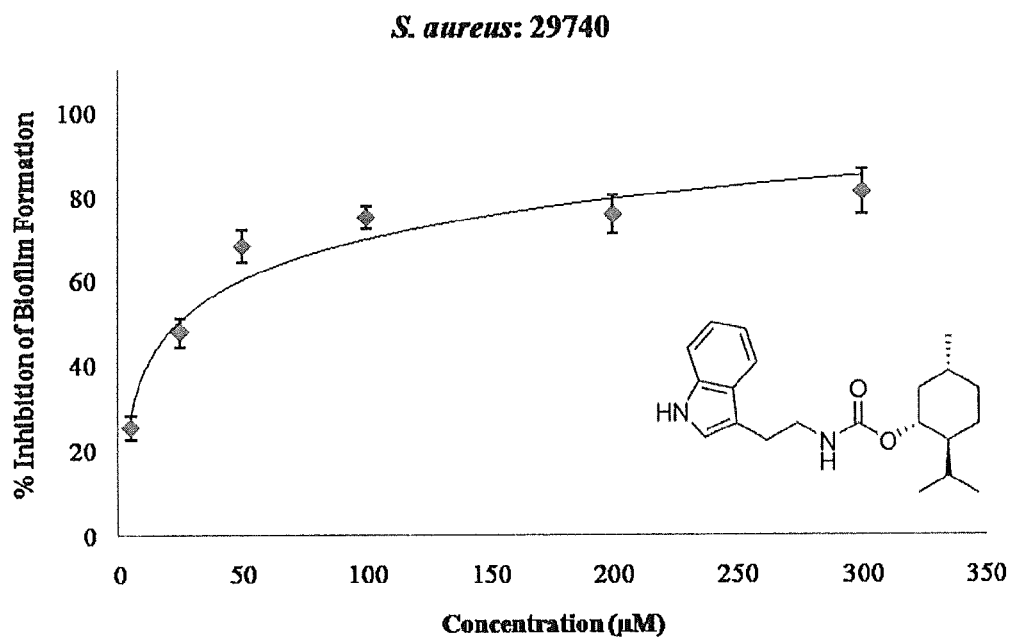
Figure 1L:
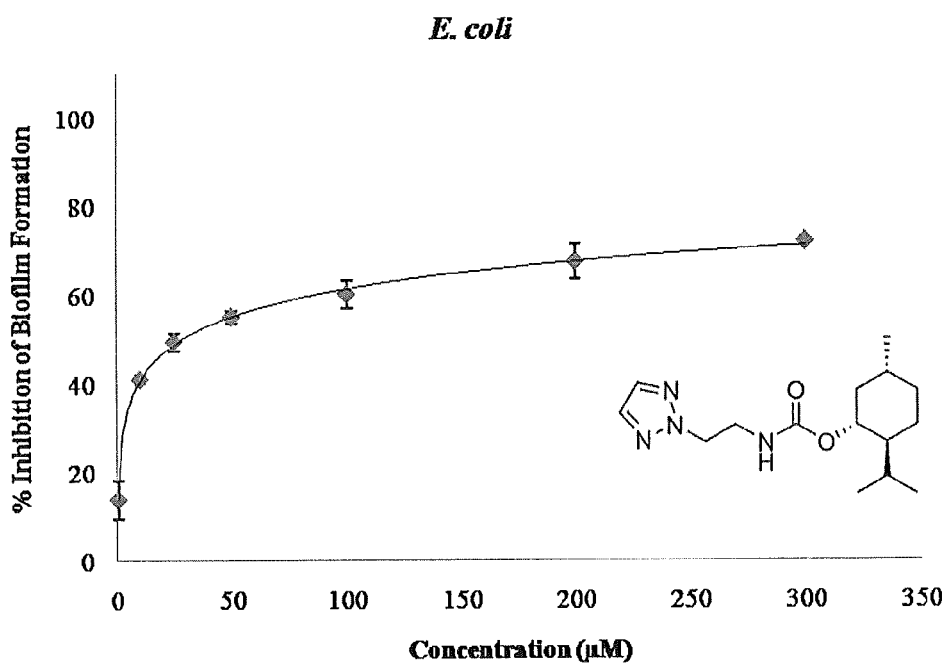
Figure 1M:
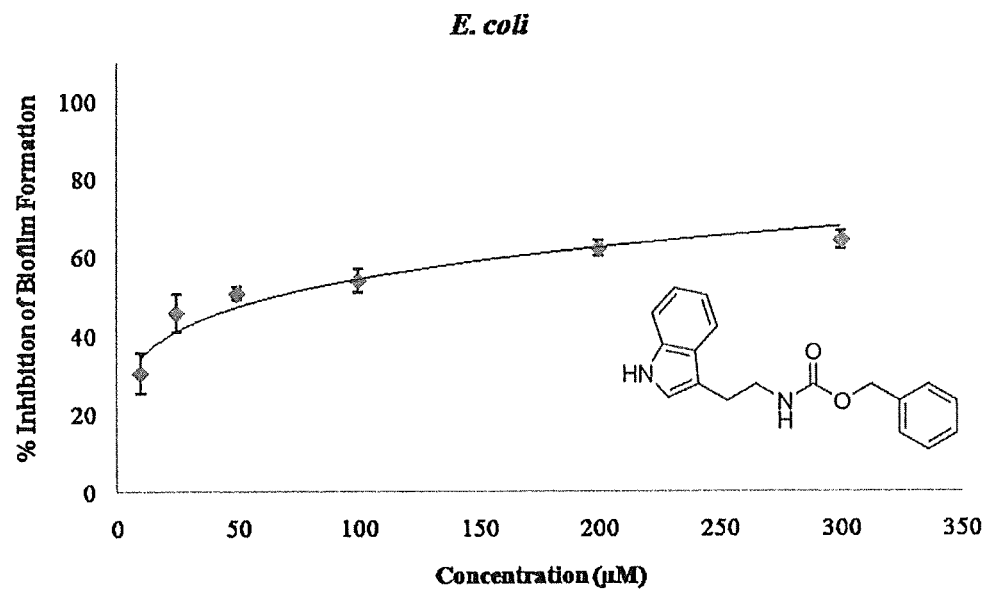
Figure 1N:
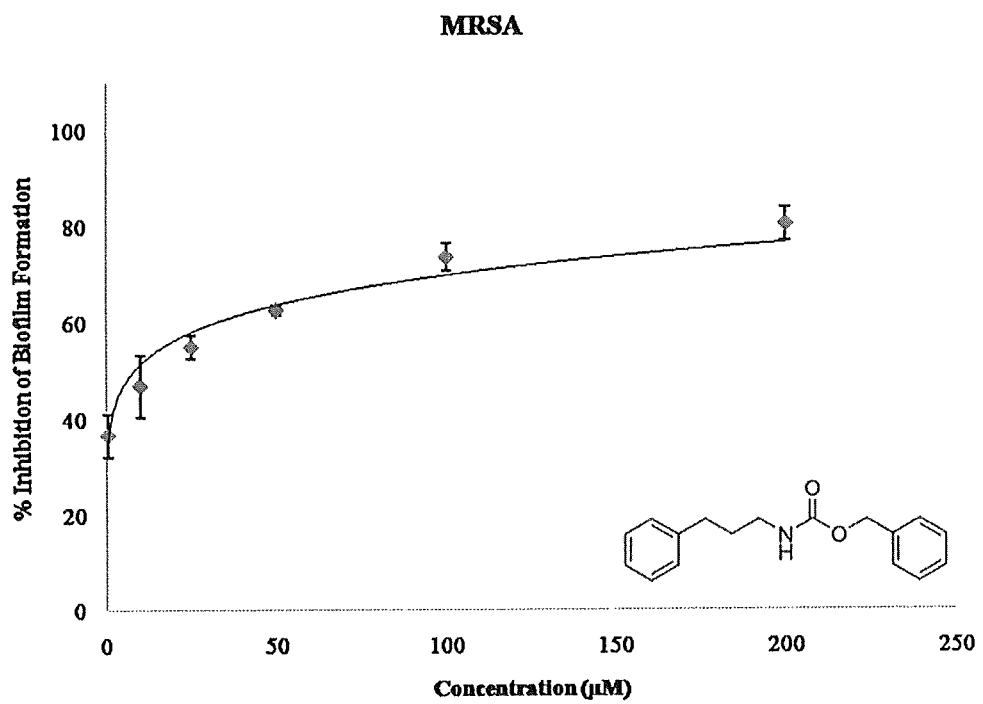
Figure 1O:
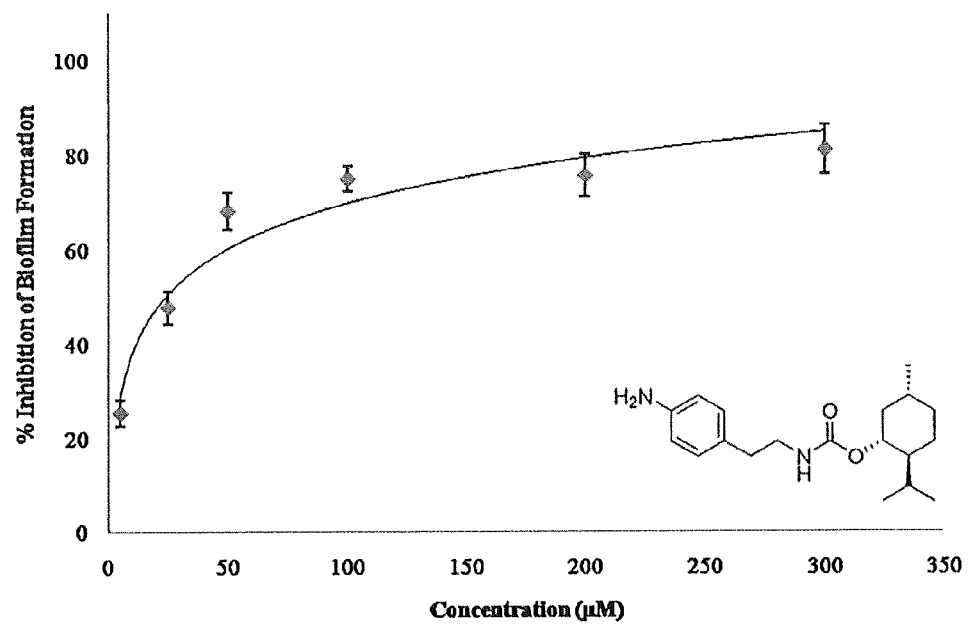
Figure 1P:
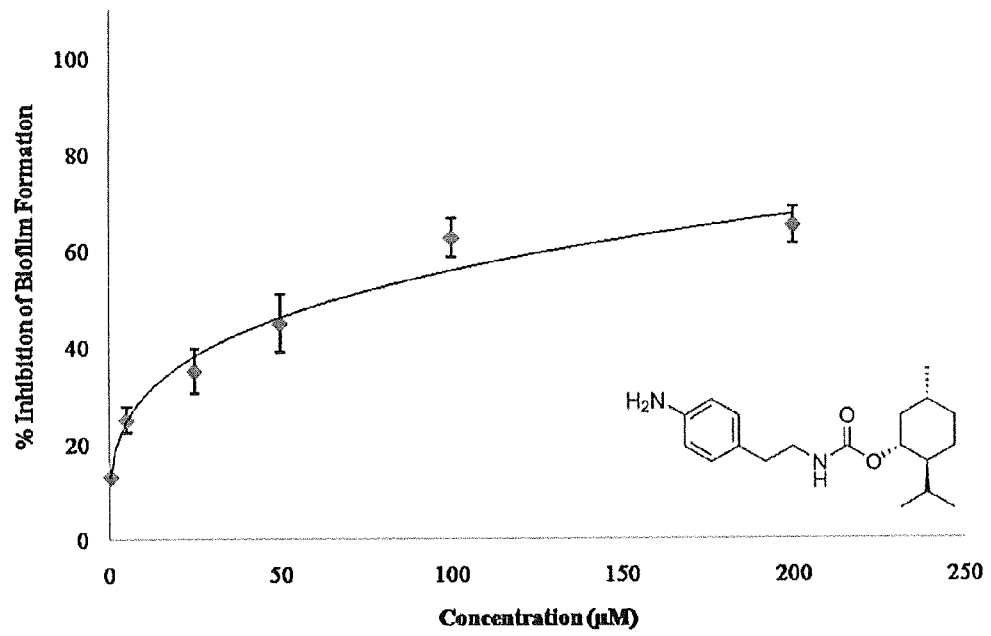

The present invention is further described below. All patent references referred to in this patent application are hereby incorporated by reference in their entirety as if set forth fully herein.

A. DEFINITIONS

"Carbamate" refers to the commonly known moiety:

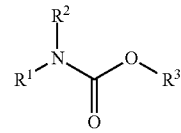

"H" refers to a hydrogen atom. "C" refers to a carbon atom. "N" refers to a nitrogen atom. "O" refers to an oxygen atom. "Halo" refers to F, Cl, Br or I. The term "hydroxy," as used herein, refers to an —OH moiety. "Br" refers to a bromine atom. "Cl" refers to a chlorine atom. "I" refers to an iodine atom. "F" refers to a fluorine atom.

An "acyl group" is intended to mean a group —C(O)—R, where R is a suitable substituent (for example, an acetyl group, a propionyl group, a butyroyl group, a benzoyl group, or an alkylbenzoyl group).

"Alkyl," as used herein, refers to a straight or branched chain hydrocarbon containing from 1 or 2 to 10 or 20 or more carbon atoms (e.g., C2, C3, C4, C5, C6, C7, C8, C9, C10, C11, C12, C13, C14, C15, etc.). In some embodiments the alkyl can be a lower alkyl. "Lower alkyl" refers to straight or branched chain alkyl having from 1 to 3, or from 1 to 5, or from 1 to 8 carbon atoms. Representative examples of alkyl include, but are not limited to, methyl, ethyl, n-propyl, iso-propyl, n-butyl, sec-butyl, iso-butyl, tert-butyl, n-pentyl, iso-pentyl, neopentyl, n-hexyl, 3-methylhexyl, 2,2-dimethylpentyl, 2,3-dimethylpentyl, n-heptyl, n-octyl, n-nonyl, n-decyl, and the like.

As generally understood by those of ordinary skill in the art, "saturation" refers to the state in which all available valence bonds of an atom (e.g., carbon) are attached to other atoms. Similarly, "unsaturation" refers to the state in which not all the available valence bonds are attached to other atoms; in such compounds the extra bonds usually take the form of double or triple bonds (usually with carbon). For example, a carbon chain is "saturated" when there are no double or triple bonds present along the chain or directly connected to the chain (e.g., a carbonyl), and is "unsaturated" when at least one double or triple bond is present along the chain or directly connected to the chain (e.g., a carbonyl). Further, the presence or absence of a substituent depending upon chain saturation will be understood by those of ordinary skill in the art to depend upon the valence requirement of the atom or atoms to which the substituent binds (e.g., carbon).

"Alkenyl," as used herein, refers to a straight or branched chain hydrocarbon containing from 1 or 2 to 10 or 20 or more carbons, and containing at least one carbon-carbon double bond, formed structurally, for example, by the replacement of two hydrogens. Representative examples of "alkenyl" include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl and the like.

"Alkynyl," as used herein, refers to a straight or branched chain hydrocarbon group containing from 1 or 2 to 10 or 20 or more carbon atoms, and containing at least one carbon-carbon triple bond. Representative examples of alkynyl include, but are not limited, to acetylenyl, 1-propynyl, 2-propynyl, 3-butynyl, 2-pentynyl, 1-butynyl and the like.

The term "cycloalkyl," as used herein, refers to a saturated cyclic hydrocarbon group containing from 3 to 8 carbons or more. Representative examples of cycloalkyl include, cyclopropyl, cyclobutyl, cyclopentyl, cyclohexyl, cycloheptyl, and cyclooctyl. In some embodiments, cycloalkyl groups as described herein are optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, etc.

As understood in the art, the term "optionally substituted" indicates that the specified group is either unsubstituted, or substituted by one or more suitable substituents. A "substituent" that is "substituted" is an atom or group which takes the place of a hydrogen atom on the parent chain or cycle of an organic molecule.

"Heterocyclo," as used herein, refers to a monocyclic, bicyclic or tricyclic ring system. Monocyclic heterocycle ring systems are exemplified by any 5 or 6 member ring containing 1, 2, 3, or 4 heteroatoms independently selected from the group consisting of: O, N, and S. The 5 member ring has from 0 to 2 double bonds, and the 6 member ring has from 0-3 double bonds. Representative examples of monocyclic ring systems include, but are not limited to, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholine sulfone, sulfoxide, thiopyran, triazine, triazole, trithiane, and the like. Bicyclic ring systems are exemplified by any of the above monocyclic ring systems fused to an aryl group as defined herein, a cycloalkyl group as defined herein, or another monocyclic ring system as defined herein. Representative examples of bicyclic ring systems include but are not limited to, for example, benzimidazole, benzothiazole, benzothiadiazole, benzothiophene, benzoxadiazole, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, pyranopyridine, quinoline, quinolizine, quinoxaline, quinazoline, tetrahydroisoquinoline, tetrahydroquinoline, thiopyranopyridine, and the like. In some embodiments, heterocyclo groups as described herein are optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, etc.

"Aryl" as used herein refers to a ring system having one or more aromatic rings. Representative examples of aryl include azulenyl, indanyl, indenyl, naphthyl, phenyl, tetrahydronaphthyl, and the like. The aryl groups of this invention can be substituted with 1, 2, 3, 4, or 5 substituents independently selected from alkenyl, alkenyloxy, alkoxy, alkoxyalkoxy, alkoxycarbonyl, alkyl, alkylcarbonyl, alkylcarbonyloxy, alkylsulfinyl, alkylsulfonyl, alkylthio, alkynyl, aryl, aryloxy, azido, arylalkoxy, arylalkyl, aryloxy, carboxy, cyano, formyl, halogen, haloalkyl, haloalkoxy, hydroxy, hydroxyalkyl, mercapto, nitro, sulfamyl, sulfo, sulfonate, —NR'R" (wherein, R' and R" are independently selected from hydrogen, alkyl, alkylcarbonyl, aryl, arylalkyl and formyl), and —C(O)NR'R" (wherein R' and R" are independently selected from hydrogen, alkyl, alkylcarbonyl, aryl, arylalkyl, and formyl).

"Heteroaryl" means a cyclic, aromatic hydrocarbon in which one or more carbon atoms have been replaced with heteroatoms (e.g., N, O or S). If the heteroaryl group contains more than one heteroatom, the heteroatoms may be the same or different. Examples of heteroaryl groups include pyridyl, pyrimidinyl, imidazolyl, thienyl, furyl, pyrazinyl, pyrrolyl, pyranyl, isobenzofuranyl, chromenyl, xanthenyl, indolyl, isoindolyl, indolizinyl, triazolyl, pyridazinyl, indazolyl, purinyl, quinolizinyl, isoquinolyl, quinolyl, phthalazinyl, naphthyridinyl, quinoxalinyl, isothiazolyl, and benzo[b]thienyl. Preferred heteroaryl groups are five and six membered rings and contain from one to three heteroatoms independently selected from the group consisting of: O, N, and S. The heteroaryl group, including each heteroatom, can be unsubstituted or substituted with from 1 to 4 suitable substituents, as chemically feasible. For example, the heteroatom S may be substituted with one or two oxo groups, which may be shown as =O.

"Alkoxy," as used herein, refers to an alkyl group, as defined herein, appended to the parent molecular moiety through an oxy group, as defined herein. Representative examples of alkoxy include, but are not limited to, methoxy, ethoxy, propoxy, 2-propoxy, butoxy, tert-butoxy, pentyloxy, hexyloxy and the like.

An "amine" or "amino" is intended to mean the group —NH$_2$.

An "amide" as used herein refers to an organic functional group having a carbonyl group (C=O) linked to a nitrogen atom (N), or a compound that contains this group, generally depicted as:

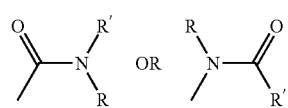

wherein, R and R' can independently be any covalently-linked atom or atoms.

A "thiol" or "mercapto" refers to an —SH group or to its tautomer =S.

A "sulfone" as used herein refers to a sulfonyl functional group, generally depicted as:

wherein, R can be any covalently-linked atom or atoms.

A "sulfoxide" as used herein refers to a sulfinyl functional group, generally depicted as:

wherein, R can be any covalently-linked atom or atoms.

The term "oxo," as used herein, refers to a =O moiety. The term "oxy," as used herein, refers to a —O— moiety.

"Nitro" refers to the organic compound functional group —NO$_2$.

"Carbonyl" is a functional group having a carbon atom double-bonded to an oxygen atom (—C=O). "Carboxy" as used herein refers to a —COOH functional group, also written as —CO$_2$H or —(C=O)—OH.

A "pharmaceutically acceptable salt" is intended to mean a salt that retains the biological effectiveness of the free acids and bases of a specified compound and that is not biologically or otherwise undesirable. Examples of pharmaceutically acceptable salts include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1, 4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycollates, tartrates, methanesulfonates, propanesulfonates, naphthalene-1-sulfonates, naphthalene-2-sulfonates, and mandelates.

A "prodrug" is intended to mean a compound that is converted under physiological conditions or by solvolysis or metabolically to a specified compound that is pharmaceutically active. A thorough discussion is provided in T. Higuchi and V. Stella, Prodrugs as Novel delivery Systems, Vol. 14 of the A.C.S. Symposium Series and in Edward B. Roche, ed., Bioreversible Carriers in Drug Design, American Pharmaceutical Association and Pergamon Press, 1987, both of which are incorporated by reference herein in their entirety.

B. ACTIVE COMPOUNDS

Active compounds are provided below. In some of the embodiments provided in the present invention, active compounds are carbamates. Active compounds as described herein can be prepared as detailed below or in accordance with known procedures or variations thereof that will be apparent to those skilled in the art.

As will be appreciated by those of skill in the art, the active compounds of the various formulas disclosed herein may contain chiral centers, e.g. asymmetric carbon atoms. Thus, the present invention is concerned with the synthesis of both: (i) racemic mixtures of the active compounds, and (ii) enantiomeric forms of the active compounds. The resolution of racemates into enantiomeric forms can be done in accordance with known procedures in the art. For example, the racemate may be converted with an optically active reagent into a diastereomeric pair, and the diastereomeric pair subsequently separated into the enantiomeric forms.

Geometric isomers of double bonds and the like may also be present in the compounds disclosed herein, and all such stable isomers are included within the present invention unless otherwise specified. Also included in active compounds of the invention are tautomers (e.g., tautomers of triazole and/or imidazole) and rotamers. All chains defined by the formulas herein which include three or more carbons may be saturated or unsaturated unless otherwise indicated.

Provided herein are active compounds of Formula (I):

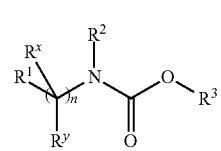

(I)

wherein:

$R^1$ is an aryl, an amine-substituted aryl, or $R^1$ is a heteroaryl having at least one nitrogen atom;

n=0 to 10, saturated or unsaturated;

each occurrence of $R^x$ and $R^y$ is present or absent (depending upon chain saturation), and is each independently H or alkyl;

$R^2$ is selected from the group consisting of: H, alkyl, alkenyl and alkynyl; and $R^3$ is alkyl, substituted cycloalkyl or unsubstituted cycloalkyl, or a pharmaceutically acceptable salt or prodrug thereof.

In some embodiments, $R^1$ is an amine-substituted aryl, or $R^1$ is a heteroaryl having at least one nitrogen atom.

In some embodiments, $R^3$ is substituted or unsubstituted cycloalkyl.

In some embodiments of Formula (I), $R^3$ is a substituted cycloalkyl represented by Formula (I)(a):

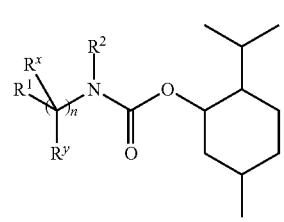

(I)(a)

wherein:

$R^1$ is an amine-substituted aryl, or $R^1$ is a heteroaryl having at least one nitrogen atom;

n=0 to 10, saturated or unsaturated;

each occurrence of $R^x$ and $R^y$ is present or absent (depending upon chain saturation), and is each independently H or alkyl; and $R^2$ is selected from the group consisting of: H, alkyl, alkenyl and alkynyl, or a pharmaceutically acceptable salt or prodrug thereof.

In some embodiments of Formula (I) and Formula (I)(a), $R^1$ is a group:

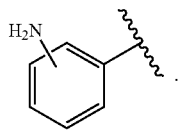

In some embodiments of Formula (I) and Formula (I)(a), $R^1$ is a heteroaryl having at least one nitrogen atom. Examples include, but are not limited to:

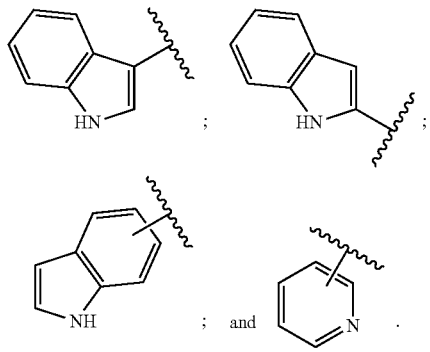

In some embodiments of Formula (I)(a), $R^1$ is an amine-substituted aryl represented by Formula (I)(a)(i):

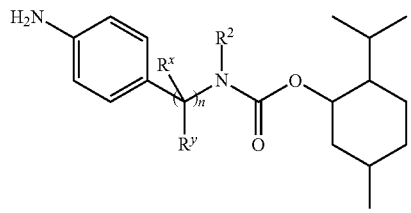

(I)(a)(i)

wherein:
n=0 to 10, saturated or unsaturated;
each occurrence of $R^x$ and $R^y$ is present or absent (depending upon chain saturation), and is each independently H or alkyl; and
$R^2$ is selected from the group consisting of: H, alkyl, alkenyl and alkynyl,
or a pharmaceutically acceptable salt or prodrug thereof.
In some embodiments of Formula (I)(a), $R^1$ is heteroaryl having at least one nitrogen represented by Formula (I)(a)(ii):

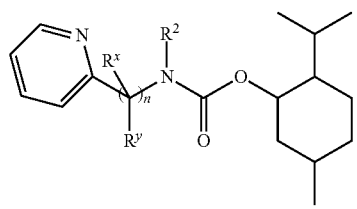

(I)(a)(ii)

wherein:
n=0 to 10, saturated or unsaturated;
each occurrence of $R^x$ and $R^y$ is present or absent (depending upon chain saturation), and is each independently H or alkyl; and
$R^2$ is selected from the group consisting of: H, alkyl, alkenyl and alkynyl,
or a pharmaceutically acceptable salt or prodrug thereof.

In some embodiments of Formula (I)(a), $R^1$ is heteroaryl having at least one nitrogen represented by Formula (I)(a)(iii):

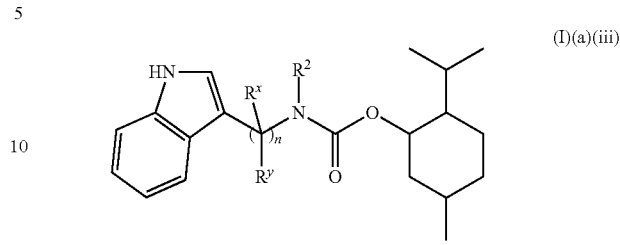

(I)(a)(iii)

wherein:
n=0 to 10, saturated or unsaturated;
each occurrence of $R^x$ and $R^y$ is present or absent (depending upon chain saturation), and is each independently H or alkyl; and
$R^2$ is selected from the group consisting of: H, alkyl, alkenyl and alkynyl,
or a pharmaceutically acceptable salt or prodrug thereof.
Exemplary compounds of Formula (I)(a) are given below, in which $R^1$ is heteroaryl, or aryl substituted with amino; n=2, saturated, $R^x$ and $R^y$ are each H, $R^2$ is H, and $R^3$ is substituted cycloalkyl.

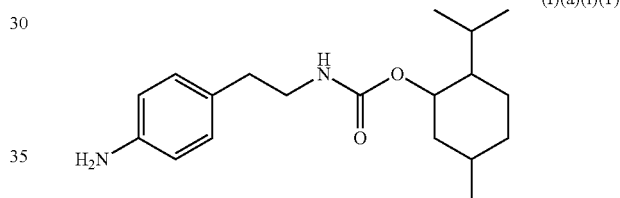

(I)(a)(i)(1)

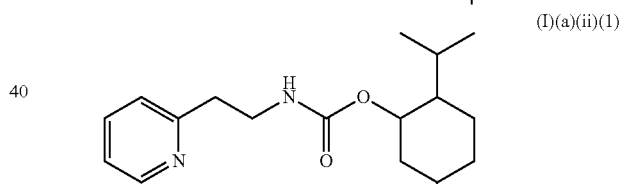

(I)(a)(ii)(1)

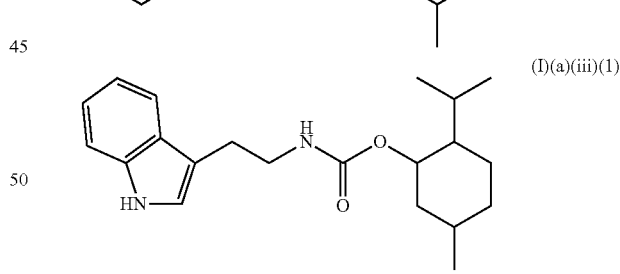

(I)(a)(iii)(1)

Also provided is a pharmaceutically acceptable salt or prodrug thereof of each of the compounds represented by the Formulas described above. Each of the Formulas provided herein may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, etc., as desired.

C. COMPOSITIONS

In some embodiments, biofilm inhibiting compositions are provided, comprising a carrier and an effective amount of active compound. "Biofilm" or "biofilms" refer to communities of microorganisms that are attached to a substrate. The microorganisms often excrete a protective and adhesive matrix of polymeric compounds. They often have structural heterogeneity, genetic diversity, and complex community interactions. "Biofilm inhibiting", "biofilm reducing", "biofilm resistant", "biofilm controlling" or "antifouling" refer to inhibition of the establishment or growth of a biofilm, or decrease in the amount of organisms that attach and/or grow upon a substrate. As used herein, a "substrate" can include any living or nonliving structure. For example, biofilms often grow on synthetic materials submerged in an aqueous solution or exposed to humid air, but they also can form as floating mats on a liquid surface, in which case the microorganisms are adhering to each other or to the adhesive matrix characteristic of a biofilm.

An "effective amount" of a biofilm inhibiting composition is that amount which is necessary to carry out the composition's function of inhibiting a biofilm.

In some embodiments, the carrier is a pharmaceutically acceptable carrier. A "pharmaceutically acceptable carrier" as used herein refers to a carrier that, when combined with an active compound of the present invention, facilitates the application or administration of that active compound for its intended purpose to prevent or inhibit biofilm formation, or remove an existing biofilm. The active compounds may be formulated for administration in a pharmaceutically acceptable carrier in accordance with known techniques. See, e.g., Remington, *The Science And Practice of Pharmacy* ($9^{th}$ Ed. 1995). The pharmaceutically acceptable carrier must, of course, also be acceptable in the sense of being compatible with any other ingredients in the composition. The carrier may be a solid or a liquid, or both, and is preferably formulated with the compound as a unit-dose composition, for example, a tablet, which may contain from 0.01 or 0.5% to 95% or 99% by weight of the active compound. One or more active compounds may be included in the compositions of the invention, which may be prepared by any of the well-known techniques of pharmacy comprising admixing the components, optionally including one or more accessory ingredients.

In general, compositions may be prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

The compositions of the invention include those suitable for oral, rectal, topical, buccal (e.g., sub-lingual), vaginal, parenteral (e.g., subcutaneous, intramuscular, intradermal, or intravenous), topical (i.e., both skin and mucosal surfaces, including airway surfaces) and transdermal administration, although the most suitable route in any given case will depend on the nature and severity of the condition being treated and on the nature of the particular active compound that is being used. Routes of parenteral administration include intrathecal injection and intraventricular injection into a ventricle of the brain.

Compositions suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such compositions may be prepared by any suitable method of pharmacy, which includes the step of bringing into association the active compound and a suitable carrier (which may contain one or more accessory ingredients as noted above).

Compositions suitable for buccal (sub-lingual) administration include lozenges comprising the active compound in a flavored base, usually sucrose and acacia or tragacanth; and pastilles comprising the compound in an inert base such as gelatin and glycerin or sucrose and acacia.

Compositions of the present invention suitable for parenteral administration comprise sterile aqueous and non-aqueous injection solutions of the active compound, which preparations are preferably isotonic with the blood of the intended recipient. These preparations may contain anti-oxidants, buffers, bacteriostats and solutes that render the composition isotonic with the blood of the intended recipient. Aqueous and non-aqueous sterile suspensions may include suspending agents and thickening agents. The compositions may be presented in unit/dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described.

For example, in one aspect of the present invention, there is provided an injectable, stable, sterile composition comprising an active compound as described herein, or a salt or prodrug thereof, in a unit dosage form in a sealed container. The compound or salt is provided in the form of a lyophilizate that is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent that is physiologically acceptable may be employed in sufficient quantity to emulsify the compound or salt in an aqueous carrier. One such useful emulsifying agent is phosphatidyl choline.

Compositions suitable for rectal administration are preferably presented as unit dose suppositories. These may be prepared by mixing the active compound with one or more conventional solid carriers, for example, cocoa butter, and then shaping the resulting mixture.

Compositions suitable for topical application to the skin preferably take the form of an ointment, cream, lotion, paste, gel, spray, aerosol, or oil. Carriers that may be used include petroleum jelly, lanoline, polyethylene glycols, alcohols, transdermal enhancers, and combinations of two or more thereof.

Compositions suitable for transdermal administration may be presented as discrete patches adapted to remain in intimate contact with the epidermis of the recipient for a prolonged period of time. Compositions suitable for transdermal administration may also be delivered by iontophoresis (see, for example, *Pharmaceutical Research* 3 (6):318 (1986)) and typically take the form of an optionally buffered aqueous solution of the active compound.

Also provided in some embodiments are compositions comprising an active compound and a biocide. A "biocide" as used herein refers to a substance with the ability to kill or to inhibit the growth of microorganisms (e.g., bacteria, fungal cells, protozoa, etc.), which substance is not an active compound give above in Section B. Common biocides include oxidizing and non-oxidizing chemicals. Examples of oxidizing biocides include chlorine, chlorine dioxide, and ozone. Examples of non-oxidizing biocides include quaternary ammonium compounds, formaldehyde, and anionic and non-anionic surface agents. Chlorine is the most common biocide used in sanitizing water systems.

An "antibiotic" as used herein is a type of "biocide." Common antibiotics include aminoglycosides, carbacephems (e.g., loracarbef), carbapenems, cephalosporins, glycopeptides (e.g., teicoplanin and vancomycin), macrolides, monobactams (e.g., aztreonam) penicillins, polypeptides (e.g., bacitracin, colistin, polymyxin B), quinolones, sulfonamides, tetracyclines, etc. Antibiotics treat infections by either killing or preventing the growth of microorganisms. Many act to inhibit cell wall synthesis or other vital protein synthesis of the microorganisms.

Aminoglycosides are commonly used to treat infections caused by Gram-negative bacteria such as *Escherichia coli* and *Klebsiella*, particularly *Pseudomonas aeroginosa*. Examples of aminoglycosides include, but are not limited to amikacin, gentamicin, kanamycin, neomycin, netilmicin, streptomycin, tobramycin, and paromomycin.

Carbapenems are broad-spectrum antibiotics, and include, but are not limited to, ertapenem, doripenem, imipenem/cilstatin, and meropenem.

Cephalosporins include, but are not limited to, cefadroxil, cefazolin, cefalotin (cefalothin), cefalexin, cefaclor, cefamandole, cefoxitin, cefprozil, loracarbef, cefuroxime, cefixime, cefdinir, cefditoren, cefoperazone, cefotaxime, cefpodoxime, ceftazidime, ceftibuten, ceftizoxime, ceftriaxone, cefepime, cefpirome, and ceftobiprole.

Macrolides include, but are not limited to, azithromycin, clarithromycin, dirithromycin, erythromycin, roxithromycin, troleandomycin, telithromycin and spectinomycin.

Penicillins include, but are not limited to, amoxicillin, ampicillin, azlocillin, bacampicillin, carbenicillin, cloxacillin, dicloxacillin, flucloxacillin, mezlocillin, meticillin, nafcillin, oxacillin, penicillin, piperacillin and ticarcillin.

Quinolones include, but are not limited to, ciprofloxacin, enoxacin, gatifloxacin, gemifloxacin, levofloxacin, lomefloxacin, moxifloxacin, norfloxacin, ofloxacin and trovafloxacin.

Sulfonamides include, but are not limited to, mafenide, prontosil, sulfacetamide, sulfamethizole, sulfanilamide, sulfasalazine, sulfisoxazole, trimethoprim, and co-trimoxazole (trimethoprim-sulfamethoxazole).

Tetracyclines include, but are not limited to, demeclocycline, doxycycline, minocycline, oxytetracycline and tetracycline.

Other antibiotics include arsphenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinupristin/dalfopristin, rifampin (rifampicin), timidazole, etc.

In some embodiments, a dentifrice composition is provided comprising the active compounds. A "dentifrice" is a substance that is used to clean the teeth. It may be in the form of, e.g., a paste or powder. Commonly known dentifrices include toothpaste, mouthwash, chewing gum, dental floss, and dental cream. Other examples of dentifrices include toothpowder, mouth detergent, troches, dental or gingival massage cream, dental strips, dental gels, and gargle tablets. Examples of dentifrice compositions comprising toothpaste and mouthwash are found in U.S. Pat. No. 6,861,048 (Yu et al.); U.S. Pat. No. 6,231,836 (Taldkhtalian et al.); and U.S. Pat. No. 6,331,291 (Glace et al.); each incorporated by reference herein in their entirety.

A coating composition is also provided. A "coating" as used herein is generally known. Any of a variety of organic and aqueous coating compositions, with or without pigments, may be modified to contain biofilm inhibiting compositions as described herein, including but not limited to those described in U.S. Pat. Nos. 7,109,262, 6,964,989, 6,835,459, 6,677,035, 6,528,580, 6,235,812, etc., each incorporated by reference herein in their entirety.

In general, the coatings comprise a film-forming resin, an aqueous or organic solvent that disperses the resin; and, optionally, at least one pigment. Other ingredients such as colorants, secondary pigments, stabilizers and the like can be included if desired. However, for use in the present invention the compositions further comprise one or more biofilm inhibiting compounds as described herein, which may be carried by or dispersed in the solvent and/or resin, so that the biofilm inhibiting compounds are dispersed or distributed on the substrate an article coated. A resin may carry the biofilm inhibiting compounds through covalent attachment through means well known in the art. The resin may comprise, for example, a polymeric material. A polymeric material is a material that is comprised of large molecules made from associated smaller repeating structural units, often covalently linked. Common examples of polymeric materials are unsaturated polyester resins, and epoxy resins.

Any suitable article can be coated, in whole or in part, with a composition of the invention. Suitable articles include, but are not limited to, automobiles and airplanes (including substrates such as wing and propeller surfaces for aerodynamic testing), boat vessel hulls (including interior and exterior surfaces thereof), pressure vessels (including interior and exterior surfaces thereof) medical implants, windmills, etc. Coating of the article with the composition can be carried out by any suitable means, such as by brushing, spraying, electrostatic deposition, dip coating, doctor blading, etc.

D. METHODS OF USE

Methods of controlling biofilm formation on a substrate are disclosed, comprising the step of administering an active compound to a substrate in an amount effective to inhibit biofilm formation. A "substrate" as used herein is a base on which an organism, such as those commonly found in biofilms, may live. The term "substrate," as used herein, refers to any substrate, whether in an industrial or a medical setting, that provides or can provide an interface between an object and a fluid, permitting at least intermittent contact between the object and the fluid. A substrate, as understood herein, further provides a plane whose mechanical structure, without further treatment, is compatible with the adherence of microorganisms. Substrates compatible with biofilm formation may be natural or synthetic, and may be smooth or irregular. Fluids contacting the substrates can be stagnant or flowing, and can flow intermittently or continuously, with laminar or turbulent or mixed flows. A substrate upon which a biofilm forms can be dry at times with sporadic fluid contact, or can have any degree of fluid exposure including total immersion. Fluid contact with the substrate can take place via aerosols or other means for air-borne fluid transmission.

Biofilm formation with health implications can involve those substrates in all health-related environments, including substrates found in medical environments and those substrates in industrial or residential environments that are involved in those functions essential to human well being, for example, nutrition, sanitation and the prevention of disease. Substrates found in medical environments include the inner and outer aspects of various instruments and devices, whether disposable or intended for repeated uses. Examples include the entire spectrum of articles adapted for medical use, including scalpels, needles, scissors and other devices used in invasive surgical, therapeutic or diagnostic procedures; implantable medical devices, including artificial blood vessels, catheters and other devices for the removal or delivery of fluids to patients, artificial hearts, artificial kidneys, orthopedic pins, plates and implants; catheters and other tubes (including urological and biliary tubes, endotracheal tubes, peripherably insertable central venous catheters, dialysis catheters, long term tunneled central venous catheters, peripheral venous catheters, short term central venous catheters, arterial catheters, pulmonary catheters, Swan-Ganz catheters, urinary catheters, peritoneal catheters), urinary devices (including long term urinary devices, tissue bonding urinary devices, artificial urinary sphincters, urinary dilators), shunts (including ventricular or arterio-venous shunts); prostheses (including breast implants, penile prostheses, vascular grafting prostheses, heart valves, artificial joints, artificial larynxes, otological implants), vascular catheter ports, wound drain tubes, hydrocephalus shunts, pacemakers and implantable defibrillators, and the like. Other examples will be readily apparent to practitioners in these arts. Substrates found in the medical environment also include the inner and outer aspects of pieces of medical equipment, medical gear worn or carried by personnel in the health care setting. Such substrates can include counter tops and fixtures in areas used for medical procedures or for preparing medical apparatus, tubes and canisters used in respiratory treatments, including the administration of oxygen, of solubilized drugs in nebulizers and of anesthetic agents. Also included are those substrates intended as biological barriers to infectious organisms in medical settings, such as gloves, aprons and faceshields. Commonly used materials for biological barriers may be latex-based or non-latex based. Vinyl is commonly used as a material for non-latex surgical gloves. Other such substrates can include handles and cables for medical or dental equipment not intended to be sterile. Additionally, such substrates can include those non-sterile external substrates of tubes and other apparatus found in areas where blood or body fluids or other hazardous biomaterials are commonly encountered.

Substrates in contact with liquids are particularly prone to biofilm formation. As an example, those reservoirs and tubes used for delivering humidified oxygen to patients can bear biofilms inhabited by infectious agents. Dental unit waterlines similarly can bear biofilms on their substrates, providing a reservoir for continuing contamination of the system of flowing an aerosolized water used in dentistry. Sprays, aerosols and nebulizers are highly effective in disseminating biofilm fragments to a potential host or to another environmental site. It is especially important to health to prevent biofilm formation on those substrates from where biofilm fragments can be carried away by sprays, aerosols or nebulizers contacting the substrate.

Other substrates related to health include the inner and outer aspects of those articles involved in water purification, water storage and water delivery, and articles involved in food processing. Substrates related to health can also include the inner and outer aspects of those household articles involved in providing for nutrition, sanitation or disease prevention. Examples can include food processing equipment for home use, materials for infant care, tampons and toilet bowls. "Substrate" as used herein also refers to a living substrate, such as the inner ear of a patient.

Substrates can be smooth or porous, soft or hard. Substrates can include a drainpipe, glaze ceramic, porcelain, glass, metal, wood, chrome, plastic (e.g., thermoplastic such as polyethylene, polypropylene, polystyrene, polyvinyl chloride or polytetrafluoroethylene (PTFE); thermosetting polymer, etc.) or other polymeric material, vinyl, and laminates thereof such as Formica® brand laminate, or any other material that may regularly come in contact with an aqueous solution in which biofilms may form and grow. The substrate can be a substrate commonly found on household items such as shower curtains or liners, upholstery, laundry, and carpeting.

A substrate on which biofilm inhibiting is important is that of a ship hull. Biofilms, such as those of *Halomonas pacifica*, promote the corrosion of the hull of ships and also increase the roughness of the hull, increasing the drag on the ship and thereby increasing fuel costs. The biofilm can also promote the attachment of larger living structures such as barnacles on the ship hull. Fuel can account for half of the cost of marine shipping, and the loss in fuel efficiency due to biofilm formation is substantial.

Substrates on which biofilms can adhere include those of living organisms, as in the case of humans with chronic infections caused by biofilms, as discussed above. Biofilms can also form on the substrates of food contact surfaces, such as those used for processing seafood, and also on food products themselves. Examples of seafood products that may have biofilm contamination include oysters. Human infections caused by the ingestion of raw oysters has been linked to *Vibrio vulnificus* bacterium. *Vibrio* bacteria attach to algae and plankton in the water and transfer to the oysters and fish that feed on these organisms.

Other examples of substrates or devices on which biofilms can adhere can be found in U.S. Pat. Nos. 5,814,668 and 7,087,661; and U.S. Pat. Appln. Publication Nos. 2006/0228384 and 2006/0018945, each of which is incorporated herein by reference in its entirety.

In some embodiments, methods of enhancing the effects of a biocide are disclosed, comprising the step of administering an active compound in combination with a biocide, the active compound being administered in an amount effective to enhance the effects of the biocide.

"Administering" or "administration of" an active compound and/or biocide as used herein in inclusive of contacting, applying, etc. (e.g., contacting with an aqueous solution, contacting with a surface (e.g., a hospital surface such as a table, instrumentation, etc.)), in addition to providing to a subject (for example, to a human subject in need of treatment for a microbial infection).

"Enhancing" the effects of a biocide by administering an active compound in combination with the biocide refers to increasing the effectiveness of the biocide, such that the microorganism killing and/or growth inhibition is higher at a certain concentration of the biocide administered in combination with the active compound than without. In some embodiments, a bacteria or other microorganism is "sensitized" to the effects of a biocide, such that the bacteria or other microorganism that was resistant to the biocide prior to administering the active compound (e.g., little to none, or less than 20, 10, 5 or 1% are killed upon application) is rendered vulnerable to that biocide upon or after administering the active compound (e.g., greater than 20, 30, 40, 50, 60, 70, 80, 90, or 95% or more are killed).

As used herein, the administration of two or more compounds (inclusive of active compounds and biocides) "in combination" means that the two compounds are administered closely enough in time that the administration of or presence of one alters the biological effects of the other. The two compounds may be administered simultaneously (concurrently) or sequentially.

Simultaneous administration of the compounds may be carried out by mixing the compounds prior to administration, or by administering the compounds at the same point in time but at different anatomic sites or using different routes of administration, or administered at times sufficiently close that the results observed are indistinguishable from those achieved when the compounds are administered at the same point in time.

Sequential administration of the compounds may be carried out by administering, e.g., an active compound at some point in time prior to administration of a biocide, such that the prior administration of active compound enhances the effects of the biocide (e.g., percentage of microorganisms killed and/or slowing the growth of microorganisms). In some embodiments, an active compound is administered at some point in time prior to the initial administration of a biocide. Alternatively, the biocide may be administered at some point in time prior to the administration of an active compound, and optionally, administered again at some point in time after the administration of an active compound.

Also disclosed is a method of controlling biofilm formation wherein the biofilm comprises Gram-negative or Gram-positive bacteria.

"Gram-negative" bacteria are those that do not retain crystal violet dye after an alcohol wash in the Gram staining protocol, while "Gram-positive" bacteria are those that are stained dark blue or violet color after an alcohol wash in the Gram staining protocol. This is due to structural properties in the cell walls of the bacteria. Gram-positive bacterial retain the crystal violet color due to a high amount of peptidoglycan in the cell wall.

Many genera and species of Gram-negative and Gram-positive bacteria are pathogenic. A "genus" is a category of biological classification ranking between the family and the species, comprising structurally or phylogenetically related species, or an isolated species exhibiting unusual differentiation. It is usually designated by a Latin or latinized capitalized singular noun. Examples of genera of biofilm-forming bacteria affected by active compounds of this invention include, but are not limited to, *Pseudomonas, Bordetella, Vibrio, Haemophilus, Halomonas*, and *Acinetobacter.*

"Species" refer to a category of biological classification ranking below the genus, and comprise members that are structurally or phylogenetically related, or an isolated member exhibiting unusual differentiation. Species are commonly designated by a two-part name, which name includes the capitalized and italicized name of the genus in which the species belongs as the first word in the name, followed by the second word that more specifically identifies the member of the genus, which is not capitalized. Examples of species of bacteria capable of forming biofilms that are affected by active compounds of the present invention include *Pseudomonas aeuroginosa, Bordetella bronchiseptica, Bordetella pertussis, Staphylococcus aureus, Vibrio vulnificus, Haemophilus influenzae, Halomonas pacifica*, and *Acinetobacter baumannii.*

Gram-negative bacteria include members of the phylum proteobacteria, which include genus members *Escherichia, Salmonella, Vibrio*, and *Helicobacter.*

Other examples of Gram-negative bacteria include, but are not limited to, bacteria of the genera *Klebsiella, Proteus, Neisseria, Helicobacter, Brucella, Legionella, Campylobacter, Francisella, Pasteurella, Yersinia, Bartonella, Bacteroides, Streptobacillus, Spirillum, Moraxella* and *Shigella.*

Examples of Gram-positive bacteria include, but are not limited to, bacteria of the genera *Listeria, Staphylococcus, Streptococcus, Bacillus, Corynebacterium, Enterococcus, Peptostreptococcus*, and *Clostridium*. Examples include, but are not limited to, *Listeria monocytogenes, Staphylococcus aureus* (including methicillin-resistant *S. aureus*, or MSRA), *Staphylococcus epidermidis, Streptococcus pyogenes, Streptococcus pneumoniae, Bacillus cereus, Bacillus anthracis, Clostridium botulinum, Clostridium perfringens, Clostridium difficile, Clostridium tetani, Corynebacterium diphtheriae, Corynebacterium ulcerans, Enterococcus faecium* (including vancomycin-resistant *E. faecium*, or VRE), and *Peptostreptococcus anaerobius.*

Additional bacteria genera in which compounds disclosed herein may be useful in controlling biofilms include, but are not limited to, *Actinomyces, Propionibacterium, Nocardia* and *Streptomyces. Actinomyces* is a Gram-positive genus that includes opportunistic pathogens in humans and animals, e.g., in the oral cavity, and can cause actinomycosis (cause by, e.g., *Actinomyces israelii*). *Propionibacterium acnes* is a Gram-positive species that can cause acne and chronic blepharitis and endophthalmitis (e.g., after intraocular surgury). *Nocardia* is a Gram-positive genus that includes opportunistic pathogenic species causing, e.g., slowly progressive pneumonia, encephalitis, etc. *Streptomyces* is a Gram-positive genus that occasionally are found in human infections, such as mycetoma (caused by, e.g., *S. somaliensis* and *S. sudanensis*).

A method for treating a chronic bacterial infection in a subject in need thereof is disclosed, comprising administering active compound to said subject in an amount effective to inhibit, reduce, or remove a biofilm component of said chronic bacterial infection. "Treating" as used herein refers to any type of activity that imparts a benefit to a patient afflicted with a disease, including improvement in the condition of the patient (e.g., in one or more symptoms), delay in the progression of the disease, delay in onset of the disease, etc. The present invention is primarily concerned with the treatment of human subjects, but the invention may also be carried out on animal subjects, particularly mammalian subjects (e.g., mice, rats, dogs, cats, rabbits, and horses), avian subjects (e.g., parrots, geese, quail, pheasant), livestock (e.g., pigs, sheep, goats, cows, chickens, turkey, duck, ostrich, emu), reptile and amphibian subjects, for veterinary purposes or animal husbandry, and for drug screening and drug development purposes.

A "chronic bacterial infection" is a bacterial infection that is of a long duration or frequent recurrence. For example, a chronic middle ear infection, or otitis media, can occur when the Eustachian tube becomes blocked repeatedly due to allergies, multiple infections, ear trauma, or swelling of the adenoids. The definition of "long duration" will depend upon the particular infection. For example, in the case of a chronic middle ear infection, it may last for weeks to months. Other known chronic bacterial infections include urinary tract infection (most commonly caused by *Escherichia coli* and/or *Staphylococcus saprophyticus*), gastritis (most commonly caused by *Helicobacter pylori*), respiratory infection (such as those commonly afflicting patents with cystic fibrosis, most commonly caused by *Pseudomonas aeuroginosa*), cystitis (most commonly caused by *Escherichia coli*), pyelonephritis (most commonly caused by *Proteus* species, *Escherichia coli* and/or *Pseudomonas* species), osteomyelitis (most commonly caused by *Staphylococcus aureus*, but also by *Escheri-* chia coli), bacteremia, skin infection, rosacea, acne, chronic wound infection, infectious kidney stones (can be caused by *Proteus mirabilis*), bacterial endocarditis, and sinus infection. A common infection afflicting pigs is atrophic rhinitis (caused by *Bordatella* species, e.g. *Bordatella bronchiseptica, Bordatella rhinitis*, etc.).

Various nosocomial infections that are especially prevalent in intensive care units implicate *Acinetobacter* species such as *Acinetobacter baumannii* and *Acinetobacter lwoffi*. *Acinetobacter baumanni* is a frequent cause of nosocomial pneumonia, and can also cause skin and wound infections and bacteremia. *Acinetobacter lwoffi* causes meningitis. The *Acinetobacter* species are resistant to many classes of antibiotics. The CDC has reported that bloodstream infections implicating *Acinetobacter baumanni* were becoming more prevalent among service members injured during the military action in Iraq and Afghanistan.

*Staphylococcus aureus* is a common cause of nosocomial infections, often causing post-surgical wound infections. *Staphylococcus aureus* can also cause variety of other infections in humans (e.g., skin infections), and can contribute to mastitis in dairy cows. *Staphylococcus aureus* has become resistant to many of the commonly used antibiotics.

E. DEVICES

Medical devices comprising a substrate and an effective amount of active compound are also disclosed. "Medical device" as used herein refers to an object that is inserted or implanted in a subject or applied to a surface of a subject. Common examples of medical devices include stents, fasteners, ports, catheters, scaffolds and grafts. A "medical device substrate" can be made of a variety of biocompatible materials, including, but not limited to, metals, ceramics, polymers, gels, and fluids not normally found within the human body. Examples of polymers useful in fabricating medical devices include such polymers as silicones, rubbers, latex, plastics, polyanhydrides, polyesters, polyorthoesters, polyamides, polyacrylonitrile, polyurethanes, polyethylene, polytetrafluoroethylene, polyethylenetetraphthalate, etc. Medical devices can also be fabricated using naturally-occurring materials or treated with naturally-occurring materials. Medical devices can include any combination of artificial materials, e.g., combinations selected because of the particular characteristics of the components. Medical devices can be intended for short-term or long-term residence where they are positioned. A hip implant is intended for several decades of use, for example. By contrast, a tissue expander may only be needed for a few months, and is removed thereafter.

Some examples of medical devices are found in U.S. Pat. No. 7,081,133 (Chinn et al.); U.S. Pat. No. 6,562,295 (Neuberger); and U.S. Pat. No. 6,387,363 (Gruskin); each incorporated by reference herein in its entirety.

F. COVALENT COUPLING OF ACTIVE COMPOUNDS

In some embodiments, active compounds as described herein are covalently coupled to substrates. Examples of substrates include solid supports and polymers. The polymers, typically organic polymers, may be in solid form, liquid form, dispersed or solubilized in a solvent (e.g., to form a coating composition as described above), etc. The solid support may include the substrate examples as described above to be coated with or treated with active compounds of the invention.

Covalent coupling can be carried out by any suitable technique. Active compounds of the present invention may be appended to a substrate via aldehyde condensation, amine bond, amide or peptide bond, carbon-carbon bond, or any suitable technique commonly used in the art. See also U.S. Patent Application Publication No. 2008/0181923 to Melander et al., which is incorporated by reference herein. A preferred method according to some embodiments is amine or amide bond formation. Further examples and explanations of these types of reactions can be found in U.S. Pat. No. 6,136,157 (Lindeberg et al.) and U.S. Pat. No. 7,115,653 (Baxter et al.), which are each hereby incorporated by reference in their entirety.

Various coupling reactions can be used to covalently link active compounds of the present invention to a substrate. Examples of coupling reactions that can be used include, but are not limited to, Hiyama, Suzuki, Sonogashira, Heck, Stille, Negishi, Kumada, Wurtz, Ullmann, Cadiot-Chodkiewicz, Buchwald-Hartwig, and Grignard reactions. For example, an active compound that is substituted with a halide (e.g. bromo or chloro) can be coupled to a substrate via a Heck reaction.

Some aspects of the present invention are described in more detail in the following non-limiting examples.

EXAMPLE 1

Synthesis and bacterial biofilm inhibition studies of ethyl N-(2-phenethyl) carbamate derivatives. An 88-member library of compounds based upon the bacterial metabolite ethyl N-(2-phenethyl) carbamate (2d), isolated from the marine bacteria SCRC3P79 (*Cytophaga* sp.), was evaluated. It had been reported that 2d exhibited moderate antibiofilm activity against the marine α-proteobacteria *Rhodospirillum salexigens*. Yamada performed preliminary analogue synthesis by varying the aromatic appendage with substituted benzene rings and the ethyl appendage with a handful of aliphatic subunits. However, none of the analogues demonstrated improved activity in comparison to 2d (Yamada et al., *Bull. Chem. Soc. Jpn.*, 1997, 70, 3061).

Ethyl N-(2-phenethyl) carbamate 2d was synthesized from commercially available materials by routine acylation methodology (ethyl chloroformate/TEA in DCM) (Scheme 1). Compound 2d was isolated in 96% yield without recourse to chromatographic purification.

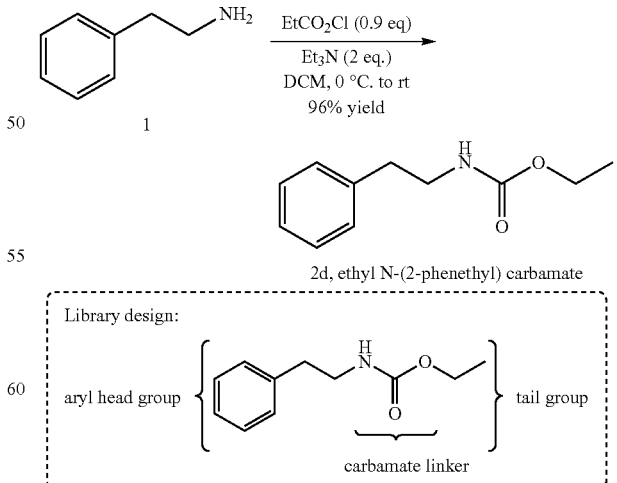

Similar to the results reported in Yamada et al., 2d displayed mediocre antibiofilm activity against *R. salexigens*, giving a 59.7% inhibition at a 200 μM concentration as judged by a crystal violet reporter assay (see O'Toole et al., *Mol. Microbiol.*, 1998, 30, 295).

Interestingly, we found that a 200 μM concentration of 2d also displayed activities against various medically relevant bacterial strains, inhibiting 63.1%, 68.1%, 80.2%, 52.0% and 40.8% of biofilm formation for *S. epidermidis*, methicillin-resistant *S. aureus* (MRSA), vancomycin-resistant *Enterococcus faecium* (VRE), multi-drug resistant *Acinetobacter baumannii* (MDRAB), and *E. coli* respectively (Table 1).

TABLE 1

Biofilm inhibition activity of 2d against various bacteria.

| Strain | % Inhibition (200 μM 2d) |
|---|---|
| *S. epidermidis* | 63.1 |
| MRSA | 68.1 |
| VRE | 80.2 |
| *R. salexigens* | 59.7 |
| MDRAB | 52.0 |
| *E. coli* | 40.8 |

After successfully obtaining antibiofilm activity for 2d against medically relevant bacteria, a three-part structure-activity analysis was designed (see Scheme 1), which entailed a systematic modulation of the metabolite's aromatic head region, carbamate linkage, and tail group.

These natural product analogues were synthesized using the same method used to prepare 2d. Specifically, the respective amine was reacted with 0.9 equivalent of the requisite chloroformate, isocyanate, dicarbonate, or isothiocyanate in the presence of 2.0 equivalents of triethylamine in dichloromethane. Each of the listed amines was reacted independently with each acylating reagent to produce the 88-member library in yields ranging from 76-98%.

Various aromatic head groups were used, incorporating the indole, triazole, indane, tetrahydroquinoline, indoline, and pyridine, as well as para-amino, para-methoxy, and para-bromo substituted phenyl rings. The carbamate heteroatomic core was varied through the substitution with a thiocarbamate, urea, and thiourea linkages. Tail modifications were made through the incorporation of the (−)-menthyl, benzyl, t-butyl and cholesteryl groups (Scheme 2).

Scheme 2. Analogue library.

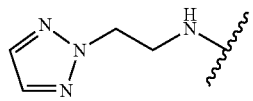
2a-2h

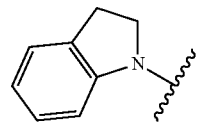
3a-3h

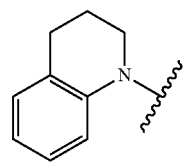
4a-4h

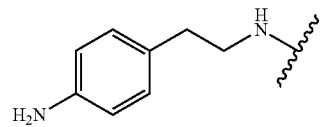
5a-5h

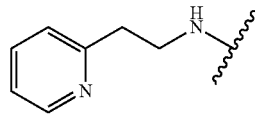
6a-6h

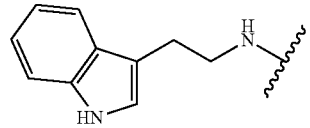
7a-7h

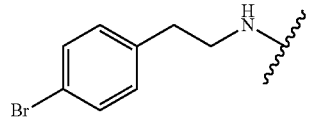
8a-8h

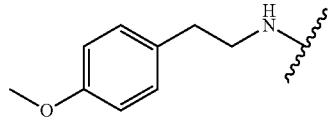
9a-9h

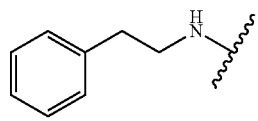
10a-10h

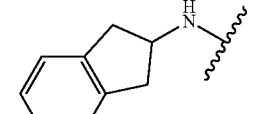
11a-11h

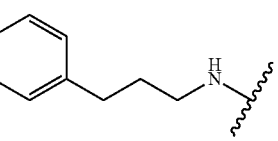
12a-12h

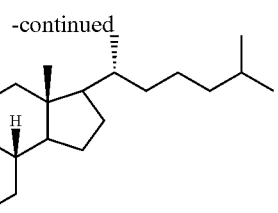

f

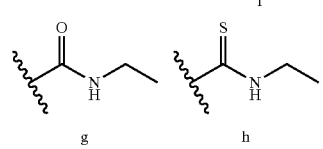

g    h

Once 2a-12h had been synthesized, they were screened for their ability to inhibit biofilm formation of *S. epidermidis*, MRSA, VRE, *R. salexigens*, MDRAB and *E. coli* at a 200 μM concentration. None of the compounds displayed notable antibiofilm activity against *S. epidermidis*, VRE, *R. salexigens*, or MDRAB. However, compounds 4c, 8a, 9a, and 10a displayed greater than 90% inhibition of MRSA biofilms at 200 μM concentration. Furthermore, compounds 5a, 9a, and 10c exhibited greater than 80% inhibition of *E. coli* biofilms at 200 μM concentration.

Dose-response curves were generated for the lead compounds for the inhibition of MRSA and *E. coli* biofilms (Table 2). Non-bactericidal antibiofilm activity was verified through colony count analysis of the planktonic viability in the presence and in the absence of each compound at their $IC_{50}$ value (i.e. the concentration that inhibits 50% of biofilm formation). Against MRSA, $IC_{50}$ values were determined to be 49.8 μM, 4.87 μM and 4.70 μM for 8a, 9a, and 10a respectively. Against *E. coli*, $IC_{50}$ values were determined to be 28.3 μM, 34.6 μM and 66.4 μM for 5a, 9a, and 10c, respectively.

TABLE 2

Biofilm inhibition ($IC_{50}$) against MRSA and *E. coli*.

| Compound | MRSA $IC_{50}$ (μM) | *E. coli* $IC_{50}$ (μM) |
|---|---|---|
| 5a | — | 28.3 |
| 8a | 49.8 | — |
| 9a | 4.87 | 34.6 |
| 10a | 4.70 | — |
| 10c | — | 66.4 |

Given the potency of our lead compounds toward inhibiting MRSA biofilms, we next explored their activity against various other *S. aureus* strains. Specifically, 8a, 9a, and 10a were screened against three additional *S. aureus* strains (ATCC #'s 29213, 29740, and 25923). $IC_{50}$ values were determined for each compound against each of the *S. aureus* strains. In some cases, the compounds were found to be more potent than they were against MRSA.

$IC_{50}$ values for compound 8a were found to be 21.2 μM, 24.3 μM and 71.9 μM against 29213, 29740 and 25923 respectively. For 9a they were found to be 124 μM, 82.2 μM and 19.7 μM for 29213, 29740 and 25923 respectively. Lastly, for compound 10a, which was found to be the most active compound overall, $IC_{50}$ values were determined to be 4.70 μM, 2.84 μM and 37.4 μM for 29213, 29740 and 25923 respectively (Table 3). Again, planktonic viability in the presence of the test compounds was verified through colony count analysis.

TABLE 3

Biofilm inhibition ($IC_{50}$) against other *S. aureus* strains.

| Compound | 29213 $IC_{50}$ (μM) | 29740 $IC_{50}$ (μM) | 25923 $IC_{50}$ (μM) |
|---|---|---|---|
| 8a | 21.2 | 24.3 | 71.9 |
| 9a | 124 | 82.2 | 19.7 |
| 10a | 4.70 | 2.85 | 37.4 |

Interestingly, our most potent inhibitors of the *S. aureus* strains including MRSA contained (−)-menthyl carbamates. Indeed, (−)-menthol and its derivatives have long been shown to have various antimicrobial and antiplasmid effects on bacteria (Schelz et al., *Fitoterapia*, 2006, 77, 279; Filoche et al., *Oral Microb. Immun.*, 2005, 20, 221; Iscan et al., *J. Agric. Food Chem.*, 2002, 50, 3943; Kurita et al. *Agric. Biol. Chem.*, 1982, 46, 159; Aridogan et al., *Arch. Pharm. Res. Vol.* 2002, 25, 860.). Along with (−)-menthol (13), the related natural products thymol (14) and carvacrol (15) (Scheme 3, dashed box) are also known to possess antimicrobial activity (Arfa et al., *Lett. Appl. Microbiol.*, 2006, 43, 149; Sivropoulou et al., *J. Agric. Food Chem.*, 1996, 44, 1202; Ultee et al., *J. Food Protect.*, 2000, 63, 620). In light of this observation, we prepared the thymyl and carvacryl carbamate analogues of 9a and 10a. We chose these two compounds for analogue design because they had the lowest $IC_{50}$ values against MRSA and both worked well against 29213, 29740, and 25923 (see Tables 2 and 3). Additionally, we prepared the stereochemical antipodes of 9a and 10a by employing (+)-menthyl carbamate. Finally, we prepared the cyclohexyl carbamate derivatives of 9a and 10a as a control (Scheme 3).

Scheme 3. Analgoues of compounds 9a and 10a.

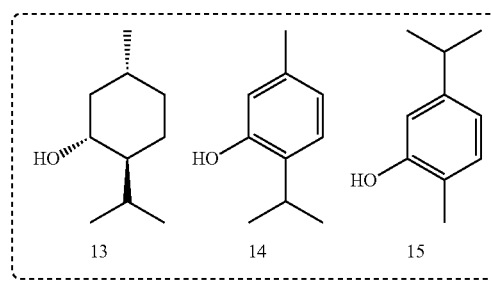

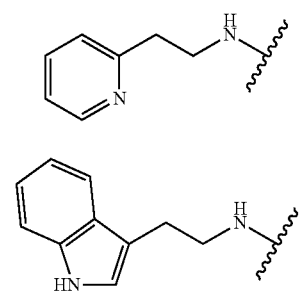

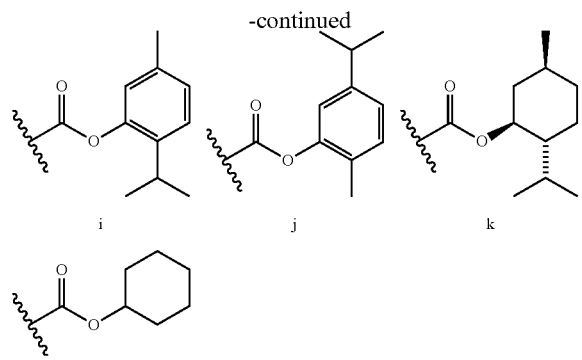

With compounds 91-101 in hand, they were then screened for biofilm inhibition activity along with (−)-menthol and (−)-menthol methyl ether against MRSA and 29213. Interestingly, none of the analogues depicted in Scheme 3 displayed any notable biofilm inhibition activity against either MRSA or 29213 at a 200 μM concentration, with the exception of 9k and 10k. These compounds were found to have identical antibiofilm properties as their enantiomers, 9a and 10a. Importantly, both (−)-menthol and (−)-menthol methyl ether were found to be completely inactive.

Lastly, 2d, 8a, 9a, and 10a were preliminarily screened for cytotoxicity. This was assessed using a red blood cell hemolysis assay using difibrinated sheep blood. In each case, the carbamates were found to show no red blood cell lysis up to the highest concentration tested (1.2 mM).

In summary, by targeting analogues of the bacterial metabolite 2d, we have discovered a novel class of biofilm inhibitors based upon a menthyl carbamate scaffold. Two potent compounds (9a and 10a) display low micromolar $IC_{50}$ values for the inhibition of various *S. aureus* biofilms including those from the medically relevant MRSA. This scaffold represents a unique class of compounds for combating bacterial biofilms.

GENERAL EXPERIMENTAL

All reagents used for chemical synthesis were purchased from commercially available sources and used without further purification. Chromatography was performed using 60 Å mesh standard grade silica gel from Sorbtech. NMR solvents were obtained from Cambridge Isotope Labs and used as is. $^1$H NMR (300 MHz or 400 MHz) and $^{13}$C NMR (75 MHz or 100 MHz) spectra were recorded at 25° C. on Varian Mercury spectrometers. Chemical shifts (δ) are given in ppm relative to tetramethylsilane or the respective NMR solvent; coupling constants (J) are in hertz (Hz). Abbreviations used are s=singlet, bs=broad singlet, d=doublet, dd=doublet of doublets, t=triplet, dt=doublet of triplets, bt=broad triplet, qt=quartet, m=multiplet, bm=broad multiplet and br=broad. Mass spectra were obtained at the NCSU Department of Chemistry Mass Spectrometry Facility.

General Procedure for Compounds 2a-2h, 3a-3h, 4a-4-h, 5a-5h, 6a-6h, 7a-7h, 11a-h and 12a-12h.

Ten mL of dichloromethane and a stir bar was added to 100-200 mg of the amine. Two equivalents of triethylamine was then added and the reaction mixture was cooled to 0° C. while stirring. Then, 0.9 equivalents of the chloroformate, isocyanate or thioisocyanate was added dropwise to the reaction mixture and was allowed to slowly warm to room temperature and continued stirring overnight. The reaction mixture was then diluted with more dichloromethane, washed twice with 1N HCl, washed twice with brine, dried with sodium sulfate and then concentrated in vacuo.

General Procedure for Compounds 8a-8h, 9a-9l and 10a-10l.

Ten mL of dichloromethane and a stir bar was added to 100-200 mg of the amine. Two equivalents of triethylamine was then added and the reaction mixture was cooled to 0° C. while stirring. Then, 0.9 equivalents of the chloroformate, isocyanate or thioisocyanate was added dropwise to the reaction mixture and was allowed to slowly warm to room temperature and continued stirring overnight. The reaction mixture was then diluted with more dichloromethane, washed twice with brine, dried with sodium sulfate and then concentrated in vacuo. The crude mixture was then purified via flash chromatography on silica gel using a 2.5%-10% methanol/dichlormethane eluent.

2-(2H-1,2,3-triazol-2-yl)ethanamine (5)

White solid, mp=129-131° C. $^1$H NMR (300 MHz, CDCl$_3$) δ 7.43 (s, 2H), δ 4.55 (t, J=1.2 Hz, 2H), δ 3.33 (t, J=5.7 Hz, 2H) ppm; $^{13}$C NMR (75 MHz, CDCl$_3$) δ 135.1, 51.3, 38.8 ppm; IR $v_{max}$ (cm$^{-1}$) 3054, 2987, 2306, 1421, 1258; HRMS (ESI) calcd for $C_4H_8N_4$ (M+) 113.0822. found 113.0819.

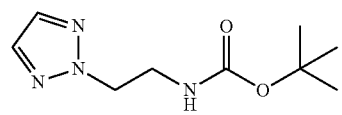

tert-butyl 2-(2H-1,2,3-triazol-2-yl)ethylcarbamate (5e)

White solid. mp=64-66° C. $^1$H NMR (300 MHz, CDCl$_3$) δ 7.55 (s, 2H), δ 5.15 (s, 1H), δ 4.49 (t, J=5.7 Hz, 2H), δ 3.63 (q, J=5.7, 5.1 Hz, 2H), δ 1.36 (s, 9H) ppm; $^{13}$C NMR (75 MHz, CDCl$_3$) δ 155.9, 134.5, 79.8, 54.8, 40.2, 28.5, 27.8 ppm; IR $v_{max}$ (cm$^{-1}$) 3054, 2986, 1713, 1506; HRMS (ESI) calcd for $C_9H_{16}N_4O_2$ (M+) 235.1165. found 235.1169.

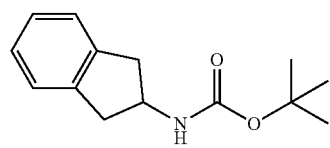 [SMILES: CC(C)(C)OC(=O)NC1Cc2ccccc2C1]

tert-butyl 2,3-dihydro-1H-inden-2-ylcarbamate (3e)

White solid. mp=51-53° C. $^1$H NMR (300 MHz, CDCl$_3$) δ 7.19 (m, 4H), δ 4.84 (s, 1H), δ 4.45 (s, 1H), δ 3.29 (d, J=7.2 Hz, 1H), δ 3.24 (d, J=6.9 Hz, 1H), δ 2.80 (d, J=4.8 Hz, 1H), δ 2.75 (d, J=4.8 Hz, 1H), δ 1.43 (s, 9H) ppm; $^{13}$C NMR (75 MHz, CDCl$_3$) δ153.5, 140.9, 126.5, 124.7, 79.3, 51.9, 40.3, 28.4 ppm; IR $v_{max}$ (cm$^{-1}$) 3419, 2321, 1641; HRMS (ESI) calcd for $C_{17}H_{17}NO_2$ (M+) 256.1308. found 256.1308.

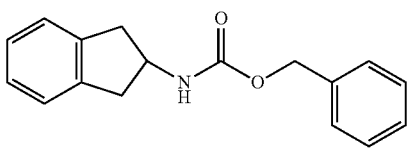 [SMILES: O=C(NC1Cc2ccccc2C1)OCc1ccccc1]

benzyl 2,3-dihydro-1H-inden-2-ylcarbamate (3c)

Light yellow solid. mp=159-161° C. $^1$H NMR (300 MHz, CDCl$_3$) δ 7.35 (s, 4H), δ 7.13 (t, J=1.2 Hz, 5H), δ 5.09 (s, 2H), δ 4.56 (s, 2H), δ 3.28 (m, 2H), δ 2.77 (m, 2H) ppm; $^{13}$C NMR (75 MHz, CDCl$_3$) δ 141.3, 136.7, 128.8, 126.9, 125.0, 66.9, 51.8, 40.8 ppm; IR ν$_{max}$ (cm$^{-1}$) 3419, 2977, 1691, 1643, 1265; HRMS (ESI) calcd for C$_{17}$H$_{17}$NO$_2$ (M+) 268.1332. found 268.1337.

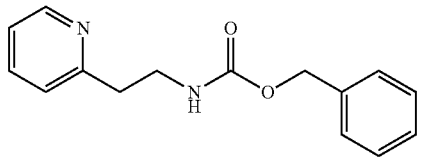 [SMILES: O=C(NCCc1ccccn1)OCc1ccccc1]

benzyl 2-(pyridin-2-yl)ethylcarbamate (9c)

Colorless oil. $^1$H NMR (300 MHz, CDCl$_3$) δ 8.43 (d, J=4.8 Hz, 1H), δ 7.52 (t, J=1.8 Hz, 1H), δ 7.23 (s, 5H), δ 7.06 (m, 2H), δ 5.91 (s, 1H), δ 5.04 (s, 2H), δ 3.57 (q, J=6.3 Hz, 6.3 Hz, 2H), δ 2.93 (t, J=6.6 Hz, 2H) ppm; $^{13}$C NMR (75 MHz, CDCl$_3$) δ 156.7, 149.4, 137.0, 128.6, 127.1, 123.7, 121.7, 66.7, 40.6, 37.8 ppm; 3440, 2092, 1644, 1261; HRMS (ESI) calcd for C$_{15}$H$_{16}$N$_2$O$_2$ (M+) 257.1285. found 257.1288.

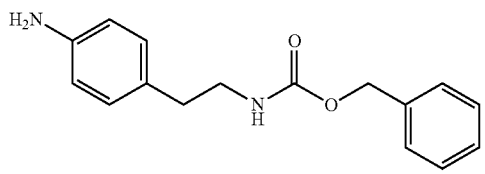 [SMILES: Nc1ccc(CCNC(=O)OCc2ccccc2)cc1]

benzyl 4-aminophenethylcarbamate (8c)

Light yellow solid. mp=70-73° C. $^1$H NMR (300 MHz, CDCl$_3$) δ 7.31 (s, 5H), δ 6.93 (d, J=8.1 Hz, 2H), δ 6.58 (d, J=8.4 Hz, 2H), δ 5.06 (s, 2H), δ 4.91 (s, 1H), δ 3.57 (s, 2H), δ 3.36 (q, J=6.6, 6.6 Hz, 2H), δ 2.65 (t, J=6.9 Hz, 2H) ppm; $^{13}$C NMR (75 MHz, CDCl$_3$) δ 156.6, 145.2, 136.9, 129.8, 128.7, 115.6, 66.8, 58.8, 42.7, 35.4 ppm; IR ν$_{max}$ (cm$^{-1}$) 3389, 1682, 1543; HRMS (ESI) calcd for C$_{16}$H$_{18}$N$_2$O$_2$ (M+) 271.1441. found 271.1446.

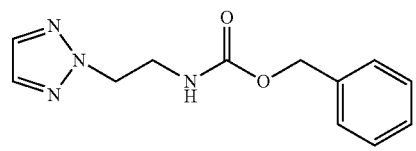 [SMILES: O=C(NCCn1nccn1)OCc1ccccc1]

benzyl 2-(2H-1,2,3-triazol-2-yl)ethylcarbamate (5c)

Light yellow residue. $^1$H NMR (300 MHz, CDCl$_3$) δ 7.58 (s, 2H), δ 7.28 (m, 5H), δ 5.38 (s, 1H), δ 5.15 (s, 2H), δ 4.51 (t, J=5.4 Hz, 2H), δ 3.75 (t, 6.3 Hz, 2H) ppm; $^{13}$C NMR (75 MHz, CDCl$_3$) δ 156.5, 136.5, 134.5, 128.4, 67.1, 54.6, 40.6 ppm; IR ν$_{max}$ (cm$^{-1}$) 3440, 3054, 2986, 2305, 1719; HRMS (ESI) calcd for C$_{12}$H$_{14}$N$_4$O$_2$ (M+) 269.1009. found 269.1011.

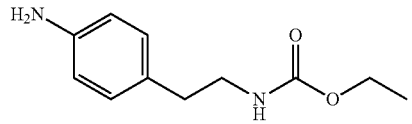

ethyl 4-aminophenethylcarbamate (8d)

Light yellow oil. $^1$H NMR (300 MHz, CDCl$_3$) δ 6.95 (d, J=8.1 Hz, 2H), δ 6.61 (d, J=6.3 Hz, 2H), δ 4.89 (s, 1H), δ 4.08 (q, J=6.9, 7.2 Hz, 2H), δ 3.74 (s, 2H), δ 3.33 (t, J=6.3 Hz, 2H), δ 2.65 (t, J=7.2 Hz, 2H), δ 1.19 (t, J=7.2 Hz, 3H) ppm; $^{13}$C NMR (75 MHz, CDCl$_3$) δ 156.9, 145.0, 129.8, 115.7, 60.9, 42.6, 35.4, 14.9 ppm; IR ν$_{max}$ (cm$^{-1}$) 3346, 2932, 1698, 1627; HRMS (ESI) calcd for C$_{11}$H$_{16}$N$_2$O$_2$ (M+) 209.1285. found 209.1278.

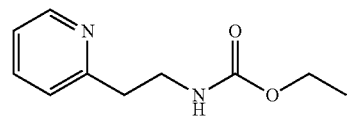

ethyl 2-(pyridin-2-yl)ethylcarbamate (9d)

Light yellow solid. mp=56-58° C. $^1$H NMR (300 MHz, CDCl$_3$) δ 8.41 (d, J=4.8 Hz, 1H), δ 7.49 (t, J=5.7 Hz, 1H), δ 7.02 (m, 2H), δ 5.77 (s, 1H), δ 4.00 (q, J=6.9, 7.2 Hz, 2H), δ 3.50 (q, J=6.3, 6.6 Hz, 2H), δ 2.89 (t, J=6.6 Hz, 2H), δ 1.11 (t, J=6.9 Hz, 3H) ppm; $^{13}$C NMR (75 MHz, CDCl$_3$) δ 159.5, 156.9, 149.3, 136.6, 123.5, 121.6, 60.6, 40.4, 37.9, 14.8 ppm; IR ν$_{max}$ (cm$^{-1}$) 3435, 2091, 1641, 1259; HRMS (ESI) calcd for C$_{14}$H$_{17}$N$_5$O$_2$S (M+). found.

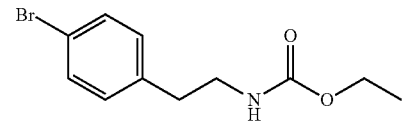

ethyl 4-bromophenethylcarbamate (11d)

White solid. mp=63-65° C. $^1$H NMR (300 MHz, CDCl$_3$) δ 7.42 (d, J=2.7 Hz, 2H), δ 7.07 (d, J=8.7 Hz, 2H), δ 4.94 (s, 1H), δ 4.09 (q, J=6.9, 7.2 Hz, 2H), δ 3.39 (q, J=6.6, 6.9 Hz, 2H), δ 2.75 (t, 6.9 Hz, 2H), δ 1.21 (t, J=7.2 Hz, 3H) ppm; $^{13}$C NMR (75 MHz, CDCl$_3$) δ 156.8, 138.1, 131.7, 120.5, 61.0, 42.1, 35.8, 14.9 ppm; IR ν$_{max}$ (cm$^{-1}$) 3348, 2975, 1691, 1537, 1260; HRMS (ESI) calcd for C$_{11}$H$_{14}$BrNO$_2$ (M+) 227.0281. found 227.0279.

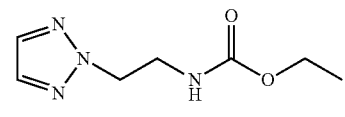

ethyl 2-(2H-1,2,3-triazol-2-yl)ethylcarbamate (5d)

Colorless oil. $^1$H NMR (300 MHz, CDCl$_3$) δ 7.62 (s, 2H), δ 6.31 (s, 1H), δ 4.671 (t, J=4.2 Hz, 2H), δ 4.17 (q, J=4.5, 4.5

Hz, 2H), δ 3.31 (s, 2H), δ 1.21 (t, J=6.9 Hz, 3H) ppm; $^{13}$C NMR (75 MHz, CDCl$_3$) δ 202.1, 134.7, 54.2, 44.3, 41.8, 14.1 ppm; IR ν$_{max}$ (cm$^{-1}$) 3434, 1642; HRMS (ESI) calcd for C$_{14}$H$_{17}$N$_5$O$_2$S (M+). found.

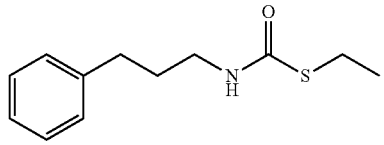

S-ethyl 3-phenylpropylcarbamothioate (4b)

Colorless oil. $^1$H NMR (300 MHz, CDCl$_3$) δ 7.25-7.10 (m, 5H), δ 6.24 (s, 1H), δ 3.26 (t, J=5.7 Hz, 2H), δ 2.82 (q, J=4.8, 6.9 Hz, 2H), δ 2.58 (t, J=7.8 Hz, 2H), δ 1.76 (m, 2H), δ 1.26 (t, J=7.5 Hz, 3H) ppm; $^{13}$C NMR (75 MHz, CDCl$_3$) δ 137.8, 141.7, 128.7, 126.5, 41.3, 33.4, 32.0, 24.5, 16.1 ppm; IR ν$_{max}$ (cm$^{-1}$) 3318, 3027, 2929, 2867, 1650, 1624, 1215, 700; HRMS (ESI) calcd for C$_{12}$H$_{17}$NOS (M+) 224.1104. found 224.1099.

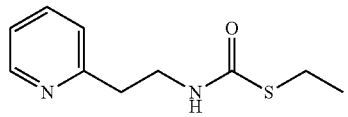

S-ethyl 2-(pyridin-2-yl)ethylcarbamothioate (9b)

Colorless oil. $^1$H NMR (300 MHz, CDCl$_3$) δ 8.37 (d, J=3 Hz, 1H), δ 7.47 (t, J=6.0 Hz, 1H), δ 7.01 (m, 2H), δ 6.88 (s, 1H), δ 3.58 (q, J=4.8, 4.5, 2H), δ 2.89 (t, J=5.1 Hz, 2H), δ 2.78 (q, J=5.4, 5.4 Hz, 2H), δ 1.15 (t, J=5.1 Hz, 3H) ppm; $^{13}$C NMR (75 MHz, CDCl$_3$) δ 159.3, 149.3, 136.8, 123.6, 121.8, 40.7, 37.4, 24.6, 15.9 ppm; IR ν$_{max}$ (cm$^{-1}$) 3432, 2089, 1645, 1213; HRMS (ESI) calcd for C$_{14}$H$_{17}$N$_5$O$_2$S (M+). found.

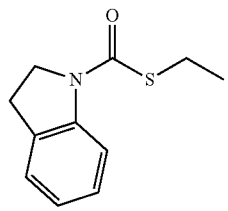

S-ethyl indoline-1-carbothioate (6b)

Light yellow oil. $^1$H NMR (300 MHz, CDCl$_3$) δ 7.97 (d, J=5.7 Hz, 1H), δ 7.08-6.88 (m, 4H), δ 3.80 (t, J=7.8 Hz, 2H), δ 2.94 (q, J=6.0, 5.4 Hz, 2H), δ 2.89 (t, J=3.3 Hz, 2H), δ 1.31 (t, J=5.7 Hz, 3H) ppm; $^{13}$C NMR (75 MHz, CDCl$_3$) δ 165.6, 143.0, 131.3, 127.6, 124.9, 123.6, 116.0, 47.3, 28.0, 24.7, 15.7 ppm; IR ν$_{max}$ (cm$^{-1}$) 3053, 2932, 2253, 1712, 1598, 1650; HRMS (ESI) calcd for C$_{11}$H$_{13}$NOS (M+) 208.0791. found 208.0788.

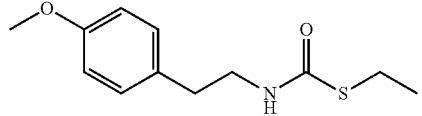 [SMILES: CCSC(=O)NCCc1ccc(OC)cc1]

S-ethyl 4-methoxyphenethylcarbamothioate (12b)

Colorless oil. $^1$H NMR (300 MHz, CDCl$_3$) δ 7.09 (d, J=8.4 Hz, 2H), δ 6.83 (d, J=8.7 Hz, 2H), δ 5.96 (s, 1H), δ 3.50 (s, 3H), δ 3.45 (q, J=6.3, 6.6 Hz, 2H), δ 2.91 (q, J=3.3, 3.3 Hz, 2H), δ 2.75 (t, J=7.5 Hz, 2H), δ 1.28 (t, J=6.9 Hz, 3H) ppm; $^{13}$C NMR (75 MHz, CDCl$_3$) δ 167.7, 158.5, 130.9, 129.9, 114.2, 55.4, 43.0, 35.2, 24.4, 16.0 ppm; IR ν$_{max}$ (cm$^{-1}$) 3323, 3034, 2962, 1640, 1514; HRMS (ESI) calcd for C$_{14}$H$_{17}$N$_5$O$_2$S (M+). found.

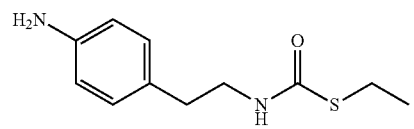

S-ethyl 4-aminophenethylcarbamothioate (8b)

Light yellow oil. $^1$H NMR (400 MHz, CDCl$_3$) δ 6.92 (d, J=6.8, 2H), δ 6.59 (t, J=6.4 Hz, 2H), δ 5.87 (s, 1H), δ 3.77 (s, 1H), δ 3.41 (t, J=5.6 Hz, 2H), δ 2.86 (q, J=7.2, 7.2 Hz, 2H), δ 2.67 (t, J=6.4 Hz, 2H), δ 1.25 (t, J=5.2 Hz, 3H) ppm; $^{13}$C NMR (100 MHz, CDCl$_3$) δ 167.6, 145.1, 129.8, 115.7, 53.8, 43.0, 35.2, 24.5, 16.0 ppm; IR ν$_{max}$ (cm$^{-1}$) 3434, 2929, 2086, 1647, 1517, 1263, 1219, 970; HRMS (ESI) calcd for C$_{11}$H$_{16}$N$_2$OS (M+) 225.1056. found 225.1060.

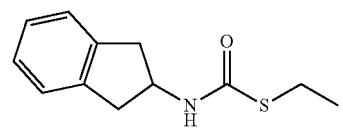

S-ethyl 2,3-dihydro-1H-inden-2-ylcarbamothioate (3b)

White solid. mp=107-110° C. $^1$H NMR (300 MHz, CDCl$_3$) δ 7.23-7.15 (m, 4H), δ 6.08 (d, J=5.4 Hz, 1H), δ 4.70 (s, 1H), δ 3.26 (dd, J=7.2, 7.2 Hz, 2H), δ 2.86 (q, J=5.4, 6.6 Hz, 2H), δ 1.29 (t, J=7.5 Hz, 3H) ppm; $^{13}$C NMR (75 MHz, CDCl$_3$) δ 167.4, 141.0, 127.1, 125.0, 52.7, 40.2, 24.5, 16.0 ppm; IR ν$_{max}$ (cm$^{-1}$) 3258, 3019, 2945, 1628; HRMS (ESI) calcd for C$_{12}$H$_{15}$NOS (M+) 222.0947. found 222.0944.

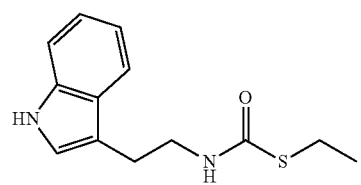 [SMILES: CCSC(=O)NCCc1c[nH]c2ccccc12]

S-ethyl 2-(1H-indol-3-yl)ethylcarbamothioate (10b)

Light yellow solid. mp=68-70° C. $^1$H NMR (300 MHz, CDCl$_3$) δ 8.52 (s, 1H), δ 7.54 (d, J=7.8, 1H), δ 7.24 (d, J=8.1, 1H), δ 7.17-7.04 (m, 2H), δ 6.82 (d, J=2.1 Hz, 1H), δ 5.74 (s, 1H), δ 3.51 (t, J=6.3 Hz, 2H), δ 2.91-2.83 (m, 4H), δ 1.26 (t, J=4.5 Hz, 3H) ppm; $^{13}$C NMR (75 MHz, CDCl$_3$) δ 168.2, 136.8, 127.6, 122.8, 119.7, 112.6, 42.1, 25.8, 24.7, 16.2 ppm; IR ν$_{max}$ (cm$^{-1}$) 3418, 3055, 2932, 1657, 1496; HRMS (ESI) calcd for C$_{13}$H$_{16}$N$_2$OS (M+) 249.1056. found 249.1052.

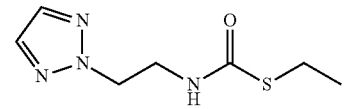

S-ethyl 2-(2H-1,2,3-triazol-2-yl)ethylcarbamothioate (5b)

Colorless oil. $^1$H NMR (300 MHz, CDCl$_3$) δ 7.59 (s, 1H), δ 6.14 (s, 1H), δ 4.56 (t, J=5.1 Hz, 2H), δ 3.83 (q, J=5.7, 5.7 Hz, 2H), δ 2.88 (q, J=7.5, 7.5 Hz, 2H), δ 1.25 (t, J=7.5 Hz, 3H) ppm; $^{13}$C NMR (75 MHz, CDCl$_3$) δ 202.1, 134.7, 54.3, 40.5, 24.6, 15.8 ppm; IR ν$_{max}$ (cm$^{-1}$) 3434, 1647, 671; HRMS (ESI) calcd for C$_{14}$H$_{17}$N$_5$O$_2$S (M+). found.

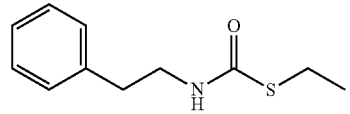

S-ethyl phenethylcarbamothioate (2b)

White solid. mp=95-98° C. $^1$H NMR (300 MHz, CDCl$_3$) δ 7.30 (m, 5H), δ 6.02 (s, 1H), δ 3.53 (q, J=6.6, 6.6 Hz, 2H), δ 2.89 (m, 4H), δ 1.30 (t, J=6.6 Hz, 3H) ppm; $^{13}$C NMR (75 MHz, CDCl$_3$) δ 167.8, 139.0, 129.1, 126.8, 42.9, 36.2, 24.5, 16.1 ppm; IR ν$_{max}$ (cm$^{-1}$) 3399, 2968, 2929, 2870, 2088, 1650, 1498; HRMS (ESI) calcd for C$_{11}$H$_{15}$NOS (M+) 210.0947. found 210.0944.

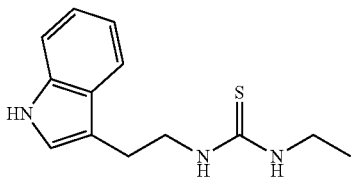 [SMILES: CCNC(=S)NCCc1c[nH]c2ccccc12]

1-(2-(1H-indol-3-yl)ethyl)-3-ethylthiourea (10h)

Light yellow residue. $^1$H NMR (300 MHz, CDCl$_3$) δ 8.67 (s, 1H), δ 7.58 (d, J=7.2 Hz, 1H), δ 7.33 (d, J=8.1 Hz, 1H), δ 7.18 (t, J=6.9 Hz, 1H), δ 7.08 (t, J=7.2 Hz, 1H), δ 6.86 (s, 1H), δ 6.24 (s, 2H), δ 3.69-2.94 (m, 6H), δ 1.00 (t, J=6.9 Hz, 3H) ppm; $^{13}$C NMR (75 MHz, CDCl$_3$) δ 180.9, 136.7, 127.4, 122.4, 118.9, 112.3, 45.0, 39.4, 25.3, 14.4 ppm; IR ν$_{max}$ (cm$^{-1}$) 3418, 2975, 1634, 1569, 1265, 738, 702; HRMS (ESI) calcd for C$_{13}$H$_{17}$N$_3$S (M+) 248.1216. found 248.1215.

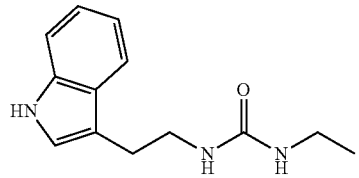 [SMILES: CCNC(=O)NCCc1c[nH]c2ccccc12]

1-(2-(1H-indol-3-yl)ethyl)-3-ethylurea (10g)

White solid. mp=109-112° C. $^1$H NMR (300 MHz, CDCl$_3$) δ 8.55 (s, 1H), δ 7.57 (d, J=7.8 Hz, 1H), δ 7.32-7.05 (m, 3H), δ 6.86 (s, 1H), δ 6.13 (s, 2H), δ 3.69 (m, 2H), δ 3.20 (m, 2H), δ 2.94 (t, J=6.3 Hz, 2H), δ 0.97 (t, J=7.2 Hz, 3H) 181.0, 136.6, 127.4, 122.9, 119.7, 112.3, 44.6, 39.0, 25.2, 14.3 ppm; $^{13}$C NMR (75 MHz, CDCl$_3$) δ 180.9, 136.6, 127.4, 122.9, 122.4, 119.7, 112.3, 111.9, 44.6, 38.9, 25.2, 14.4 ppm; IR ν$_{max}$ (cm$^{-1}$) 3944, 3467, 3054, 2986, 2306, 1536; HRMS (ESI) calcd for C$_{13}$H$_{17}$N$_3$O (M+) 232.1444. found 232.1445.

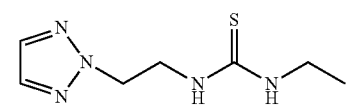

1-(2-(2H-1,2,3-triazol-2-yl)ethyl)-3-ethylthiourea (5h)

White solid. mp=91-93° C. $^1$H NMR (300 MHz, CDCl$_3$) δ 7.57 (d, J=9.6 Hz 2H), δ 6.64 (s, 2H), δ 4.62 (q, J=5.1, 3.9 Hz, 2H), δ 4.10 (q, J=5.7, 5.4 Hz), δ 3.28 (t, J=5.7 Hz, 2H), δ 1.15 (t, J=9.3 Hz, 3H) ppm; $^{13}$C NMR (75 MHz, CDCl$_3$) δ 197.1, 134.7, 100.4, 54.1, 44.2, 14.1 ppm; IR ν$_{max}$ (cm$^{-1}$) 3419, 1640, 1551; HRMS (ESI) calcd for C$_{14}$H$_{17}$N$_5$O$_2$S (M+). found.

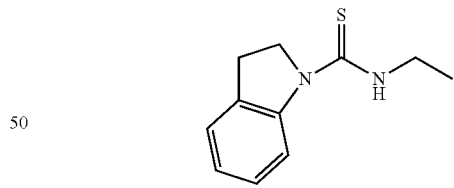

N-ethylindoline-1-carbothioamide (6h)

Yellow solid. mp=88-91° C. $^1$H NMR (300 MHz, CDCl$_3$) δ 7.83 (d, J=7.8 Hz, 2H), δ 7.08-7.01 (m, 2H), δ 6.85 (t, J=7.2 Hz, 1H), δ 6.21 (t, J=4.5 Hz, 1H), δ 4.09 (t, J=8.4 Hz, 2H), δ 3.63 (m, 2H), δ 2.87 (t, J=8.4 Hz, 2H), δ 1.18 (t, J=7.2 Hz, 3H) ppm; $^{13}$C NMR (75 MHz, CDCl$_3$) δ 178.9, 142.5, 134.0, 127.1, 125.9, 123.4, 114.9, 53.4, 40.3, 27.3, 14.6 ppm; IR ν$_{max}$ (cm$^{-1}$) 3390, 3279, 3030, 2972, 1638, 1522; HRMS (ESI) calcd for C$_{11}$H$_{14}$N$_2$S (M+) 207.0950. found 207.0946.

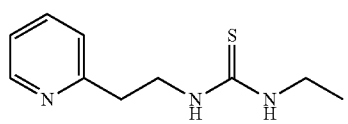

1-ethyl-3-(2-(pyridin-2-yl)ethyl)thiourea (9h)

Light yellow oil. $^1$H NMR (300 MHz, CDCl$_3$) δ 8.25 (d, J=4.2 Hz, 1H), δ 7.43 (t, J=7.5 Hz, 1H), δ 7.33 (s, 1H), δ 7.01-6.92 (m, 3H), δ 3.70 (t, J=3.9 Hz, 2H), δ 3.21 (m, 2H), δ 2.85 (t, J=6.3 Hz, 2H), δ 0.98 (t, J=6.9 Hz, 3H) ppm; $^{13}$C NMR (75 MHz, CDCl$_3$) δ 202.3, 181.0, 159.4, 150.0, 148.9, 137.1, 123.8, 121.9, 43.8, 39.0, 36.8, 24.7, 14.3 ppm; IR ν$_{max}$ (cm$^{-1}$) 3396, 2974, 2100, 1641, 1556; HRMS (ESI) calcd for C$_{14}$H$_{17}$N$_5$O$_2$S (M+). found.

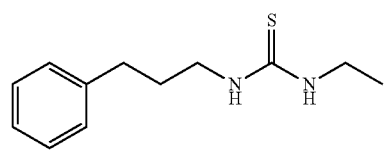

1-ethyl-3-(3-phenylpropyl)thiourea (4h)

White solid. mp=51-53° C. $^1$H NMR (300 MHz, CDCl$_3$) δ 7.25-7.11 (m, 5H), δ 6.42 (s, 2H), δ 3.42 (m, 2H), δ 3.34 (m, 2H), δ 2.61 (t, J=7.5 Hz, 2H), δ 1.86 (m, 2H), 1.10 (t, J=7.2 Hz, 3H) ppm; $^{13}$C NMR (75 MHz, CDCl$_3$) δ 181.3, 141.4, 128.7, 126.3, 39.3, 33.9, 30.8, 14.6 ppm; IR ν$_{max}$ (cm$^{-1}$) 3421, 3276, 3053, 2939, 2865, 1547, 1495; HRMS (ESI) calcd for C$_{12}$H$_{18}$N$_2$S (M+) 223.1263. found 223.1261.

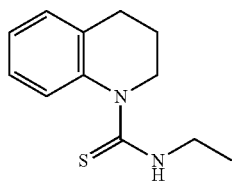

N-ethyl-3,4-dihydroquinoline-1(2H)-carbothioamide (7h)

Light yellow solid. mp=55-57° C. $^1$H NMR (300 MHz, CDCl$_3$) δ 7.09-6.97 (m, 4H), δ 6.22 (s, 1H), δ 4.09 (t, J=6.3 Hz, 2H), δ 3.50 (m, 2H), δ 2.59 (t, J=6.9 Hz, 2H), δ 1.84 (m, 2H), δ 1.02 (t, J=3.9 Hz, 3H) ppm; $^{13}$C NMR (75 MHz, CDCl$_3$) δ 181.9, 138.8, 134.0, 130.3, 126.8, 123.7, 49.1, 40.9, 26.7, 24.0, 14.3 ppm; IR ν$_{max}$ (cm$^{-1}$) 3396, 3034, 2934, 2875, 2211, 1640, 1516; HRMS (ESI) calcd for C$_{12}$H$_{16}$N$_2$S (M+) 221.1107. found 221.1105.

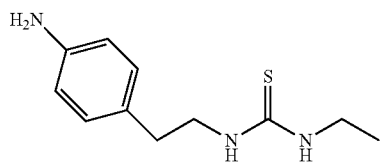

1-(4-aminophenethyl)-3-ethylthiourea (8h)

Light yellow oil. $^1$H NMR (300 MHz, CDCl$_3$) δ 6.94 (d, J=8.1, 2H), δ 6.57 (d, J=4.5 Hz, 2H), δ 6.06 (d, J=10.2 Hz, 2H), δ 3.60 (m, 4H), δ 3.26 (s, 2H), δ 2.72 (t, J=6.9 Hz, 2H), δ 1.08 (t, J=7.2 Hz, 3H) ppm; $^{13}$C NMR (75 MHz, CDCl$_3$) δ 181.3, 145.3, 129.8, 128.3, 115.7, 46.1, 39.1, 34.6, 14.4 ppm; IR ν$_{max}$ (cm$^{-1}$) 3408, 1626, 1553; HRMS (ESI) calcd for C$_{11}$H$_{17}$N$_3$S (M+) 224.1216. found 224.1212.

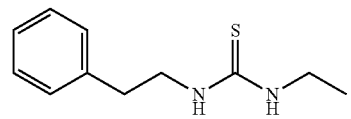

1-ethyl-3-phenethylthiourea (2h)

White solid. mp=56-58° C. $^1$H NMR (300 MHz, CDCl$_3$) δ 7.27-7.14 (m, 5H), δ 6.40 (d, J=10.2 Hz, 2H), δ 3.68 (t, J=5.1 Hz, 2H), δ 3.30 (m, 2H), δ 2.84 (t, J=7.2 Hz, 2H), δ 1.08 (t, J=7.2 Hz, 3H) ppm; $^{13}$C NMR (75 MHz, CDCl$_3$) δ 181.4, 138.7, 129.0, 126.9, 45.9, 39.1, 35.6, 14.4 ppm; IR ν$_{max}$ (cm$^{-1}$) 3420, 3269, 3054, 2984, 2935, 2875, 2685, 2306, 2253, 1711, 1546; HRMS (ESI) calcd for C$_{11}$H$_{16}$N$_2$S (M+) 209.1107. found 209.1103.

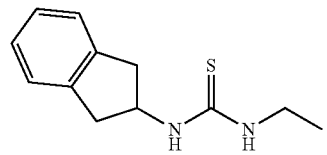

1-(2,3-dihydro-1H-inden-2-yl)-3-ethylthiourea (3h)

Grey solid. mp=87-91° C. $^1$H NMR (300 MHz, CDCl$_3$) δ 7.14 (m, 4H), δ 6.62 (s, 2H), δ 4.85 (m, 1H), δ 3.50-3.21 (m, 4H), δ 2.83 (dd, J=5.4, 5.1 Hz, 2H), δ 1.10 (t, J=7.5 Hz, 3H) ppm; $^{13}$C NMR (75 MHz, CDCl$_3$) δ 181.0, 140.8, 127.1, 125.0, 100.4, 55.5, 40.0, 14.6 ppm; IR ν$_{max}$ (cm$^{-1}$) 3267, 3066, 2972, 1673, 1483, 1548; HRMS (ESI) calcd for C$_{12}$H$_{16}$N$_2$S (M+) 221.1107. found 221.1106.

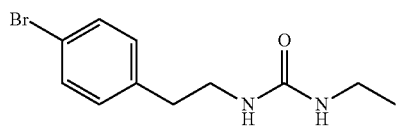

1-(4-bromophenethyl)-3-ethylurea (11g)

White solid. mp=137-139° C. $^1$H NMR (300 MHz, CDCl$_3$) δ 7.37 (d, J=8.1 Hz, 2H), δ 7.02 (d, J=8.1 Hz, 2H), δ 5.46 (d, J=16.5 Hz, 2H), δ 3.30 (m, 2H), δ 3.08 (q, J=6.0, 6.9 Hz, 2H), δ 2.67 (t, J=6.9 Hz, 2H), δ 1.05 (t, J=7.2 Hz, 3H) ppm; $^{13}$C NMR (75 MHz, CDCl$_3$) δ 159.1, 138.6, 131.7, 130.7, 120.3, 41.6, 36.3, 35.2, 15.8 ppm; IR ν$_{max}$ (cm$^{-1}$) 3327, 2971, 1620, 1488; HRMS (ESI) calcd for C$_{11}$H$_{15}$BrN$_2$O (M+) 271.0441. found 271.0439.

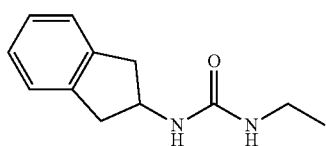

1-(2,3-dihydro-1H-inden-2-yl)-3-ethylurea (3g)

White solid. mp=117° C. $^1$H NMR (300 MHz, CDCl$_3$) δ 7.14 (m, 4H), δ 5.98 (s, 2H), δ 4.43 (m, 1H), δ 3.22-3.07 (m, 4H), δ 2.77 (dd, J=6.3, 5.7 Hz, 2H), δ 1.07 (t, J=6.9 Hz, 3H) ppm; $^{13}$C NMR (75 MHz, CDCl$_3$) δ 159.3, 141.4, 126.8, 124.9, 51.5, 40.7, 35.1, 15.9 ppm; IR ν$_{max}$ (cm$^{-1}$) 3348, 2968, 1623, 1579, 1259, 736; HRMS (ESI) calcd for C$_{12}$H$_{16}$N$_2$O (M+) 205.1335. found 205.1333.

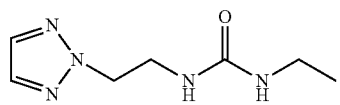

1-(2-(2H-1,2,3-triazol-2-yl)ethyl)-3-ethylurea (5g)

White solid. mp=109° C. $^1$H NMR (300 MHz, CDCl$_3$) δ 7.57 (s, 2H), δ 6.63 (d, J=25.5 Hz, 2H), δ 4.62 (m, 2H), δ 4.10 (t, J=5.1 Hz, 2H), δ 3.28 (m, 2H), δ 1.16 (t, J=8.7 Hz, 3H) ppm; $^{13}$C NMR (75 MHz, CDCl$_3$) δ 174.6, 134.7, 54.3, 44.2, 38.7, 14.1 ppm; IR ν$_{max}$ (cm$^{-1}$) 3434, 1640; HRMS (ESI) calcd for C$_7$H$_{13}$N$_5$O (M+) 206.1012. found 206.1014.

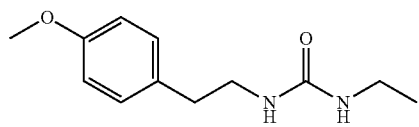 [SMILES: CCNC(=O)NCCc1ccc(OC)cc1]

1-ethyl-3-(4-methoxyphenethyl)urea (12g)

Light yellow oil. $^1$H NMR (300 MHz, CDCl$_3$) δ 7.03 (d, J=8.7 Hz, 2H), δ 6.78 (t, J=3.9 Hz, 2H), δ 5.85 (q, J=5.1, 6.3 Hz, 2H), δ 3.73 (s, 3H), δ 3.31 (q, J=6.6, 7.2 Hz, 2H), δ 3.12 (m, 2H), δ 2.67 (t, J=7.5 Hz, 2H), δ 1.08 (t, J=7.2 Hz, 3H) ppm; $^{13}$C NMR (75 MHz, CDCl$_3$) δ 159.6, 158.3, 131.7, 129.9, 114.1, 55.4, 42.1, 36.1, 35.1, 15.8 ppm; IR ν$_{max}$ (cm$^{-1}$) 3374, 2977, 2837, 1630; HRMS (ESI) calcd for C$_{12}$H$_{18}$N$_2$O$_2$ (M+) 245.1260. found 245.1263.

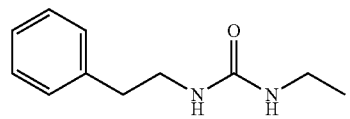

1-ethyl-3-phenethylurea (2g)

White solid. mp=75-77° C. $^1$H NMR (300 MHz, CDCl$_3$) δ 7.22 (m, 5H), δ 5.92 (d, J=16.2 Hz, 2H), δ 3.86 (q, J=6.6, 6.0 Hz, 2H), δ 3.14 (m, 2H), δ 2.78 (t, J=7.8 Hz, 2H), δ 1.10 (t, J=7.2 Hz, 3H) ppm; $^{13}$C NMR (75 MHz, CDCl$_3$) δ 159.6, 139.7, 129.0, 126.5, 41.9, 37.1, 35.1, 15.9 ppm; IR ν$_{max}$ (cm$^{-1}$) 3359, 2972, 2873, 2239, 1633, 1259; HRMS (ESI) calcd for C$_{11}$H$_{16}$N$_2$O (M+) 193.1335. found 193.1334.

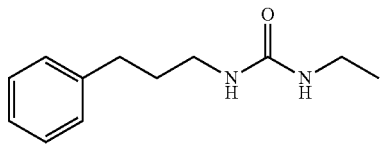

1-ethyl-3-(3-phenylpropyl)urea (4g)

White solid. mp=48° C. $^1$H NMR (300 MHz, CDCl$_3$) δ 7.2 (m, 5H), δ 6.15 (s, 1H), δ 6.08 (s, 1H), δ 3.26 (m, 4H), δ 2.69 (t, J=9 Hz, 2H), δ 1.84 (m, 2H), δ 1.14 (t, J=7.5 Hz, 3H) ppm; $^{13}$C NMR (75 MHz, CDCl$_3$) δ 160.0, 142.0, 128.6, 126.1, 40.0, 35.2, 33.5, 32.4, 15.9 ppm; IR ν$_{max}$ (cm$^{-1}$) 3358, 2971, 2867, 1631; HRMS (ESI) calcd for C$_{12}$H$_{18}$N$_2$O (M+) 207.1492. found 207.1489.

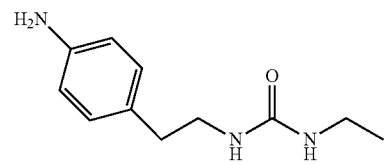

1-(4-aminophenethyl)-3-ethylurea (8g)

Light yellow solid. mp=101-103° C. $^1$H NMR (300 MHz, CDCl$_3$) δ 6.94 (d, J=8.4, 2H), δ 6.58 (d, J=6.0 Hz, 2H), δ 5.05 (t, J=3.3 Hz, 2H), δ 3.59 (s, 2H), δ 3.28 (q, J=6.9, 6.9 Hz, 2H), δ 3.10 (m, 2H), δ 2.63 (t, J=6.9 Hz, 2H), δ 1.04 (t, J=7.2 Hz, 3H) ppm; $^{13}$C NMR (75 MHz, CDCl$_3$) δ 159.0, 145.0, 129.8, 115.5, 42.1, 35.9, 15.7 ppm; IR ν$_{max}$ (cm$^{-1}$) 3409, 1635, 1517, 1263; HRMS (ESI) calcd for C$_{11}$H$_{17}$N$_3$O (M+) 208.1444. found 208.1445.

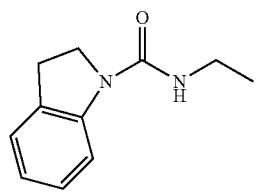

N-ethylindoline-1-carboxamide (6g)

Light yellow solid. mp=111-113° C. $^1$H NMR (300 MHz, CDCl$_3$) δ 7.90 (d, J=8.1 Hz, 1H), δ 7.11-7.04 (m, 2H), δ 6.82 (t, J=7.5 Hz, 1H), δ 5.09 (s, 1H), δ 3.78 (t, J=8.7 Hz, 2H), δ 3.27 (m, 2H), δ 3.02 (t, J=9.0 Hz, 2H), δ 1.15 (t, J=7.2 Hz, 3H) ppm; $^{13}$C NMR (75 MHz, CDCl$_3$) δ ppm; IR ν$_{max}$ (cm$^{-1}$) 3403, 2959, 1646; HRMS (ESI) calcd for C$_{11}$H$_{14}$N$_2$O (M+) 190.1179. found 190.1177.

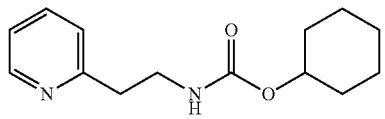 [SMILES: O=C(NCCc1ccccn1)OC1CCCCC1]

cyclohexyl 2-(pyridin-2-yl)ethylcarbamate (9l)

Colorless oil. $^1$H NMR (300 MHz, CDCl$_3$) δ 8.33 (d, J=4.8 Hz, 1H), δ 7.43 (t, J=9.9 Hz, 1H), δ 7.02-6.94 (m, 2H), δ 5.72 (s, 1H), δ 4.45 (d, J=3.6 Hz, 1H), δ 3.40 (q, J=6.6, 6.3 Hz, 2H), δ 2.83 (t, J=6.6 Hz, 2H), δ 1.702-1.027 (m, 10H) ppm; $^{13}$C NMR (75 MHz, CDCl$_3$) δ 159.4, 156.5, 149.1, 136.8, 123.6, 121.6, 40.4, 37.9, 32.2, 25.5, 23.9 ppm; IR ν$_{max}$ (cm$^{-1}$) 3944, 3692, 3054, 2987, 1709; HRMS (ESI) calcd for C$_{14}$H$_{20}$N$_2$O$_2$ (M+) 249.1598. found 249.1595.

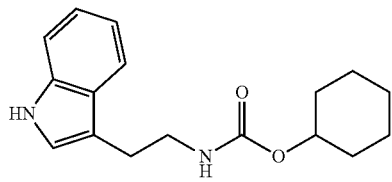 [SMILES: O=C(NCCc1c[nH]c2ccccc12)OC1CCCCC1]

cyclohexyl 2-(1H-indol-3-yl)ethylcarbamate (10l)

Colorless oil. $^1$H NMR (300 MHz, CDCl$_3$) δ 8.74 (s, 1H), δ 7.65 (d, J=6.9 Hz, 1H), δ 7.38 (d, J=7.2 Hz, 1H), δ 7.20 (dd, J=7.2, 7.2 Hz, 2H), δ 6.96 (s, 1H), δ 4.94 (s, 1H), δ 4.72 (s, 1H), δ 3.63 (d, J=34.2 Hz, 2H), δ 2.98 (s, 2H), δ 1.91-1.31 (m, 10H) ppm; $^{13}$C NMR (75 MHz, CDCl$_3$) δ 156.8, 136.8, 127.6, 122.6, 119.5, 112.8, 73.3, 70.6, 41.6, 35.8, 32.4, 26.1, 24.5 ppm; IR ν$_{max}$ (cm$^{-1}$) 3334, 2909, 2991, 1701; HRMS (ESI) calcd for C$_{17}$H$_{22}$N$_2$O$_2$ (M+) 287.1755. found 287.1752.

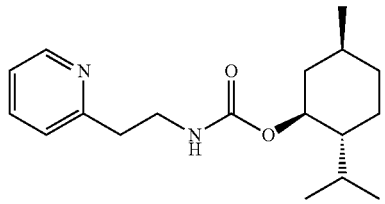 [SMILES: CC(C)[C@H]1CC[C@H](C)C[C@@H]1OC(=O)NCCc1ccccn1]

(1S,2R,5S)-2-isopropyl-5-methylcyclohexyl 2-(pyridin-2-yl)ethylcarbamate (9k)

Yellow solid. mp=57-59° C. $^1$H NMR (300 MHz, CDCl$_3$) δ 8.37 (d, J=4.5 Hz, 1H), δ 7.45 (t, J=5.7 Hz, 1H), δ 6.98 (m, 2H), δ 5.55 (s, 1H), δ 4.40 (t, J=3.9 Hz, 1H), δ 3.43 (q, J=6.3 Hz, 2H), δ 2.85 (t, J=6.3 Hz, 2H), δ 2.01-0.62 (m, 19H) ppm; $^{13}$C NMR (75 MHz, CDCl$_3$) δ 159.5, 156.7, 136.3, 123.6, 121.6, 74.2, 47.5, 41.6, 40.4, 37.9, 34.4, 31.5, 26.7, 23.6, 22.2, 20.9, 16.6 ppm; IR ν$_{max}$ (cm$^{-1}$) 3406, 2954, 2868, 1695, 1694, 1514, 1260; HRMS (ESI) calcd for C$_{18}$H$_{28}$N$_2$O$_2$ (M+) 305.2224. found 305.2221.

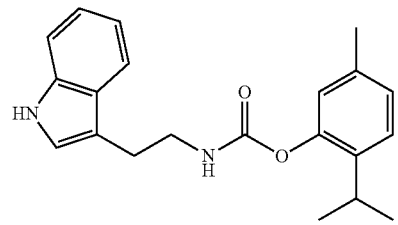 [SMILES: Cc1ccc(C(C)C)c(OC(=O)NCCc2c[nH]c3ccccc23)c1]

2-isopropyl-5-methylphenyl 2-(1H-indol-3-yl)ethylcarbamate (10i)

Colorless oil. $^1$H NMR (300 MHz, CDCl$_3$) δ 8.71 (s, 1H), δ 7.67 (d, J=7.5, 1H), δ 7.37 (d, J=8.1 Hz, 1H), δ 7.25 (t, J=7.2 Hz, 1H), δ 7.20 (t, J=7.2 Hz, 1H), δ 6.96 (s, 1H), δ 4.92 (s, 1H), δ 3.52 (t, J=6.3 Hz, 2H), δ 3.01 (t, J=6.3 Hz, 2H), δ 1.26-1.03 (m, 6H), δ 0.99 (d, J=6.6 Hz, 3H), δ 0.95 (d, J=6.9 Hz, 3H) ppm; $^{13}$C NMR (75 MHz, CDCl$_3$) δ 157.1, 136.8, 127.7, 122.6, 119.0, 112.9, 111.7, 74.9, 47.6, 41.8, 34.6, 31.7, 26.5, 23.8, 22.4, 21.2, 16.8 ppm; IR ν$_{max}$ (cm$^{-1}$) 3408, 2962, 2926, 1717, 1620, 1502, 1457; HRMS (ESI) calcd for C$_{21}$H$_{24}$N$_2$O$_2$ (M+) 337.1911. found 337.1914.

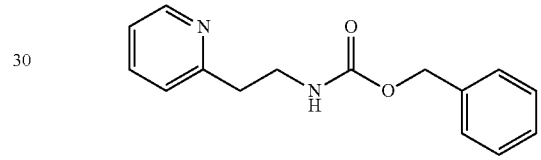

benzyl 2-(pyridin-2-yl)ethylcarbamate (9c)

Colorless oil. $^1$H NMR (300 MHz, CDCl$_3$) δ 8.34 (d, J=6.6 Hz, 1H), δ 7.46 (t, J=7.8 Hz, 1H), δ 6.98 (dd, J=7.8, 7.5 Hz, 2H), δ 5.72 (s, 1H), δ 4.45 (d, J=7.2 Hz, 1H), δ 3.42 (q, J=6.6, 6.3 Hz, 2H), δ 2.83 (t, J=6.6 Hz, 2H), δ 1.70-1.03 (m, 10H) ppm; $^{13}$C NMR (75 MHz, CDCl$_3$) δ 159.4, 156.5, 149.1, 136.8, 123.6, 121.6, 72.8, 40.4, 37.86, 32.2, 25.5, 23.9 ppm; IR ν$_{max}$ (cm$^{-1}$) 3435, 2092, 1644, 1261; HRMS (ESI) calcd for C$_{15}$H$_{16}$N$_2$O$_2$ (M+) 257.1285. found 257.1282.

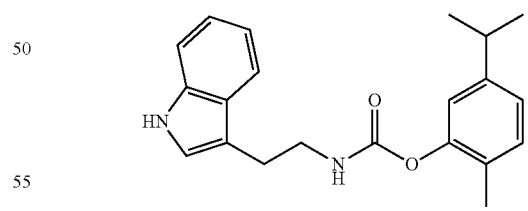

5-isopropyl-2-methylphenyl 2-(1H-indol-3-yl)ethylcarbamate (10j)

$^1$H NMR (300 MHz, CDCl$_3$) δ 8.47 (s, 1H), δ 7.74 (d, J=7.8 Hz, 1H), δ 7.37-7.05 (m, 6H), δ 6.95 (s, 1H), δ 5.35 (s, 1H), δ 3.69 (t, J=6.6 Hz, 2H), δ 3.10 (t, J=6.6 Hz, 2H), δ 2.96 (m, 1H), δ 2.24 (s, 3H), δ 1.33 (d, J=6.6 Hz, 6H) ppm; $^{13}$C NMR (75 MHz, CDCl$_3$) δ 155.24, 149.7, 148.4, 136.8, 131.2, 128.2, 124.7, 122.7, 120.6, 119.6, 118.9, 112.5, 42.0, 33.9, 26.0, 24.3, 16.1 ppm; IR $\nu_{max}$(cm$^{-1}$) 3336, 2969, 2926, 1719, 1503, 1457; HRMS (ESI) calcd for C$_{21}$H$_{24}$N$_2$O$_2$ (M+) 337.1911. found 337.1914.

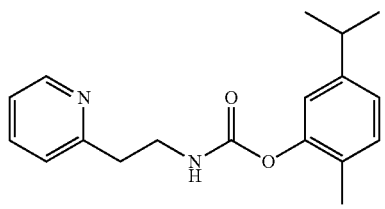 [SMILES: Cc1ccc(C(C)C)cc1OC(=O)NCCc1ccccn1]

5-isopropyl-2-methylphenyl
2-(pyridin-2-yl)ethylcarbamate (9j)

$^1$H NMR (300 MHz, CDCl$_3$) δ 8.55 (d, J=3.9 Hz, 1H), δ 7.67 (t, J=7.8 Hz, 1H), δ 7.27-6.88 (m, 5H), δ 6.46 (t, J=5.4 Hz, 1H), δ 3.68 (q, J=6.6, 6.3 Hz, 2H), δ 3.12 (t, J=6.6 Hz, 2H), δ 2.83 (m, 1H), δ 2.13 (s, 3H), δ 1.23 (d, J=5.1 Hz, 6H) ppm; $^{13}$C NMR (75 MHz, CDCl$_3$) δ 158.7, 155.0, 149.6, 148.1, 138.4, 131.0, 128.0, 124.5, 123.9, 122.4, 120.4, 40.8, 37.0, 33.8, 24.2, 15.9 ppm; IR $\nu_{max}$(cm$^{-1}$) 3054, 2987, 2306, 1734, 1501; HRMS (ESI) calcd for C$_{18}$H$_{22}$N$_2$O$_2$ (M+) 299.1755. found 299.1753.

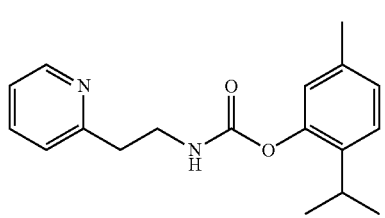 [SMILES: Cc1ccc(C(C)C)c(OC(=O)NCCc2ccccn2)c1]

2-isopropyl-5-methylphenyl
2-(pyridin-2-yl)ethylcarbamate (9i)

$^1$H NMR (300 MHz, CDCl$_3$) δ 8.54 (d, J=4.8 Hz, 1H), δ 7.65 (t, J=7.5 Hz, 1H), δ 7.25-6.94 (m, 4H), δ 6.83 (s, 1H), δ 6.47 (s, 1H), δ 3.68 (q, J=6.0, 6.0 Hz, 2H), δ 3.07 (m, 2H), δ 2.27 (s, 3H), δ 1.16 (d, J=6.0 Hz, 6H) ppm; $^{13}$C NMR (75 MHz, CDCl$_3$) δ 158.8, 155.4, 148.4, 138.2, 137.8, 136.5, 126.9, 126.5, 124.4, 123.4, 122.3, 40.8, 37.1, 27.1, 23.3, 21.1 ppm; IR $\nu_{max}$ (cm$^{-1}$) 3054, 2966, 1735, 1250; HRMS (ESI) calcd for C$_{18}$H$_{22}$N$_2$O$_2$ (M+) 299.1755. found 299.1759.

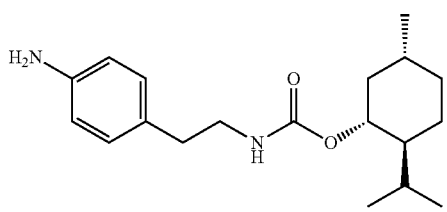 [SMILES: CC(C)[C@@H]1CC[C@@H](C)C[C@H]1OC(=O)NCCc1ccc(N)cc1]

(1R,2S,5R)-2-isopropyl-5-methylcyclohexyl
4-aminophenethylcarbamate (8a)

$^1$H NMR (300 MHz, CDCl$_3$) δ 6.93 (d, J=8.1 Hz, 2H), δ 6.60 (d, J=8.4 Hz, 2H), δ 4.79 (t, J=5.7 Hz, 1H), δ 4.53 (t, J=3.9 Hz, 1H), δ 3.59 (s, 2H), δ 3.33 (q, J=4.5, 5.7 Hz, 2H), δ 2.65 (t, J=6.6 Hz, 2H), δ 2.03 (d, J=6.9 Hz, 1H), δ 1.87 (t, 6.6 Hz, 1H), δ 1.65 (d, 10.5 Hz, 2H), δ 1.43 (s, 3H), δ 1.25 (t, 6.4 Hz, 1H), δ 1.01 (q, J=2.7, 2.7 Hz, 1H), δ 0.92 (m. 6H), δ 0.79 (d, J=7.2 Hz, 3H) ppm; $^{13}$C NMR (75 MHz, CDCl$_3$) δ 156.7, 145.1, 129.8, 128.9, 115.6, 47.6, 42.6, 41.7, 35.4, 34.5, 31.6, 26.5, 23.8, 22.3, 21.1, 16.7 ppm; IR $\nu_{max}$ (cm$^{-1}$) 3442, 2955, 2869, 1698, 1626, 1264; HRMS (ESI) calcd for C$_{19}$H$_{30}$N$_2$O$_2$ (M+) 319.2381. found 319.2383.

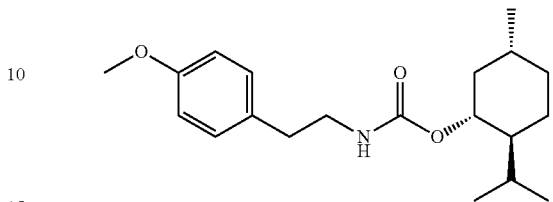

(1R,2S,5R)-2-isopropyl-5-methylcyclohexyl
4-methoxyphenethylcarbamate (12a)

White solid. mp=95-98° C. $^1$H NMR (300 MHz, CDCl$_3$) δ 7.09 (d, J=8.7 Hz, 2H), δ 6.84 (d, J=8.7 Hz, 2H), δ 4.78 (t, J=5.7 Hz, 1H), δ 4.56 (t, 3.9 Hz, 1H), δ 3.74 (s, 3H), δ 3.36 (q, J=6.6, 5.7 Hz, 2H), δ 2.73 (t, 7.2 Hz, 2H), δ 1.99 (d, J=4.8 Hz, 1H), δ 1.66 (t, J=10.2 Hz, 1H), δ 1.48 (d, J=3.0 Hz, 2H), δ 1.47 (t, J=3.3 Hz, 1H), δ 1.07 (t, 3.5 Hz, 1H), δ 1.03 (q, 3.5, 3.0 Hz, 1H), δ 0.93 (m, 6H), δ 0.80 (d, 7.2 Hz, 3H) ppm; $^{13}$C NMR (75 MHz, CDCl$_3$) δ 158.4, 156.7, 131.1, 129.9, 114.2, 55.4, 47.6, 41.7, 35.5, 34.6, 31.6, 26.5, 23.8, 22.3, 21.1, 16.7 ppm; IR $\nu_{max}$(cm$^{-1}$) 3372, 2954, 2869, 1684, 1512, 1455, 1242, 1178, 1127, 1056, 623; HRMS (ESI) calcd for C$_{20}$H$_{31}$NO$_3$ (M+) 356.2196. found 356.2199.

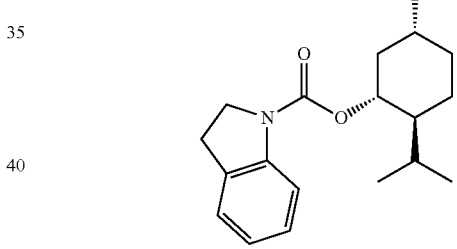

(1R,2S,5R)-2-isopropyl-5-methylcyclohexyl
indoline-1-carboxylate (6a)

Colorless oil. $^1$H NMR (300 MHz, CDCl$_3$) δ 7.90 (s, 1H), δ 7.26 (m, 2H), δ 6.91 (m, 1H), δ 4.75 (s, 1H), δ 3.99 (s, 2H), δ 3.89 (t, 6.6 Hz, 2H), δ 2.19 (d, J=8.7 Hz, 1H), δ 1.95 (s, 1H), δ 1.55 (d, J=2.4 Hz, 2H), δ 1.41 (s, 2H), δ 1.12 (m, 2H), δ 0.84 (m, 10H) ppm; $^{13}$C NMR (75 MHz, CDCl$_3$) δ 127.7, 124.9, 122.5, 114.9, 47.8, 41.9, 34.7, 34.6, 31.7, 27.6, 26.7, 26.6, 23.8, 22.3, 21.1, 16.8, 16.7 ppm; IR $\nu_{max}$ (cm$^{-1}$) 3428, 2955, 2869, 1704, 1604, 1488; HRMS (ESI) calcd for C$_{19}$H$_{27}$NO$_2$ (M+) 324.1934. found 324.1929.

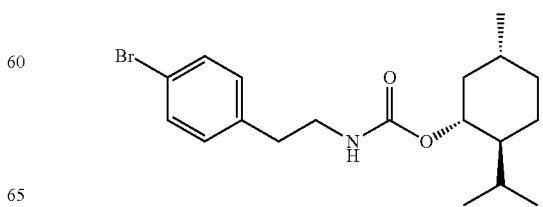

(1R,2S,5R)-2-isopropyl-5-methylcyclohexyl 4-bromophenethylcarbamate (11a)

White solid. mp=104-106° C. $^1$H NMR (300 MHz, CDCl$_3$) δ 7.38 (d, J=5.7 Hz, 2H), δ 7.03 (d, 6.0 Hz, 2H), δ 4.74 (s, 1H), δ 4.51 (t, J=2.7 Hz, 1H), 63.35 (d, J=4.5 Hz, 2H), δ 2.73 (s, 2H), δ 1.99 (d, J=9.0 Hz, 1H), δ 1.64 (t, J=1.5 Hz, 1H), δ 1.63 (t, J=2.4 Hz, 2H), δ 1.41 (m, 1H), δ 1.04 (t, J=3.8 Hz, 1H), δ 1.03 (q, J=2.4 Hz, 2H), δ 0.97 (m, 6H), δ 0.76 (d, J=5.1 Hz, 3H) ppm; $^{13}$C NMR (75 MHz, CDCl$_3$) δ 1.56.6, 138.1, 131.8, 130.8, 120.5, 74.7, 47.6, 42.1, 41.7, 35.8, 34.5, 31.6, 26.5, 23.8, 22.3, 21.0, 16.7 ppm; IR ν$_{max}$ (cm$^{-1}$) 3364, 2953, 2856, 1684, 1256; HRMS (ESI) calcd for C$_{19}$H$_{28}$BrNO$_2$ (M+) 404.1196. found 404.1191.

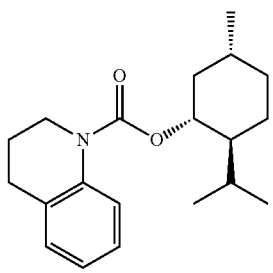 [SMILES: CC(C)[C@@H]1CC[C@@H](C)C[C@H]1OC(=O)N1CCCc2ccccc21]

(1R,2S,5R)-2-isopropyl-5-methylcyclohexyl 3,4-dihydroquinoline-1(2H)-carboxylate (7a)

Colorless oil. $^1$H NMR (300 MHz, CDCl$_3$) δ 7.76 (d, J=8.4 Hz, 1H), δ 7.18 (t, J=1.5 Hz, 1H), δ 7.13 (d, J=1.8 Hz, 1H), δ 6.97, J=0.9 Hz, 1H), δ 4.77 (t, J=4.2 Hz, 1H), δ 3.77 (t, J=0.9 Hz, 2H), δ 2.78 (t, J=6.6 Hz, 2H), δ 1.18 (d, J=3.0 Hz, 1H), δ 1.99 (m, 3H), δ 1.68 (d, J=2.7 Hz, 2H), δ 1.414 (m, 2H), δ 1.13 (m, 2H), δ 1.10 (m, 6H), δ 0.87 (d, J=7.2 Hz, 3H) ppm; $^{13}$C NMR (75 MHz, CDCl$_3$) δ 154.9, 138.7, 129.9, 128.8, 126.1, 124.2, 123.6, 76.5, 47.5, 44.9, 41.7, 34.6, 31.7, 27.7, 26.7, 23.8, 23.8, 22.3, 21.1, 16.7 ppm; IR ν$_{max}$ (cm$^{-1}$) 3434, 2954, 2870, 2105, 1694; HRMS (ESI) calcd for C$_{20}$H$_{29}$NO$_2$ (M+) 338.2091. found 338.2088.

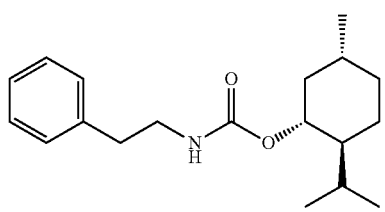 [SMILES: CC(C)[C@@H]1CC[C@@H](C)C[C@H]1OC(=O)NCCc1ccccc1]

(1R,2S,5R)-2-isopropyl-5-methylcyclohexyl phenethylcarbamate (2a)

White solid. mp=84-86° C. $^1$H NMR (300 MHz, CDCl$_3$) δ 7.29 (m, 5H), δ 4.91 (t, J=4.2 Hz, 1H), δ 4.58 (s, 1H), δ 3.39 (s, 2H), δ 2.79 (t, J=7.8 Hz, 2H), δ 2.05 (d, J=8.7 Hz, 1H), δ 1.93 (t, J=4.2 Hz, 1H), δ 1.66 (s, 2H), δ 1.47 (s, 1H), δ 1.28 (t, J=3.8 Hz, 1H), δ 1.04 (q, 10.2, 9.3 Hz, 2H), δ 0.91 (m, 8H), δ 0.80 (d, J=0.60, 3H) ppm; $^{13}$C NMR (75 MHz, CDCl$_3$) δ 156.7, 139.2, 129.1, 128.9, 128.8, 128.7, 126.6, 126.5, 74.6, 47.6, 45.3, 42.4, 41.9, 41.8, 36.5, 34.9, 31.6, 26.5, 23.8, 23.4, 22.6, 22.3, 21.1, 16.4 ppm; IR ν$_{max}$ (cm$^{-1}$) 3360, 2957, 1682, 1526, 1259, 1024, 798; HRMS (ESI) calcd for C$_{19}$H$_{29}$NO$_2$ (M+) 343.2381. found 343.2383.

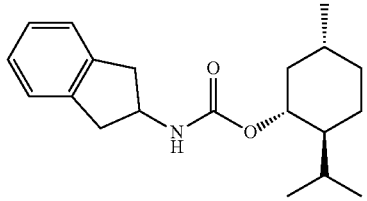 [SMILES: CC(C)[C@@H]1CC[C@@H](C)C[C@H]1OC(=O)NC1Cc2ccccc2C1]

(1R,2S,5R)-2-isopropyl-5-methylcyclohexyl 2,3-dihydro-1H-inden-2-ylcarbamate (3a)

White solid. mp=167-170° C. $^1$H NMR (300 MHz, CDCl$_3$) δ 7.19 (m, 4H), δ 4.99 (s, 1H), δ 4.57 (m, 2H), δ 3.25 (m, 3H), δ 2.75 (m, 2H), δ 2.02 (d, J=11.7 Hz, 2H), δ 1.94 (t, J=2.1 Hz, 1H), δ 1.67 (d, J=12.9, 2H), δ 1.58 (s, 1H), δ 1.45 (t, J=3.3 Hz, 1H), 1.05 (q, J=3.0, 7.5 Hz, 2H), δ 0.93 (m, 6H), δ 0.78 (d, J=7.2 Hz, 6H) ppm; $^{13}$C NMR (75 MHz, CDCl$_3$) δ 159.6, 126.9, 126.8, 124.9, 124.8, 51.6, 50.3, 47.6, 45.3, 41.7, 40.8, 40.6, 34.8, 34.5, 31.0, 31.6, 26.5, 23.7, 23.4, 22.5, 22.3, 21.3, 21.1, 16.6, 16.3 ppm; IR ν$_{max}$ (cm$^{-1}$) 3409, 1688; HRMS (ESI) calcd for C$_{20}$H$_{29}$NO$_2$ (M+) 338.2091. found 338.2098.

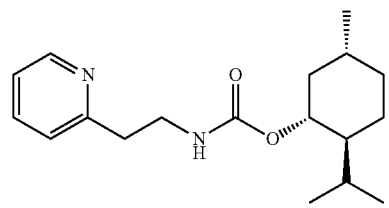 [SMILES: CC(C)[C@@H]1CC[C@@H](C)C[C@H]1OC(=O)NCCc1ccccn1]

(1R,2S,5R)-2-isopropyl-5-methylcyclohexyl 2-(pyridin-2-yl)ethylcarbamate (9a)

White solid. mp=59-63° C. $^1$H NMR (300 MHz, CDCl$_3$) δ 8.50 (q, J=0.6, 2.4 Hz, 1H), δ 7.61 (t, 2.1 Hz, 1H), δ 7.13 (m, 2H), δ 5.75 (s, 1H), δ 4.54 (t, J=7.2 Hz, 1H), δ 3.59 (q, J=5.7, 6.3 Hz, 2H), δ 2.99 (t, J=6.3 Hz, 2H), δ 2.03 (d, J=11.7 Hz, 1H), δ 1.89 (m, 1H), δ 1.59 (tm, 2H), δ 1.27 (s, 1H), δ 1.27 (t, J=10.8 Hz, 1H), δ 0.97 (m, 2H), δ 0.91 (m, 6H), δ 0.76 (d, J=6.9 Hz, 3H) ppm; $^{13}$C NMR (75 MHz, CDCl$_3$) δ 159.5, 156.6, 140.3, 136.5, 123.6, 121.5, 74.2, 71.1, 50.1, 47.5, 41.6, 40.4, 37.9, 34.7, 31.8, 31.4, 26.3, 23.6, 20.9, 16.2 ppm; IR ν$_{max}$ (cm$^{-1}$) 3406, 2954, 2868, 1695, 1694, 1514, 1260; HRMS (ESI) calcd for C$_{18}$H$_{28}$N$_2$O$_2$ (M+) 305.2224. found 305.2229.

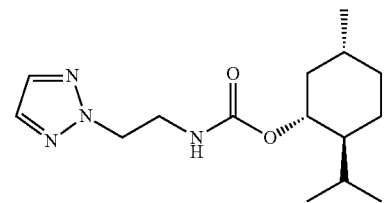 [SMILES: CC(C)[C@@H]1CC[C@@H](C)C[C@H]1OC(=O)NCCn1nccn1]

(1R,2S,5R)-2-isopropyl-5-methylcyclohexyl 2-(2H-1,2,3-triazol-2-yl)ethylcarbamate (5a)

White residue. $^1$H NMR (300 MHz, CDCl$_3$) δ 7.59 (s, 2H), δ 5.11 (s, 1H), δ 4.54 (s, 2H), δ 3.72 (s, 2H), δ 3.24 (s, 1H), δ 1.90 (m, 2H), δ 1.61 (s, 1H), δ 1.52 (s, 2H), δ 1.45 (s, 1H), δ 1.24 (s, 1H), 1.09 (m, 2H), δ 1.05 (m, 8H), δ 0.76 (d, J=4.2 Hz, 3H) ppm; $^{13}$C NMR (75 MHz, CDCl$_3$) δ 156.5, 134.6, 74.8, 71.7, 54.7, 50.3, 47.7, 47.5, 41.8, 40.5, 34.5, 31.6, 26.5, 23.7, 22.2, 16.3 ppm; IR ν$_{max}$ (cm$^{-1}$) 3434, 2955, 2088, 1642, 1256; HRMS (ESI) calcd for C$_{15}$H$_{26}$N$_4$O$_2$ (M+) 304.4125. found 304.4129.

(3S,8S,9S,10R,13R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl 2-(2H-1,2,3-triazol-2-yl)ethylcarbamate (5f)

White solid. mp=135-139° C. $^1$H NMR (300 MHz, CDCl$_3$) δ 7.58 (s, 2H), δ 5.31 (t, 6.9 Hz, 1H), δ 4.53 (t, J=5.1 Hz, 1H), δ 3.69 (q, J=5.1 Hz, 2H) δ 3.47 (m, 2H), δ 2.49 (s, 1H), δ 2.45 (q, J=9.3, 4.2 Hz, 2H), δ 1.96 (m, 6H), δ 1.54-1.30 (m, 11H), δ 1.25-1.09 (m, 14H), 61.01-0.82 (m, 10H), 60.65 (s, 3H) ppm; $^{13}$C NMR (75 MHz, CDCl$_3$) δ141.1, 134.6, 121.8, 71.8, 57.0, 56.9, 50.3, 42.5, 40.0, 39.8, 37.5, 36.7, 36.4, 36.1, 32.1, 31.8, 28.5, 28.2, 24.5, 24.1, 23.1, 229, 21.3, 19.6, 19.5, 18.9, 12.1 ppm; IR ν$_{max}$ (cm$^{-1}$) 3398, 2037, 1637; HRMS (ESI) calcd for C$_{32}$H$_{52}$N$_4$O$_2$ (M+) 547.3982. found 547.3981.

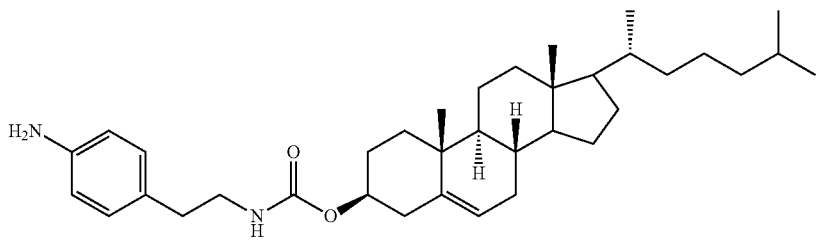

(3S,8S,9S,10R,13R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl 4-aminophenethylcarbamate (8f)

Yellow hygroscopic solid. $^1$H NMR (300 MHz, CDCl$_3$) δ 6.93 (d, J=7.5 Hz, 2H), δ 6.588 (d, J=7.5 Hz, 2H), δ 5.35 (m, 1H), δ 4.92 (s, 1H), δ 4.47 (m, 1H), 63.32 (d, J=6.0 Hz, 2H), δ 2.54 (t, J=6.6 Hz, 2H), δ 2.31 (m, 2H), δ 2.02-1.98 (m, 5H), δ 1.54-1.27 (m, 11H), δ 1.10-0.85 (m, 24H), δ 0.67 (s, 3H) ppm; $^{13}$C NMR (75 MHz, CDCl$_3$) δ 156.4, 145.2, 141.2, 140.1, 129.8, 128.8, 122.7, 115.6, 74.4, 57.-, 56.9, 56.4, 50.2, 42.6, 40.0, 39.8, 38.9, 37.3, 36.8, 36.5, 35.5, 32.1, 31.8, 28.4, 28.3, 24.5, 24.2, 23.2, 22.0, 21.3, 10.7, 19.5, 19.0, 12.1 ppm; IR ν$_{max}$ (cm$^{-1}$) 3407, 2937, 2868, 2245, 1695, 1631, 1516; HRMS (ESI) calcd for C$_{36}$H$_{56}$N$_2$O$_2$ (M+) 549.4415. found 549.4420.

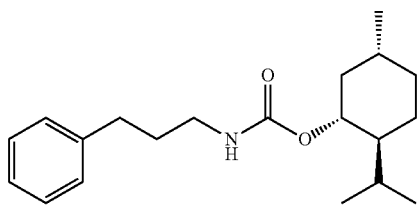 [SMILES: CC(C)[C@@H]1CC[C@@H](C)C[C@H]1OC(=O)NCCCc1ccccc1]

(1R,2S,5R)-2-isopropyl-5-methylcyclohexyl 3-phenylpropylcarbamate (4a)

White solid. mp=75-78° C. $^1$H NMR (300 MHz, CDCl$_3$) δ 7.28 (t, J=7.8 Hz, 2H), δ 7.16 (d, J=7.2 Hz, 2H), δ 4.86 (s, 1H), δ 4.55 (t, J=6.9 Hz, 1H), δ 3.201 (q, J=6.6, 6.0 Hz, 2H), δ 2.64 (t, J=7.5 Hz, 2H), δ 2.05 (d, J=11.7 Hz, 1H), δ 1.95 (t, J=2.7 Hz, 1H), δ 1.89 (m, 2H), δ 1.66 (d, J=10.8 Hz, 2H), δ 1.48 (s, 1H), δ 1.06 (t, J=8.4 Hz, 1H), δ 1.06 (m, 2H), δ 1.02 (m, 8H), δ 0.80 (d, J=6.9 Hz, 3H) ppm; $^{13}$C NMR (75 MHz, CDCl$_3$) δ 156.9, 141.8, 128.7, 128.6, 126.2, 126.1, 74.6, 47.4, 41.8, 40.1, 34.6, 33.5, 33.3, 31.9, 31.6, 26.6, 23.8, 22.4, 16.8 ppm; IR ν$_{max}$ (cm$^{-1}$) 3410, 3057, 2960, 1713, 1421, 1362, 1267, 1222, 191, 846, 736, 702; HRMS (ESI) calcd for C$_{20}$H$_{31}$NO$_2$ (M+) 340.2247. found 340.2241.

(3S,8S,9S,10R,13R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl 2,3-dihydro-1H-inden-2-ylcarbamate (3f)

mp=114-116° C. $^1$H NMR (300 MHz, CDCl$_3$) δ 7.19 (m, 4H), δ 5.37 (d, J=6.6 Hz, 1H), δ 5.15 (m, 1H), δ 4.52 (s, 1H), δ 3.40 (m, 1H), δ 3.24 (m, 2H), δ 2.78 (m, 2H), δ 2.27 (m, 3H), δ 2.04-1.84 (m, 5H), δ 1.55-1.26 (m, 11H), δ 1.12-0.87 (m, 23H), δ 0.69 (s, 3H) ppm; $^{13}$C NMR (75 MHz, CDCl$_3$) δ 141.4, 126.9, 125.0, 124.9, 122.8, 121.89, 71.9, 57.0, 56.9, 56.4, 52.4, 51.7, 50.4, 50.2, 42.5, 42.5, 40.8, 40.5, 40.1, 40.0, 39.8, 37.6, 36.8, 36.5, 36.1, 32.2, 32.1, 31.8, 28.5, 28.5, 24.6, 24.2, 23.1, 22.9, 21.4, 21.3, 19.7, 19.6, 19.0, 12.1 ppm; IR ν$_{max}$ (cm$^{-1}$) 3358, 2937, 2867, 1693, 1551, 1466; HRMS (ESI) calcd for C$_{37}$H$_{55}$NO$_2$ (M+) 568.4125. found 568.4136.

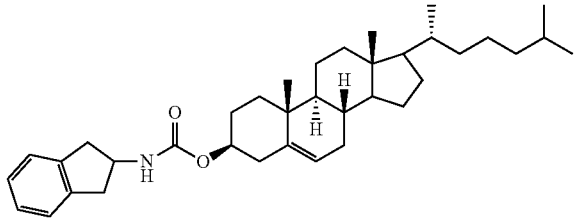

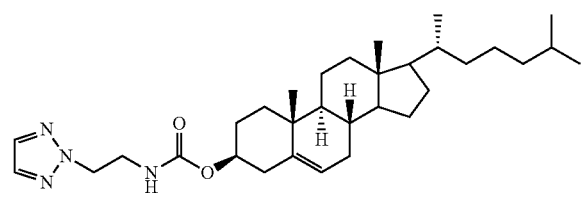

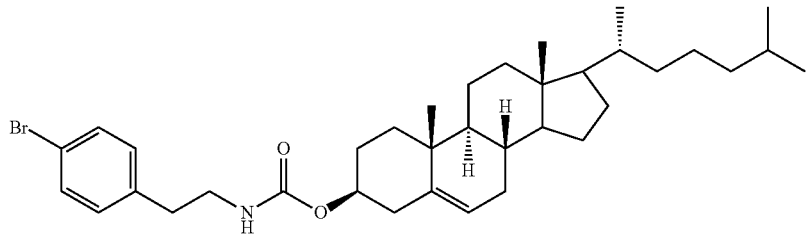

(3S,8S,9S,10R,13R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl 4-bromophenethylcarbamate (11f)

White solid. mp=142-145° C. $^1$H NMR (300 MHz, CDCl$_3$) δ 7.37 (d, J=8.4 Hz, 2H), δ 6.99 (d, J=8.4 Hz, 2H), δ 5.34 (s, 1H), δ 4.98 (t, J=5.7, 1H), δ 4.44 (m, 1H), δ 3.34 (q, J=6.6 Hz, 1H), δ 2.72 (t, J=6.6 Hz, 2H), δ 2.27 (m, 2H), δ 2.32-1.79 (m, 5H), δ 1.52-1.34 (m, 11H), δ 1.22-0.86 (m, 22H), δ 0.65 (s, 3H) ppm; $^{13}$C NMR (75 MHz, CDCl$_3$) δ 202.3, 156.3, 139.1, 138.1, 131.9, 131.7, 130.8, 122.8, 120.5, 74.5, 56.9, 57.4, 50.2, 42.5, 42.1, 39.9, 39.8, 38.8, 37.3, 36.8, 36.5, 36.1, 32.1, 29.6, 28.4, 28.2, 24.5, 24.2, 23.1, 22.9, 21.3, 19.6, 19.0, 12.1 ppm; IR ν$_{max}$ (cm$^{-1}$) 3435, 2947, 2867, 2249, 1793, 1488; HRMS (ESI) calcd for C$_{36}$H$_{54}$BrNO$_2$ (M+) 634.3230. found 634.3210.

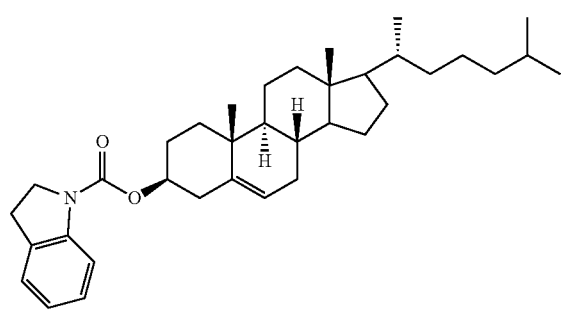

(3S,8S,9S,10R,13R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl indoline-1-carboxylate (6f)

White solid, mp=157-159° C. $^1$H NMR (300 MHz, CDCl$_3$) δ 7.86 (s, 1H), δ 7.16 (t, 2H), δ 6.93 (t, J=7.5 Hz, 1H), δ 5.44 (d, J=4.5 Hz, 1H), δ 4.68 (s, 1H), δ 3.98 (t, J=7.5 Hz, 2H), δ 3.07 (t, J=8.7 Hz, 2H), δ 2.07-1.84 (m, 5H), δ 1.59-1.28 (m, 11H), δ 1.21-1.04 (m, 10H), δ 1.03-0.90 (m, 12H), δ 0.72 (s, 3H) ppm; $^{13}$C NMR (75 MHz, CDCl$_3$) δ 202.3, 149.9, 139.9, 127.7, 122.9, 122.6, 115.1, 75.1, 56.9, 56.5, 50.3, 47.6, 42.6, 40.0, 39.8, 37.7, 37.3, 36.8, 36.8, 36.4, 32.2, 32.1, 31.8, 28.6, 28.3, 27.6, 24.6, 24.3, 23.2, 22.9, 21.4, 19.7, 19.0, 12.2 ppm; IR ν$_{max}$ (cm$^{-1}$) 3444, 2944, 1699, 1604; HRMS (ESI) calcd for C$_{36}$H$_{53}$NO$_2$ (M+) 532.4150. found 532.4152.

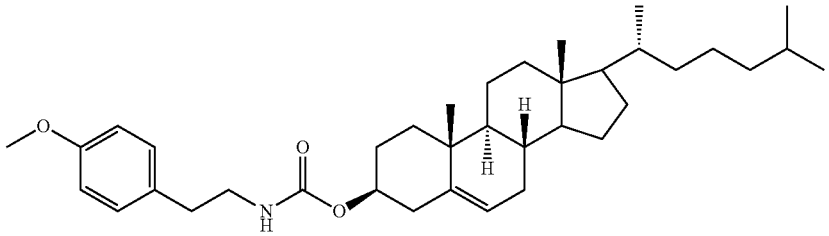

(3S,8S,9S,10R,13R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl 4-methoxyphenethylcarbamate (12f)

White residue. $^1$H NMR (300 MHz, CDCl$_3$) δ 7.10 (d, J=6.6 Hz, 2H), δ 6.83 (d, J=6.6 Hz, 2H), δ 5.37 (d, J=4.8 Hz, 1H), δ 4.88 (s, 1H), δ 4.48 (m, 1H), δ 3.75 (s, 3H), δ 3.36 (q, J=6.0, 6.6 Hz, 2H), δ 2.72 (t, J=6.9 Hz, 2H), δ 2.32 (m, 2H), δ 1.98-1.81 (m, 5H), δ 1.52-1.36 (m, 11H), δ 1.28-1.13 (m, 12H), δ 1.11-0.86 (m, 10H), δ 0.67 (s, 3H) ppm; $^{13}$C NMR (75 MHz, CDCl$_3$) δ 158.5, 156.4, 140.0, 131.1, 129.9, 122.7, 114.2, 114.1, 74.5, 56.9, 56.4, 55.4, 50.2, 42.5, 39.9, 39.8, 38.8, 37.3, 36.8, 36.5, 36.1, 35.5, 32.1, 28.5, 28.4, 28.3, 24.5, 24.1, 23.1, 22.9, 21.3, 19.6, 18.9, 12.1 ppm; IR ν$_{max}$ (cm$^{-1}$) 3418, 2937, 2867, 1695, 1512, 1465, 1246, 733; HRMS (ESI) calcd for C$_{37}$H$_{57}$NO$_3$ (M+) 586.4231. found 586.4230.

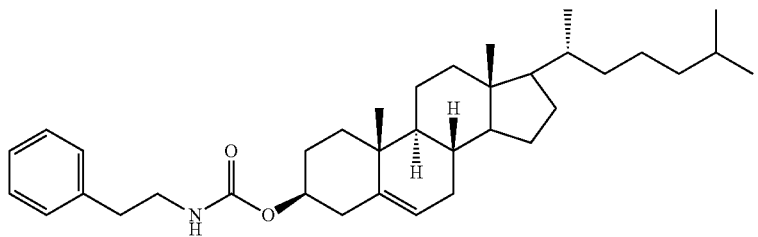

(3S,8S,9S,10R,13R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl phenethylcarbamate (2f)

White solid. mp=74-76° C. $^1$H NMR (300 MHz, CDCl$_3$) δ 7.39 (t, J=1.2 Hz, 2H), δ 7.18 (m, 3H), δ 5.36 (d, J=2.7 Hz, 1H), δ 4.83 (s, 1H), δ 4.48 (m, 1H), δ 3.39 (d, J=4.5 Hz, 2H), δ 2.33 (m, 2H), δ 2.02-1.82 (m, 5H), δ 1.55-1.33 (m, 18H), δ 1.12-1.03 (m, 7H), δ 0.96-0.86 (m, 9H), δ 0.67 (s, 3H) ppm; $^{13}$C NMR (75 MHz, CDCl$_3$) δ 156.36, 140.1, 129.1, 129.0, 128.8, 128.7, 126.7, 122.7, 56.0, 56.5, 50.3, 42.6, 42.4, 40.0, 39.8, 38.9, 37.3, 36.8, 36.5, 36.1, 32.2, 32.1, 28.5, 28.5, 28.3, 24.6, 23.2, 22.9, 21.3, 10.6, 10.0, 12.1 ppm; IR ν$_{max}$ (cm$^{-1}$) 3419, 2944, 2867, 2089, 1694, 1255, 1137; HRMS (ESI) calcd for C$_{36}$H$_{55}$NO$_2$ (M+) 556.4125. found 556.4128.

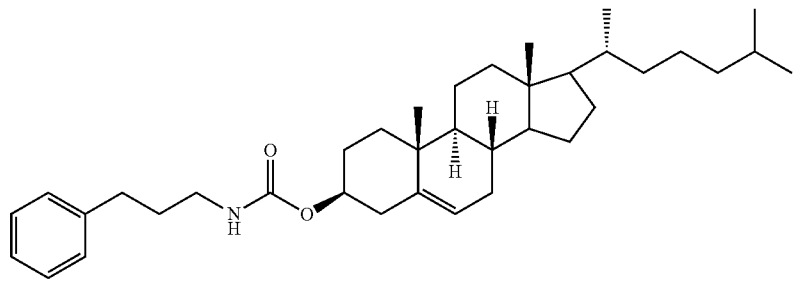

(3S,8S,9S,10R,13R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl 3-phenylpropylcarbamate (4f)

White solid. mp=87-89° C. $^1$H NMR (300 MHz, CDCl$_3$) δ 7.24 (t, J=3.3 Hz, 2H), δ 7.25 (t, J=5.4 Hz, 3H), δ 5.35 (d, J=3.6 Hz, 1H), δ 4.89 (t, J=4.5 Hz, 1H), δ 4.49 (m, 1H), δ 3.17 (d, J=4.8 Hz, 2H), δ 2.35 (m, 2H), δ 2.01-1.78 (m, 8H), δ 1.55=1.41 (m, 11H), δ 1.29-1.12 (m, 12H), δ 1.05-0.91 (m, 11H), δ 0.67 (s, 3H) ppm; $^{13}$C NMR (75 MHz, CDCl$_3$) δ 156.5, 141.7, 140.1, 128.7, 128.6, 126.2, 122.7, 74.4, 56.9, 56.5, 50.3, 42.6, 50.7, 50.0, 39.8, 38.9, 37.3, 36.9, 36.5, 35.1, 33.4, 32.1, 31.9, 28.5, 28.4, 28.3, 24.5, 24.2, 23.2, 22.9, 21.3, 19.6, 19.0, 12.2 ppm; IR ν$_{max}$ (cm$^{-1}$) 3419, 2944, 2867, 2089, 1694, 1255, 1137; HRMS (ESI) calcd for C$_{37}$H$_{57}$NO$_2$ (M+) 570.4282. found 570.4287.

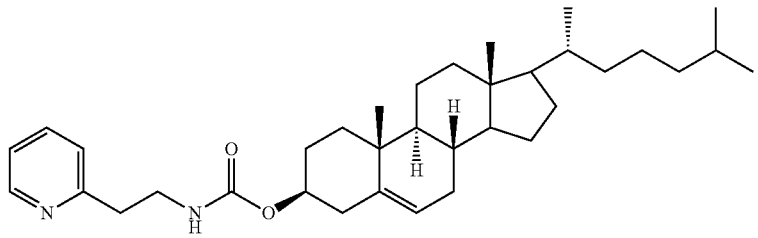

(3S,8S,9S,10R,13R)-10,13-dimethyl-17-((R)-6-methylheptan-2-yl)-2,3,4,7,8,9,10,11,12,13,14,15,16, 17-tetradecahydro-1H-cyclopenta[a]phenanthren-3-yl 2-(pyridin-2-yl)ethylcarbamate (9f)

White residue. $^1$H NMR (300 MHz, CDCl$_3$) δ 8.50 (d, J=3.6 Hz, 1H), δ 7.59 (t, 0.9 Hz, 1H), δ 5.7 (d, J=5.7 Hz, 1H), δ 7.09 (t, J=5.7 Hz, 1H), δ 5.73 (s, 1H), δ 5.35 (s, 1H), δ 4.49 (s, 1H), δ 3.58 (d, J=4.2 Hz, 2H), δ 2.99 (t, J=4.8 Hz, 2H), δ 2.34 (m, 2H), δ 2.02-1.81 (m, 5H), δ 1.54-1.34 (m, 10H), δ 1.19-1.08 (m, 11H), δ 1.06-0.86 (m, 14H), δ 0.68 (s, 3H) ppm; $^{13}$C NMR (75 MHz, CDCl$_3$) δ 159.6, 156.3, 149.4, 140.0, 136.6, 123.6, 122.5, 121.6, 74.2, 56.9, 56.4, 50.2, 42.5, 40.4, 39.9, 39.7, 38.8, 37.0, 36.7, 36.4, 32.1, 32.0, 28.4, 28.4, 28.2, 24.5, 24.1, 23.0, 22.8, 21.2, 19.5, 18.9, 12.1 ppm; IR ν$_{max}$ (cm$^{-1}$) 3434, 2938, 2869, 2094, 1708, 1641, 1264; HRMS (ESI) calcd for C$_{35}$H$_{54}$N$_2$O$_2$ (M+) 535.4259. found 535.4257.

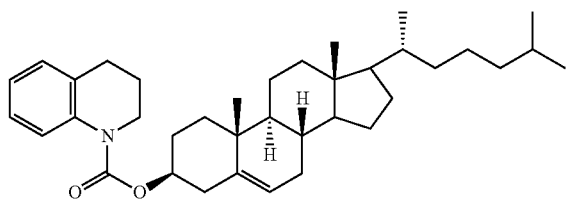

(3S,8S,9S,10R,13R)-10,13-dimethyl-17-((R)-6-methylheptan-2-yl)-2,3,4,7,8,9,10,11,12,13,14,15,16, 17-tetradecahydro-1H-cyclopenta[a]phenanthren-3-yl 3,4-dihydroquinoline-1(2H)-carboxylate (7f)

White solid. mp=107-110° C. $^1$H NMR (300 MHz, CDCl$_3$) δ 7.71 (d, J=8.1 Hz, 1H), δ 7.18 (t, J=7.5 Hz, 1H), δ 7.09 (d, J=7.2 Hz, 1H), δ 6.99 (t, J=7.5 Hz, 1H), δ 5.41 (d, J=4.21 Hz, 1H), δ 4.65 (m, 1H), δ 3.76 (t, J=5.7 Hz, 2H), δ 2.77 (t, J=6.6 Hz, 2H), δ 2.45 (m, 2H), δ 2.04-1.89 (m, 7H), δ 1.86-1.55 (m, 8H), δ 1.44-1.15 (m, 10H), δ 1.12-1.04 (m, 9H), δ 0.94-0.88 (m, 9H), δ 0.69 (s, 3H), $^{13}$C NMR (75 MHz, CDCl$_3$) δ 154.6, 140.0, 138.6, 130.1, 128.8, 126.1, 124.2, 123.6, 122.8, 75.9, 56.9, 56.4, 40.3, 44.9, 42.6, 39.9, 39.8, 38.8, 37.3, 36.9, 36.4, 36.1, 32.2, 32.1, 28.5, 28.4, 28.3, 27.7, 24.5, 24.1, 23.7, 23.1, 22.1, 21.3, 19.5, 18.9, 12.1 ppm; IR ν$_{max}$ (cm$^{-1}$) 3408, 2962, 2927, 1717, 1620, 1602, 1457; HRMS (ESI) calcd for C$_{37}$H$_{55}$NO$_2$ (M+) 568.4125. found 568.4127.

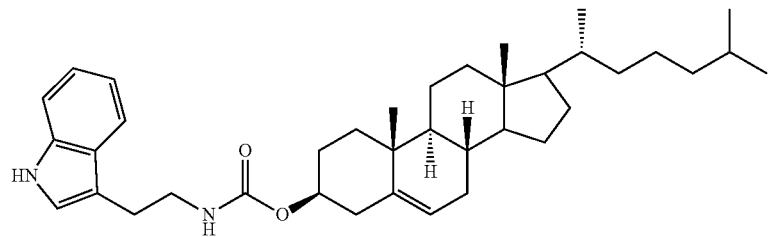

(3S,8S,9S,10R,13R)-10,13-dimethyl-17-((R)-6-methylheptan-2-yl)-2,3,4,7,8,9,10,11,12,13,14,15,16, 17-tetradecahydro-1H-cyclopenta[a]phenanthren-3-yl 2-(1H-indol-3-yl)ethylcarbamate (10f)

Light yellow solid. mp=149-152° C. $^1$H NMR (300 MHz, CDCl$_3$) δ 8.57 (s, 1H), δ 7.54 (d, J=7.2 Hz, 1H), δ 7.26 (d, J=7.2 Hz, 1H), δ 7.10 (m, 2H), δ 6.79 (s, 1H), δ 5.31 (s, 1H), δ 4.90 (s, 1H), δ 4.52 (s, 1H), δ 3.41 (s, 2H), δ 2.87 (s, 2H, δ 2.27 (s, 2H), δ 1.99-1.77 (m, 5H), δ 1.52-1.34 (m, 11H), δ 1.12-0.88 (m, 22H), δ 0.66 (s, 3H) ppm; $^{13}$C NMR (75 MHz, CDCl$_3$) δ 156.8, 140.0, 136.8, 127.6, 122.9, 122.6, 122.2, 119.5, 118.9, 112.8, 111.8, 74.7, 56.9, 56.5, 50.3, 42.6, 41.7, 40.1, 39.9, 38.9, 37.3, 36.8, 36.5, 36.2, 32.2, 28.6, 28.4, 24.7, 23.3, 22.9, 21.4, 19.7, 19.2, 12.2 ppm; IR ν$_{max}$ (cm$^{-1}$) 3412, 3056, 2945, 2868, 2247, 1697, 1515; HRMS (ESI) calcd for C$_{36}$H$_{54}$N$_2$O$_2$ (M+) 547.4259. found 547.4257.

BIOLOGY EXPERIMENTAL

Procedure to Determine the Inhibitory Effect of Test Compounds.

Inhibition assays were performed by taking an overnight culture of bacterial strain and subculturing it at an OD$_{600}$ of 0.01 into the medium. Stock solutions of predetermined concentrations of the test compound were then made in the medium. These stock solutions were aliquoted (100 µL) into the wells of the 96-well PVC microtiter plate. Sample plates were then wrapped in GLAD Press n'Seal® followed by an incubation under stationary conditions for 24 h at 37° C. After incubation, the medium was discarded from the wells and the plates were washed thoroughly with water. Plates were then stained with 100 µL of 0.1% solution of crystal violet (CV) and then incubated at ambient temperature for 30 min. Plates were washed with water again and the remaining stain was solubilized with 200 µL of 95% ethanol. A sample of 125 µL of solubilized CV stain from each well was transferred to the corresponding wells of a polystyrene microtiter dish. Biofilm inhibition was quantitated by measuring the OD$_{540}$ of each well in which a negative control lane wherein no biofilm was formed served as a background and was subtracted out.

Colony Count Procedure to Determine the Effect of Leading Test Compounds on MRSA and E. Coli Planktonic Viability:

Colony counts were performed by taking an overnight culture of bacterial strain and subculturing it at an OD$_{600}$ of 0.01 into the necessary medium (tryptic soy broth with a 0.5% glucose supplement (TSBG) for MRSA, Luria-Bertani (LB) medium for E. coli). The resulting bacterial suspension was then aliquoted (3.0 mL) into culture tubes. A test compound was then added to the medium of the test samples at a predetermined concentration to the medium of the test samples. Controls were employed in which no test compound was added to the bacterial suspension. Samples were then placed in an incubator at 37° C. and shaken at 200 rpm until the OD$_{600}$ of the control samples reached approximately 1.2. At this point, 100 µL was taken from each culture tube and then diluted serially into LB medium. Then, 10 µL was removed from each serial dilution and plated out on a square gridded Petri dish followed by 16 h of incubation at 37° C. to grow viable colonies, which were quantified through employment of the track-dilution method.

Red Blood Cell Hemolysis Assay.

Hemolysis assays were performed on mechanically difibrinated sheep blood (Hemostat Labs: DSB100). 1.5 mL of blood was placed into a microcentrifuge tube and centrifuged at 10000 rpm for ten minutes. The supernatant was removed and then the cells were resuspended with 1 mL of phosphate-buffered saline (PBS). The suspension was centrifuged, the supernatant was removed and cells resuspended two more times. The final cell suspension was then diluted tenfold. Test compound solutions were made in PBS in small culture tubes and then added to aliquots of the tenfold suspension dilution. PBS alone was used as a negative control and as a zero hemolysis marker whereas a 1% Triton X sample was used as a positive control and the 100% lysis marker. Samples were then placed in an incubator at 37° C. while being shaken at 200 rpm for one hour. After one hour, the samples were transferred to microcentrifuge tubes and then centrifuged at 10000 rpm for ten minutes. The resulting supernatant was diluted by a factor of 40 in distilled water. The absorbance of the supernatant was measured with a UV spectrometer at a 540 nm wavelength.

The foregoing is illustrative of the present invention, and is not to be construed as limiting thereof. The invention is defined by the following claims, with equivalents of the claims to be included therein.

That which is claimed is:

1. A compound of Formula (I)(b):

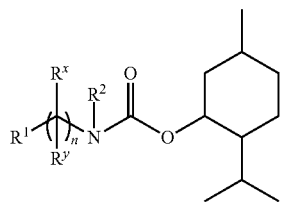

wherein:
R$^1$ is an amine-substituted aryl, or R$^1$ is a heteroaryl selected from the group consisting of: indazolyl, indolizinyl, isoindolyl, isoquinolyl, isothiazolyl, naphthyridinyl, phthalazinyl, purinyl, pyrazinyl, pyridazinyl, 2-pyridinyl, 3-pyridinyl, 4-pyridinyl, pyrimidinyl, pyrrolyl, quinolyl, quinoxalinyl and triazolyl;
n=2 to 10, saturated or unsaturated;
each occurrence of R$^x$ and R$^y$ is present or absent (depending upon chain saturation), and is each independently H or alkyl; and
R$^2$ is selected from the group consisting of: H, alkyl, alkenyl and alkynyl,
or a pharmaceutically acceptable salt thereof.

2. The compound of claim 1, wherein R$^1$ is selected from the group consisting of:

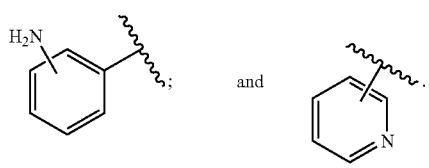

3. The compound of claim 1, wherein said compound is a compound of Formula (I)(a)(i):

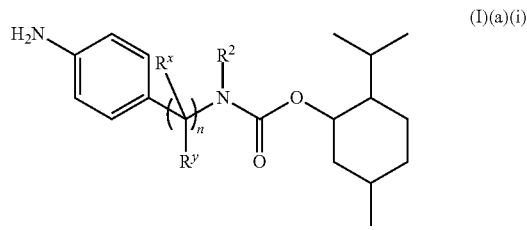

wherein:
n=2 to 10, saturated or unsaturated;
each occurrence of R$^x$ and R$^y$ is present or absent (depending upon chain saturation), and is each independently H or alkyl; and
R$^2$ is selected from the group consisting of: H and alkyl,
or a pharmaceutically acceptable salt thereof.

4. The compound of claim 1, wherein said compound is a compound of Formula (I)(a)(ii):

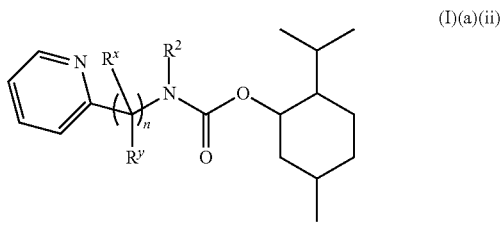

wherein:
n=2 to 10, saturated or unsaturated;
each occurrence of R$^x$ and R$^y$ is present or absent (depending upon chain saturation), and is each independently H or alkyl; and
R$^2$ is selected from the group consisting of: H and alkyl,
or a pharmaceutically acceptable salt thereof.

5. The compound of claim 1, wherein n=2 to 5.
6. The compound of claim 1, wherein n=2 to 5, saturated.
7. The compound of claim 1, wherein said compound is selected from the group consisting of:

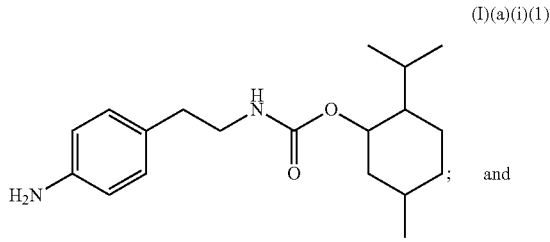

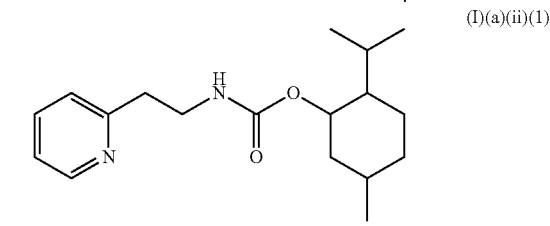

or a pharmaceutically acceptable salt thereof.

8. A composition comprising a carrier and an effective amount of the compound of claim 1.

9. A composition comprising the compound of claim 1 and a biocide.

* * * * *